US011342046B2

(12) United States Patent
Sarmiento et al.

(10) Patent No.: US 11,342,046 B2
(45) Date of Patent: May 24, 2022

(54) METHODS AND SYSTEMS FOR ENGINEERING BIOMOLECULES

(71) Applicant: Codexis, Inc., Redwood City, CA (US)

(72) Inventors: Russell Javiniar Sarmiento, Redwood City, CA (US); Donald Scott Baskerville, Burlingame, CA (US); Xiyun Zhang, Fremont, CA (US)

(73) Assignee: Codexis, Inc., Redwood City, CA (US)

( * ) Notice: Subject to any disclaimer, the term of this patent is extended or adjusted under 35 U.S.C. 154(b) by 6 days.

(21) Appl. No.: 16/434,138

(22) Filed: Jun. 6, 2019

(65) Prior Publication Data

US 2020/0020415 A1  Jan. 16, 2020

Related U.S. Application Data

(63) Continuation of application No. 14/498,881, filed on Sep. 26, 2014, now abandoned.

(60) Provisional application No. 61/883,919, filed on Sep. 27, 2013.

(51) Int. Cl.
| G16B 15/00 | (2019.01) |
| G16B 40/00 | (2019.01) |
| G16B 5/00  | (2019.01) |
| G16C 10/00 | (2019.01) |
| G16B 35/20 | (2019.01) |
| G16B 15/30 | (2019.01) |
| C12N 15/10 | (2006.01) |
| G16B 15/20 | (2019.01) |
| G16C 20/50 | (2019.01) |

(52) U.S. Cl.
CPC ......... *G16B 15/00* (2019.02); *C12N 15/1058* (2013.01); *G16B 5/00* (2019.02); *G16B 15/20* (2019.02); *G16B 15/30* (2019.02); *G16B 35/20* (2019.02); *G16B 40/00* (2019.02); *G16C 10/00* (2019.02); *G16C 20/50* (2019.02)

(58) Field of Classification Search
None
See application file for complete search history.

(56) References Cited

U.S. PATENT DOCUMENTS

| 6,969,763 B1 | 11/2005 | Ecker et al. |
| 7,747,393 B2 | 6/2010 | Fox |
| 8,762,066 B2 | 6/2014 | Fox |
| 10,696,964 B2 | 6/2020 | Zhang et al. |
| 2002/0099506 A1 | 7/2002 | Floriano et al. |
| 2002/0133297 A1 | 9/2002 | Yang et al. |
| 2006/0099667 A1 | 5/2006 | Andre et al. |
| 2006/0121455 A1 | 6/2006 | Goddard et al. |
| 2006/0136184 A1* | 6/2006 | Gustafsson ............ G16B 20/00 703/11 |
| 2009/0118130 A1 | 5/2009 | Mundorff et al. |
| 2014/0303952 A1 | 10/2014 | Wang et al. |
| 2015/0133307 A1 | 5/2015 | Zhang et al. |
| 2015/0134315 A1 | 5/2015 | Sarmiento et al. |
| 2016/0136184 A1 | 5/2016 | DeLuca et al. |
| 2020/0277597 A1 | 9/2020 | Zhang et al. |

FOREIGN PATENT DOCUMENTS

| CN | 1468959 A | 1/2004 |
| CN | 101484462 A | 7/2009 |
| CN | 102156823 A | 8/2011 |
| CN | 102164952 A | 8/2011 |
| CN | 102939383 A | 2/2013 |
| CN | 103265635 A | 8/2013 |
| CN | 103324861 A | 9/2013 |
| EP | 2 216 429 A1 | 8/2010 |
| JP | 04-179495 A | 6/1992 |
| JP | 2005-309877 A | 11/2005 |
| JP | 2009-525274 A | 7/2009 |
| KR | 2008-0099278 A | 11/2008 |
| RU | 2008 140 858 A | 4/2010 |
| RU | 2453911 C2 | 6/2012 |
| WO | WO 2006/044378 A2 | 4/2006 |
| WO | WO 2006/121455 A1 | 11/2006 |
| WO | WO 2007/087266 A2 | 8/2007 |
| WO | WO 2010/077470 A2 | 7/2010 |
| WO | WO 2015/048572 A1 | 4/2015 |
| WO | WO 2015/048573 A1 | 4/2015 |

OTHER PUBLICATIONS

Ning et al. Drug Development Research 72, p. 138-146, 2011.*
Murphy et al. Nature Chemical Biology, 7, 327-330, 2011.*
Hecht et al. Drug Development Research 72, p. 53-65, 2011.*
U.S. Office Action dated Nov. 17, 2016 issued in U.S. Appl. No. 14/498,864.
U.S. Final Office Action dated May 15, 2017 issued in U.S. Appl. No. 14/498,864.
U.S. Office Action dated May 18, 2018 issued in U.S. Appl. No. 14/498,864.
U.S. Final Office Action dated Dec. 13, 2018 issued in U.S. Appl. No. 14/498,864.
U.S. Office Action dated Aug. 1, 2019 issued U.S. Appl. No. 14/498,864.
Australian Examination Report dated Aug. 7, 2019 issued in AU 2014324669.
PCT International Search Report and Written Opinion dated Dec. 9, 2014 issued in PCT/US2014/057899.
PCT International Preliminary Report on Patentability and Written Opinion dated Apr. 7, 2016 issued in PCT/US2014/057899.

(Continued)

*Primary Examiner* — Michael L Borin
(74) *Attorney, Agent, or Firm* — Weaver Austin Villeneuve & Sampson LLP

(57) ABSTRACT

Disclosed are methods for building a sequence activity model with reference to structural data, which model can be used to guide directed evolution of proteins having beneficial properties. Some embodiments use genetic algorithms and structural data to filter out uninformative data. Some embodiments use a support vector machine to train the sequence activity model. The filtering and training methods can generate a sequence activity model having higher predictive power than conventional modeling methods. Systems and computer program products implementing the methods are also provided.

20 Claims, 8 Drawing Sheets

(56) References Cited

OTHER PUBLICATIONS

European Examination Report dated Jun. 12, 2017 issued in Application No. EP 14781426.3.
Extended European Search Report dated Sep. 20, 2018 issued in Application No. EP 18187438.9.
Japanese First Office Action dated Sep. 19, 2018 issued in Application No. JP 2016-516874.
Japanese Second Office Action dated Apr. 26, 2019 issued in Application No. JP 2016-516874.
Russian First Office Action dated Mar. 17, 2017 issued in Application No. RU 2016116253.
Russian Second Office Action dated Aug. 30, 2017 issued in Application No. RU 2016116253.
Russian Third Office Action dated Jan. 16, 2018 issued in Application No. RU 2016116253.
Russian Fourth Office Action dated Jul. 26, 2018 issued in Application No. RU 2016116253.
Russian Fifth Office Action dated Oct. 25, 2018 issued in Application No. RU 2016116253.
Singapore Written Opinion dated Jan. 20, 2017 issued in Application No. SG 11201601695W.
Singapore Second Written Opinion dated Oct. 25, 2017 issued in Application No. SG 11201601695W.
Chinese First Office Action dated Nov. 30, 2017 issued in Application No. CN 201480065215.X.
Chinese Second Office Action dated Sep. 26, 2018 issued in Application No. CN 201480065215.X.
Chinese Third Office Action dated May 22, 2019 issued in Application No. CN 201480065215.X.
Australian Examination Report dated Mar. 22, 2019 issued in Application No. AU 2014324670.
Chinese First Office Action dated Jan. 17, 2018 issued in Application No. CN 201480065176.3.
European First Office Action dated May 23, 2018 issued in Application No. EP 14786396.3.
European Office Action dated Oct. 25, 2018 issued in Application No. EP 14786396.3.
Israel First Office Action dated Jun. 30, 2019 issued in Application No. IL 244457.
PCT International Search Report and Written Opinion dated Jan. 23, 2015 issued in PCT/US2014/057900.
PCT International Preliminary Report on Patentability and Written Opinion dated Apr. 7, 2016 issued in PCT/US2014/057900.
Singapore Written Opinion dated Oct. 26, 2016 issued in Application No. SG 11201601692P.
Israel First Office Action dated Sep. 16, 2018 issued in Application No. IL 244458.
Japanese Office Action dated Jul. 26, 2017 issued in Application No. JP 2016-516871.
New Zealand First Examination Report dated Aug. 14, 2019 issued in Application No. NZ 717647.
Russian First Office Action dated Mar. 1, 2018 issued in Application No. RU 2016116261.
Russian Second Office Action dated Jul. 30, 2018 issued in Application No. RU 2016116261.
Russian Third Office Action dated Dec. 18, 2018 issued in Application No. RU 2016116261.
Chaparro-Riggers, et al. (2007) "Better library design: data-driven protein engineering," *Biotechnol. J.*, 2:180-191.
Ferreira P., et al. (2006) "Site-directed mutagenesis of selected residues at the active side of aryl-alcohol oxidase, an H2O2-producing ligninolytic enzyme," The FEBS Journal, vol. 273, No. 21, pp. 4878-4888.
Fox, et al. (2005) "Directed molecular evolution by machine learning and the influence of nonlinear interactions," *Journal of Theoretical Biology*, 234:187-199.
Fox, et al. (2007) "Improving catalytic function by ProSAR-driven enzyme evolution," *Nature Biotechnology*, 25(3):338-344.
Hecht, et al. (2011) "Applications of Machine Learning and Computational Intelligence to Drug Discovery and Development" Drug Development Research, vol. 72, pp. 53-65.
Hediger, et al. (2012) "A Computational Methodology to Screen Activities of Enzyme Variants," *PLOS One*, 7(12):10pp.
Hediger, et al. (Aug. 29, 2013) "In silico screening of 393 mutants facilitates enzyme engineering of amidase activity in CalB," *PeerJ*, vol. 1, 15pp [DOI 10.7717/peerj.145].
Hermann, et al. "Structure-based activity prediction for an enzyme of unknown function," Nature, vol. 448, No. 7155, Aug. 16, 2007, pp. 775-779.
Imberty, et al. "Molecular modelling of protein-carbohydrate interactions. Docking of monosaccharides in the binding site of concanavalin A," Glycobiology, vol. 1, No. 6, (1991) pp. 631-642. <doi:10.1093/glycob/1.6.631>.
Juhl, et al. "Modeling substrate specificity and enantioselectivity for lipases and esterases by substrate-imprinted docking," BMC Structural Biology, vol. 9, No. 39, Jun. 3, 2009, pp. 1-17. <doi:10.1186/1472-6807-9-39>.
Kuchner, et al. (Dec. 1997) "Directed evolution of enzyme catalysts," *Tibtech*, 15:523-530.
Mizutani, et al. "Efficient Method for High-Throughput Virtual Screening Based on Flexible Docking: Discovery of Novel Acetylcholinesterase Inhibitors," Journal of Medicinal Chemistry, vol. 47, No. 20, Aug. 28, 2004, pp. 4818-4828. <doi:10.1021/jm030605g>.
Murphy, et al. "An active role for machine learning in drug development" Nature Chemical Biology, vol. 7, Jun. 2011, pp. 327-330.
Ning, et al. (2011) "In Silico Structure-Activity-Relationship (SAR) Models From Machine Learning: A Review," Drug Development Research, vol. 72, pp. 138-146.
Schneidman-Duhovny, et al., "PatchDock and SymmDock: servers for rigid and symmetric docking," Nucleic Acids Research, vol. 33, (2005) pp. W363-W367. <doi:10.1093/nar/gki481>.
Sirin, et al. (2014) "A Computational Approach to Enzyme Design: Predicting co-Aminotransferase Catalytic Activity Using Docking and MM-GBSA Scoring," *Journal of Chemical Information and Modeling*, 54(8):2334-2346.
Sonawane, et al. "In Silico mutagenesis and docking studies of active site residues suggest altered substrate specificity and possible physiological role of Cinnamoyl CoA Reductase 1 (L1-CCRH1)," Bioinformation vol. 9, No. 5, Mar. 2, 2013, pp. 224-232. <ISSN 0973-2063>.
Trott, et al. "AutoDock Vina: improving the speed and accuracy of docking with a new scoring function, efficient optimization and multithreading," J. Comput. Chem., vol. 31, No. 2, Jan. 30, 2010, pp. 455-461. <doi:10.1002/jcc.21334>.
Vieth, et al. (1998) "Assessing Energy Functions for Flexible Docking," *Journal of Computational Chemistry*, 19(14):1612-1622.
Vieth, et al. (1998) "Assessing Search Strategies for Flexible Docking," *Journal of Computational Chemistry*, 19(14):1623-1631.
Vilar, et al. (2012) "Predicting Biological Activities through QSAR Analysis and Docking-based Scoring," Methods Mol. Biol., vol. 914, pp. 271-284. <doi:10.1007/978-1-62703-023-6 16>.
Wu, et al. (2003) "Detailed Analysis of Grid-Based Molecular Docking: A Case Study of CDOCKER-A CHARMm-Based MD Docking Algorithm," *Journal of Computational Chemistry*, 24(13):1549-1562.
Yang, et al. (2004) "GEMDOCK: A Generic Evolutionary Method for Molecular Docking," Proteins: Structure, Function, and Bioinformatics, vol. 55, pp. 288-304.
U.S. Office Action dated Jun. 20, 2016 issued in U.S. Appl. No. 14/498,881.
U.S. Final Office Action dated Nov. 18, 2016 issued in U.S. Appl. No. 14/498,881.
U.S. Office Action dated Dec. 14, 2017 issued in U.S. Appl. No. 14/498,881.
U.S. Final Office Action dated Jun. 19, 2018 issued in U.S. Appl. No. 14/498,881.
U.S. Office Action dated Aug. 1, 2019 issued U.S. Appl. No. 14/498,881.

(56) References Cited

OTHER PUBLICATIONS

Brazil First Office Action/Written Opinion dated Nov. 12, 2019 issued in Application No. BR 1120160062841.
Canadian First Examination Report dated Aug. 24, 2021 issued in CA 2,923,755.
Japanese Third Office Action dated Oct. 30, 2020 issued in Application No. JP 2016-516874.
Japanese Final Office Action [no-translation] dated Jan. 29, 2021 issued in Application No. JP 2018-237169.
Korean First Office Action dated Nov. 24, 2020 issued in Application No. KR 10-2016-7010661.
Korean Second Office Action dated May 25, 2021 issued in Application No. KR 10-2016-7010661.
Canadian Second Office Action dated Apr. 21, 2021 issued in Application No. CA 2,923,758.
Korean Second Office Action dated Mar. 23, 2021 issued in Application No. KR 10-2016-7010659.
Korean Notice of Allowance dated Sep. 14, 2021 issued in Application No. KR 10-2016-7010659.
David P. Nannemann et al., "Assessing directed evolution methods for the generation of biosynthetic enzymes with potential in drug biosynthesis" Future Med Chem. vol. 3, pp. 803-819 (May 2011).
Fang Zheng et al., "Computational Modeling of Solvent Effects on Protein-Ligand Interactions Using Fully Polarizable Continuum Model and Rational Drug Design" Commun. Comput. Phys. vol. 13 (Jan. 2013).
U.S. Notice of Allowance dated Apr. 9, 2020 issued in U.S. Appl. No. 14/498,864.
Brazil First Office Action and Written Opinion dated Mar. 17, 2020 issued in BR 1120160062850.
Japanese First Office Action dated Feb. 21, 2020 issued in Application No. JP 2018-237169.
New Zealand First Examination Report dated Mar. 12, 2020 issued in Application No. NZ 717658.
New Zealand Further Examination Report dated Mar. 17, 2020 issued in Application No. NZ 717647.
India First Office Action dated Jul. 8, 2020 issued in Application No. IN 201647013534.
New Zealand Second Examination Report dated Sep. 24, 2020 issued in Application No. NZ 717658.
Canadian First Office Action dated Jul. 23, 2020 issued in Application No. CA 2923758.
Indian First Office Action dated Jul. 11, 2020 issued in Application No. IN 201647013558.
Korean First Office Action dated Sep. 18, 2020 issued in Application No. KR 10-2016-7010659.

\* cited by examiner

| Variant | Activity | Sequence | | | Energy (kcal/mol) | | Geometry (Å) | | | | |
|---|---|---|---|---|---|---|---|---|---|---|---|
| | | P1 | P2 | P3 | Total | Interact | $N_1$ | P | $C_{(O)}$ | $C_{(H3)}$ | $O_{(H)}$ |
| 1 | 0.3 | A | C | E | 0.43 | 0.38 | 2.4 | 3.5 | 0.4 | 5.5 | 3.1 |
| 2 | 4.4 | F | G | I | -2.1 | -2.2 | 1.3 | 0.8 | 3.5 | 5.6 | 4.4 |
| 3 | 2.3 | K | L | N | -3.1 | -3.3 | 0.6 | 1.2 | 2.1 | 0.3 | 4.4 |
| 4 | 5.1 | P | Q | S | -5.2 | -5.6 | 0.3 | 0.7 | 1.1 | 3.1 | 2.1 |
| 5 | 1.3 | T | V | Y | 1.8 | 1.2 | 3.2 | 2.1 | 4.2 | 0.3 | 1.7 |
| ... | ... | ... | ... | ... | ... | ... | ... | ... | ... | ... | ... |
| n | 4.1 | X | D | H | -4.1 | -4.2 | 0.7 | 1.1 | 2.2 | 2.5 | 3.1 |

A. Raw Sequence Activity Data

| | | | | | 1 | 1 | 1 | 1 | 0 | 1 | 0 |
|---|---|---|---|---|---|---|---|---|---|---|---|
| Variant | Activity | Sequence | | | Energy (kcal/mol) | | Geometry (Å) | | | | |
| | | P1 | P2 | P3 | Total | Interact | $N_1$ | P | $C_{(O)}$ | $C_{(H3)}$ | $O_{(H)}$ |
| 1 | 0.3 | A | C | E | 0.43 | 0.38 | 2.4 | 3.5 | 0.4 | 5.5 | 3.1 |
| 2 | 4.4 | F | G | I | -2.1 | -2.2 | 1.3 | 0.8 | 3.5 | 5.6 | 4.4 |
| 3 | 2.3 | K | L | N | -3.1 | -3.3 | 0.6 | 1.2 | 2.1 | 0.3 | 4.4 |
| 4 | 5.1 | P | Q | S | -5.2 | -5.6 | 0.3 | 0.7 | 1.1 | 3.1 | 2.1 |
| 5 | 1.3 | T | V | Y | 1.8 | 1.2 | 3.2 | 2.1 | 4.2 | 0.3 | 1.7 |
| ... | ... | ... | ... | ... | ... | ... | ... | ... | ... | ... | ... |
| n | 4.1 | X | D | H | -4.1 | -4.2 | 0.7 | 1.1 | 2.2 | 2.5 | 3.1 |

B. Sequence Activity Data Filtering Columns of Data
(GA individual: E Toal=1, E Interact=1, $N_1$=1, P=1, $C_{(O)}$=0, $C_{(H3)}$=1, $O_{(H)}$=0)

| | Variant | Activity | Sequence | | | Energy (kcal/mol) | | Geometry (Å) | | | | |
|---|---|---|---|---|---|---|---|---|---|---|---|---|
| | | | P1 | P2 | P3 | Total | Interact | $N_1$ | P | $C_{(O)}$ | $C_{(H3)}$ | $O_{(H)}$ |
| P>2.8 | ~~1~~ | ~~0.3~~ | ~~A~~ | ~~C~~ | ~~E~~ | ~~0.43~~ | ~~0.38~~ | ~~2.4~~ | ~~3.5~~ | ~~0.4~~ | ~~5.5~~ | ~~3.1~~ |
| | 2 | 4.4 | F | G | I | -2.1 | -2.2 | 1.3 | 0.8 | 3.5 | 5.6 | 4.4 |
| | 3 | 2.3 | K | L | N | -3.1 | -3.3 | 0.6 | 1.2 | 2.1 | 0.3 | 4.4 |
| | 4 | 5.1 | P | Q | S | -5.2 | -5.6 | 0.3 | 0.7 | 1.1 | 3.1 | 2.1 |
| E Total>1.5 | ~~5~~ | ~~1.3~~ | ~~T~~ | ~~V~~ | ~~Y~~ | ~~1.8~~ | ~~1.2~~ | ~~3.2~~ | ~~2.1~~ | ~~4.2~~ | ~~0.3~~ | ~~1.7~~ |
| | ... | ... | ... | ... | ... | ... | ... | ... | ... | ... | ... | ... |
| | n | 4.1 | X | D | H | -4.1 | -4.2 | 0.7 | 1.1 | 2.2 | 2.5 | 3.1 |

C. Sequence Activity Data Filtering Rows of Data
(GA individual: E Toal>1.5, E Interact>1.5, $N_1$>3.3, P>2.8, $C_{(O)}$>3.6, $C_{(H3)}$>6, $O_{(H)}$>6)

*FIG. 2*

METHODS AND SYSTEMS FOR ENGINEERING BIOMOLECULES

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

Protein design has long been known to be a difficult task if for no other reason than the combinatorial explosion of possible molecules that constitute searchable sequence space. The sequence space of proteins is immense and is impossible to explore exhaustively using methods currently known in the art, which are often limited by the time and cost required to identify useful polypeptides. Part of the problem arises from the great number of polypeptide variants that must be sequenced, screened and assayed. Directed evolution methods increase the efficiency in honing in on the candidate biomolecules having advantageous properties. Today, directed evolution of proteins is dominated by various high throughput screening and recombination formats, often performed iteratively.

Various computational techniques have also been proposed for exploring sequence-activity space. Relatively speaking, these techniques are in their infancy and significant advances are still needed. Accordingly, new methods for improving the efficiency of screening, sequencing, and assaying candidate biomolecules are highly desirable.

SUMMARY

The present disclosure relates to the fields of molecular biology, molecular evolution, bioinformatics, and digital systems.

Methods of the present disclosure have utility in the optimization of proteins for industrial and therapeutic use. The methods and systems are especially useful for designing and developing enzymes having beneficial properties or activities.

Certain aspects of the present disclosure relate to methods for developing proteins having beneficial properties and/or guiding directed evolution programs. The disclosure presents methods for identifying bio-molecules with desired properties (or which are most suitable for directed evolution toward such properties) from complex bio-molecule libraries or sets of such libraries. Some embodiments of the present disclosure provide methods for building a sequence activity model with reference to structural data, which model can be used to guide directed evolution of proteins having beneficial properties. Some embodiments use genetic algorithm(s) and structural data to filter out uninformative data. Some embodiments use support vector machine(s) to train the sequence activity model. The filtering and training methods can generate a sequence activity model having higher predictive power than conventional modeling methods.

Some embodiments of the disclosure provide methods for conducting directed evolution. In some embodiments, the method is implemented using a computer system that includes one or more processors and system memory. The method includes: (a) receiving a data set having information from physical measurements of molecules, wherein the data set includes the following information for each of a plurality of variant biomolecules: (i) activity of the variant biomolecule on a ligand in a binding site of the variant biomolecule, (ii) a sequence of the variant biomolecule, and (iii) one or more geometric parameters characterizing the geometry of the ligand in the binding site; (b) filtering the data set to produce a filtered data subset by removing information for one or more of the variant biomolecules, wherein the filtering comprises testing the predictive power of sequence activity models trained with a plurality of selected data subsets, each selected data subset having information for a particular set of variant biomolecules removed from the data set of (a); and (c) training an improved sequence activity model using the filtered data subset. In some embodiments, the information for each of the plurality of variant biomolecules also includes (iv) an interaction energy characterizing the interaction of the ligand in the binding site. In some embodiments, variant biomolecules are enzymes.

In some embodiments, the improved sequence activity model is obtained by a support vector machine, a multiple linear regression, a principal component regression, a partial least square regression, or a neural network.

In some embodiments, filtering the data set involves removing at least one of the geometric parameters from the data set. In some embodiments, the filtering of the data set is performed with a genetic algorithm. In some embodiments, the genetic algorithm varies thresholds for removing information associated with the geometric parameters for one or more of the variant biomolecules.

In some embodiments, the method for directed evolution further involves applying the improved sequence activity model to identify one or more new biomolecule variants predicted by the improved sequence activity model to have activity meeting certain criteria. Each of the one or more new biomolecule variants has a sequence that differs from the sequences of the biomolecule variants providing information for the data set of (a). In some embodiments, applying the improved sequence activity model to identify one or more new biomolecule variants involves performing a genetic algorithm in which potential new biomolecule variants are evaluated using the improved sequence activity model as a fitness function.

In some embodiments, the method for directed evolution further involves assaying the new biomolecule variants for activity. In some embodiments, the method also involves measuring the activity of the variant biomolecules by an in vitro assay.

In some embodiments, the method further involves producing a structural model for each of the new biomolecule variants. The method also uses the structural models to generate geometric parameters for binding sites of the new biomolecule variants. The geometric parameters characterize the geometry of the ligand in the binding sites of the new biomolecule variants. In some embodiments, the method further involves receiving structural models of biomolecule variants and determining the one or more geometric parameters using the structural models. In some embodiments, the structural models are homology models. In some embodiments, the homology models are prepared using physical structural measurement details of biomolecules. The physical structural measurement details of biomolecules may include three-dimensional positions of atoms obtained by NMR or x-ray crystallography.

In some embodiments, the method further involves using a docker to determine the one or more geometric parameters.

In some embodiments, the method also uses a docker to determine the interaction energy In some embodiments, the variant biomolecules processed are a plurality of enzymes. In some embodiments, the activity of the variant biomolecule on a ligand is the activity of an enzyme on a substrate. In some embodiments, the activity of an enzyme on a substrate includes one or more features of a catalytic conversion of the substrate by the enzyme.

In some embodiments, the method for directed evolution also involves using the improved sequence activity model to identifying one or more biomolecules having desired activity. In some embodiments, the method further includes synthesizing the biomolecules having desired activity.

In some embodiments, computer program products and computer systems implementing the methods for directed evolution of biomolecules are also provided.

These and other features will be presented below with reference to the associated drawings.

BRIEF DESCRIPTION OF THE DRAWINGS

FIG. 2 shows three tabular representations of a sequence activity data set to illustrate an example of filtering data according to some embodiments of the current disclosure.

DETAILED DESCRIPTION

Figure 1A:
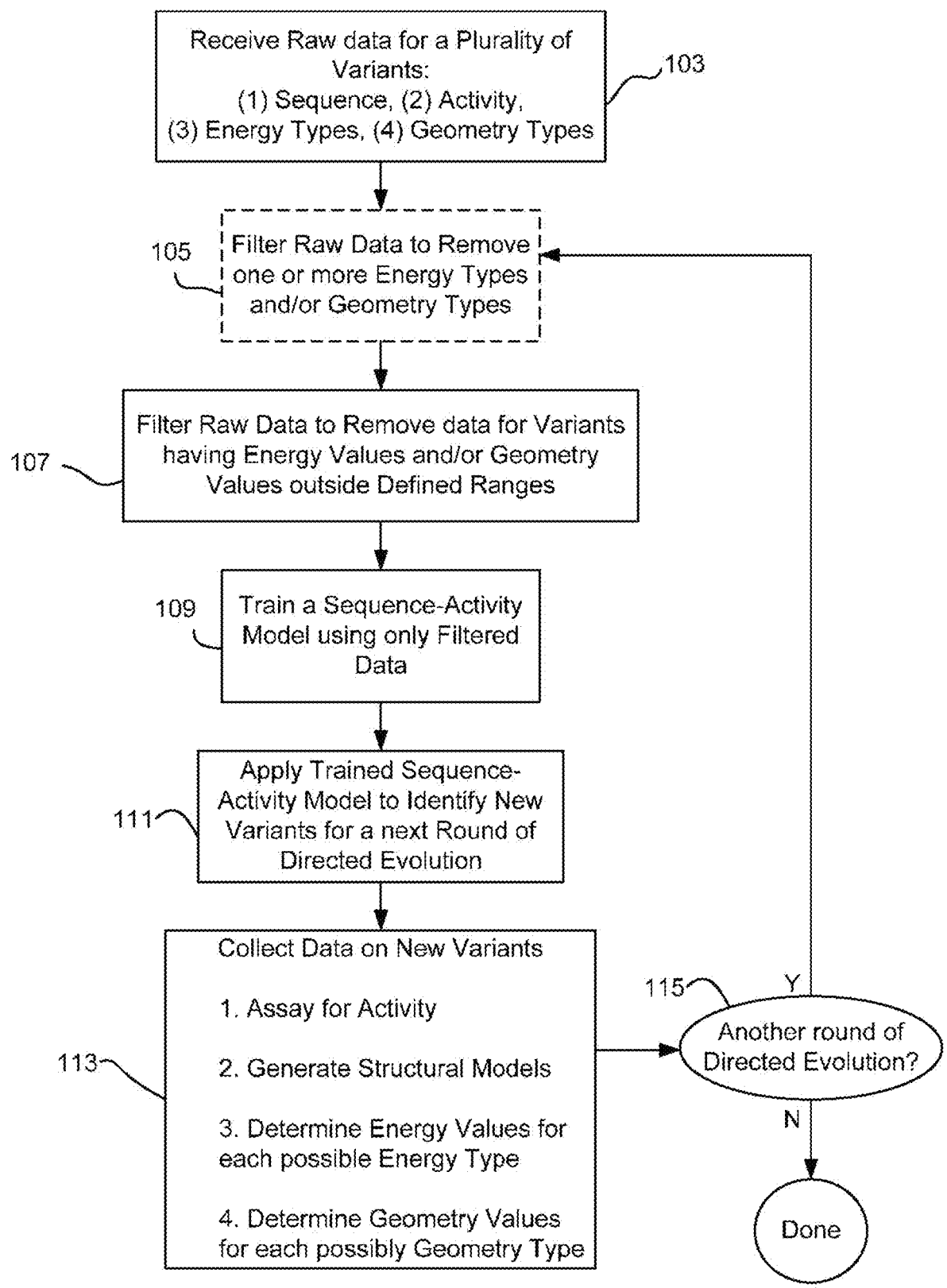
FIG. 1A is a flowchart depicting a directed evolution workflow according to some embodiments of the disclosure.

Methods for developing sequence activity models with reference to structural data are disclosed herein. The sequence activity models can be used to guide directed evolution of proteins having beneficial properties. Some embodiments can help to explore a large sequence space and quickly hone in on molecules of beneficial properties. Materials and/or resources may also be saved in the processes to find or develop proteins of desired properties. Some embodiments are especially useful for designing and developing enzymes having desired activity and/or selectivity for catalytic reactions involving particular substrates.

I. Definitions

Unless defined otherwise herein, all technical and scientific terms used herein have the same meaning as commonly understood by one of ordinary skill in the art. Various scientific dictionaries that include the terms included herein are well known and available to those in the art. Any methods and materials similar or equivalent to those described herein find use in the practice of the embodiments disclosed herein.

The terms defined immediately below are more fully understood by reference to the specification as a whole. The definitions are provided for the purpose of describing particular embodiments only and aiding in understanding the complex concepts described in this specification. They are not intended to limit the full scope of the disclosure. Specifically, it is to be understood that this disclosure is not limited to the particular sequences, compositions, algorithms, systems, methodologies, protocols, and/or reagents described herein, as these may vary, depending upon the context they are used by those of skill in the art.

As used in this specification and appended claims, the singular forms "a", "an", and "the" include plural referents unless the content and context clearly dictates otherwise. Thus, for example, reference to "a device" includes a combination of two or more such devices, and the like. Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected).

Support vector machines (SVMs) are machine learning tools with associated learning algorithms for classification and regression analysis. The basic SVM takes a set of input data and predicts, for each given input, which of two possible classes forms the output. Given a set of training examples, each marked as belonging to one of two categories, an SVM training algorithm builds a model that assigns new examples into one category or the other. An SVM is a representation of the examples as points in space, mapped so that the examples of the separate categories are divided by a clear gap that is as wide as possible, which is implemented by maximizing the distance between data points and a hyperplane separating the two categories. In addition to performing linear classification, SVMs can efficiently perform a non-linear classification using a kernel trick to implicitly map inputs into high-dimensional feature spaces.

When used for optimizing sequence activity models, SVM takes as inputs training sets of sequences that have been classified into two or more groups based on activity. Support vector machines operate by weighting different members of a training set differently depending upon how close they are to a hyperplane interface separating "active" and "inactive" members of the training set. This technique requires that the scientist first decide which training set members to place in the active group and which training set members to place in the inactive group. This may be accomplished by choosing an appropriate numerical value of activity to serve as the boundary between active and inactive members of the training set. From this classification, the support vector machine will generate a vector, W, that can provide coefficient values for individual ones of the independent variables defining the sequences of the active and inactive group members in the training set. These coefficients can be used to "rank" individual residues as described elsewhere herein. The technique attempts to identify a hyperplane that maximizes the distance between the closest training set members on opposite sides of that plane. In another variation, support vector regression modeling is carried out. In this case, the dependent variable is a vector of continuous activity values. The support vector regression model will generate a coefficient vector, W, which can be used to rank individual residues.

SVMs have been used to look at large data sets in many studies and have been quite popular in the DNA microarray field. Their potential strengths include the ability to finely discriminate (by weighting) which factors separate samples from each other. To the extent that an SVM can tease out precisely which residues contribute to function, it can be a particularly useful tool for ranking residues in accordance with this invention. SVMs are described in S. Gunn (1998) "Support Vector Machines for Classification and Regressions," Technical Report, Faculty of Engineering and Applied Science, Department of Electronics and Computer Science, University of Southampton, which is incorporated herein by reference for all purposes.

Docker (docking software or docking program)—A "docker" is a computer program that computationally predicts whether or not a ligand will bind or dock with a binding site of interest in a protein or other biological molecule. The process by which a ligand approaches and ultimately binds to the binding site is sometimes referred to "docking". The concept of docking may be understood as an interaction that causes the ligand to bind with the biomolecule in such a manner that the ligand is not easily dislodged. In successful docking, the ligand and biomolecule form a stable complex. A docked ligand may act as an agonist or antagonist. A docker may simulate and/or characterize the docking.

Dockers are typically implemented as software that may be temporarily or permanently stored in association with hardware such as a processor or processors. Commercially available docking programs include CDocker (Accelrys), DOCK (University of California, San Francisco), AutoDock (Scripps Research Institute), FlexX (tripos.com), GOLD (ccdc.cam.ac.uk), and GLIDE (schrodinger.com).

Various dockers output a docking score or other measure of binding between the ligand and the biomolecule. For some ligand-biomolecule combinations, the docking program will determine that binding is unlikely to occur. In such cases, the docking program will output a conclusion that the ligand does not bind with biomolecule.

Dockers may generate "poses" of ligands with respect to binding sites. Some of these poses may be used in generating a docking score or otherwise assessing docking. In some embodiments, the docker permits a user to specify a number of poses (n) to use in assessing docking. Only the top "n" poses with the best docking scores are considered in assessing docking.

A docker may be programmed to output an assessment of the likelihood that a ligand will dock with the binding site of biomolecule or the quality of such docking, should it occur. At one level, a docker determines whether a ligand is likely to bind to a biomolecule binding site. If the docker logic concludes that binding is not likely or is highly unfavorable, it may output a "no refined poses found" result. This may occur when all of the conformations the docking program generated have unfavorable van der Waals clashes and/or electrostatic repulsions with the binding site. In the above example of a docking procedure, if the second operation fails to find a pose with soft energy less than the threshold, the docker may return a result such as "no refined poses found." Because soft energy primarily considers nonbonded interactions including van der Waals and electrostatic forces, the no refined poses found result means the ligand has severe steric clashes and/or electrostatic repulsions with the biomolecule receptor for a given number of poses.

In certain embodiments, the docker outputs a docking score that represents the interaction between the ligand and the biomolecule binding site. Dockers may calculate various features of the ligand-biomolecule interaction. In one example, the output is simply the interaction energy between the ligand and the biomolecule. In another embodiment, a total energy is output. The total energy may be understood to be a combination of ligand-biomolecule interaction energy and ligand strain. In certain implementations, such energy may be calculated using a force field such as CHARMm.

In various embodiments, docking programs generate such outputs by considering multiple poses of the ligand in the binding site of the biomolecule. Each pose will have its own associated energy values. In some embodiments, the docking program ranks the poses and considers the energy associated with one or more of the high-ranking poses. In some cases, it may average the energies of certain high-ranking poses or otherwise perform a statistical analysis of the top ranking poses. In other embodiments, it simply chooses the value associated with the top-ranked pose and outputs this as the resulting energy for the docking.

A "pose" is the position or orientation of a ligand with respect to a binding site of a biological molecule. In a pose, the three dimensional positions of some or all atoms of the ligand are specified with respect to some or all of the positions of the atoms in the binding site. While a ligand's conformation is not its pose—because the conformation does not consider the binding site—the conformation can be used in determining a pose. In some embodiments, a ligand's orientation and conformation together define a pose. In some embodiments, a pose only exists if a ligand's orientation/conformation combination meets a defined threshold energy level in the reference binding site.

Various computational mechanisms can be employed to generate poses for docking. Examples include systematic or stochastic torsional searches about rotatable bonds, molecular dynamics simulations, and genetic algorithms to "evolve" new low energy conformations. These techniques are used to modify computational representations of the ligand and/or binding site to explore "pose space."

Dockers evaluate poses to determine how the ligand interacts with the binding site. In some embodiments, they do this by calculating energy of interaction based on one or more of the interaction types mentioned above (e.g., van der Waals forces). This information is used to characterize docking and in some cases produce a docking score. In some implementations, dockers rank poses based on docking score. In some implementations, dockers remove poses with unfavorable docking scores from consideration.

In certain embodiments, a virtual protein screening system evaluates a pose to determine whether the pose is active. A pose is deemed to be active if it meets defined constraints known to be important for the desired activity under consideration. As an example, the virtual protein screening system may determine whether a pose supports catalytic transformation of the ligand in a binding site.

A "ligand" is a molecule or complex that interacts with a binding site of a biomolecule to form a stable complex containing at least the ligand and biomolecule. In addition to the ligand and biomolecule, the stable complex may include (sometimes require) other chemical entities such as organic and inorganic cofactors (e.g., coenzymes and prosthetic groups), metal ions, and the like. Ligands may be agonists or antagonists.

When the biomolecule is an enzyme, the binding site is a catalytic site and the ligand is a substrate, a reaction intermediate of the substrate, or a transition state of the substrate. A "reaction intermediate" is a chemical entity generated from the substrate in the transformation from substrate to reaction product. A "transition state" of a substrate is the substrate in a state corresponding to the highest potential energy along a reaction pathway. At a transition state that tends to have a fleeting existence, colliding reactant molecules proceed to form products. In this disclosure, sometimes when a substrate is described in a process, the intermediate and transition state may also be suitable for the process. In such situations, the substrate, intermediate, and transition state may collectively be referred to as "ligands." In some cases, multiple intermediates are generated in the catalytic transformation of a substrate. In certain embodiments, the ligand species (substrate or intermediate or transition state) chosen for analysis is one known to be associated with a rate limiting step in the catalytic transformation. As an example, a substrate covalently bound to an enzyme cofactor may be chemically modified in a rate limiting step. In such case, the substrate-cofactor species is used in modeling the interaction.

As should be clear, the concept of a ligand is more general than the concept of a "substrate." Some ligands bind with a binding site but do not undergo a catalytic transformation. Examples include ligands evaluated in the drug design field. Such ligands may be small molecules chosen for their ability to non-covalently bind with a target biomolecule for pharmacological purposes. In some cases, a ligand is evaluated for its ability to potentiate, activate, or inhibit the natural behavior of a biomolecule.

As used herein, "biomolecule" and "biological molecule" refer to a molecule that is generally found in a biological organism. In some embodiments, biological molecules comprise polymeric biological macromolecules having multiple subunits (i.e., "biopolymers"). Typical biomolecules include, but are not limited to, molecules that share some structural features with naturally occurring polymers such as RNAs (formed from nucleotide subunits), DNAs (formed from nucleotide subunits), and peptides or polypeptides (formed from amino acid subunits), including, e.g., RNAs, RNA analogues, DNAs, DNA analogues, polypeptides, polypeptide analogues, peptide nucleic acids (PNAs), combinations of RNA and DNA (e.g., chimeraplasts), or the like. It is not intended that biomolecules be limited to any particular molecule, as any suitable biological molecule finds use in the present disclosure, including but not limited to, e.g., lipids, carbohydrates, or other organic molecules that are made by one or more genetically encodable molecules (e.g., one or more enzymes or enzyme pathways) or the like. Of particular interest for some aspects of this disclosure are biomolecules having binding sites that interact with a ligand to effect a chemical or biological transformation, e.g., catalysis of a substrate, activation of biomolecule, or inactivation of the biomolecule.

In some embodiments, a "beneficial property" or "activity" is an increase or decrease in one or more of the following: catalytic rate ($k_{cat}$), substrate binding affinity ($K_M$), catalytic efficiency ($k_{cat}/K_M$), substrate specificity, chemoselectivity, regioselectivity, stereoselectivity, stereospecificity, ligand specificity, receptor agonism, receptor antagonism, conversion of a cofactor, oxygen stability, protein expression level, solubility, thermoactivity, thermostability, pH activity, pH stability (e.g., at alkaline or acidic pH), glucose inhibition, and/or resistance to inhibitors (e.g., acetic acid, lectins, tannic acids and phenolic compounds), and proteases. Other desired activities may include an altered profile in response to a particular stimulus; e.g., altered temperature and/or pH profiles. In the context of rational ligand design, optimization of targeted covalent inhibition (TCI) is a type of activity. In some embodiments, two or more variants screened as described herein act on the same substrate but differ with respect to one or more of the following activities: rate of product formation, percent conversion of a substrate to a product, selectivity, and/or percent conversion of a cofactor. It is not intended that the present disclosure be limited to any particular beneficial property and/or desired activity.

In some embodiments, "activity" is used to describe the more limited concept of an enzyme's ability to catalyze the turnover of a substrate to a product. A related enzyme characteristic is its "selectivity" for a particular product such as an enantiomer or regioselective product. The broad definition of "activity" presented herein includes selectivity, although conventionally selectivity is sometimes viewed as distinct from enzyme activity.

The terms "protein," "polypeptide" and "peptide" are used interchangeably to denote a polymer of at least two amino acids covalently linked by an amide bond, regardless of length or post-translational modification (e.g., glycosylation, phosphorylation, lipidation, myristilation, ubiquitination, etc.). In some cases, the polymer has at least about 30 amino acid residues, and usually at least about 50 amino acid residues. More typically, they contain at least about 100 amino acid residues. It is not intended that the present invention be limited to amino acid sequences of any specific length. The terms include compositions conventionally considered to be fragments of full-length proteins or peptides. Included within this definition are D- and L-amino acids, and mixtures of D- and L-amino acids. The polypeptides described herein are not restricted to the genetically encoded amino acids. Indeed, in addition to the genetically encoded amino acids, the polypeptides described herein may be made up of, either in whole or in part, naturally-occurring and/or synthetic non-encoded amino acids. In some embodiments, a polypeptide is a portion of the full-length ancestral or parental polypeptide, containing amino acid additions or deletions (e.g., gaps), and/or substitutions as compared to the amino acid sequence of the full-length parental polypeptide, while still retaining functional activity (e.g., catalytic activity).

As used herein, the term "wild-type" or "wildtype" (WT) refers to naturally-occurring organisms, enzymes and/or other proteins (e.g., non-recombinant enzymes). A substrate or ligand that reacts with a wild-type biomolecule is sometimes considered a "native" substrate or ligand.

As used herein, the terms "variant," "mutant," "mutant sequence," and "variant sequence" refer to a biological sequence that differs in some respect from a standard or reference sequence (e.g., in some embodiments, a parental sequence). The difference may be referred to as a "mutation". In some embodiments, a mutant is a polypeptide or polynucleotide sequence that has been altered by at least one substitution, insertion, cross-over, deletion, and/or other genetic operation. For purposes of the present disclosure, mutants and variants are not limited to a particular method by which they are generated. In some embodiments, a mutant or variant sequence has increased, decreased, or substantially similar activities or properties, in comparison to the parental sequence. In some embodiments, the variant polypeptide comprises one or more amino acid residues that have been mutated, as compared to the amino acid sequence of the wild-type polypeptide (e.g., a parent polypeptide). In some embodiments, one or more amino acid residues of the polypeptide are held constant, are invariant, or are not mutated as compared to a parent polypeptide in the variant polypeptides making up a plurality of polypeptides. In some embodiments, the parent polypeptide is used as the basis for generating variants with improved stability, activity, or any other desired property.

As used herein, the terms "enzyme variant" and "variant enzyme" are used in reference to enzymes that are similar to a reference enzyme, particularly in their function, but have mutations in their amino acid sequence that make them different in sequence from the wild-type or another reference enzyme. Enzyme variants can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. After the variants are produced, they can be screened for the desired property (e.g., high or increased; or low or reduced activity, increased thermal and/or alkaline stability, etc.).

A "panel of enzymes" is a group of enzymes selected such that each member of the panel catalyzes the same chemical reaction. In some embodiments, the members of the panel can collectively turn over multiple substrates, each undergoing the same reaction. Often the panel members are chosen to efficiently turn over multiple substrates. In some cases, the panels are commercially available. In other cases, they are proprietary to an entity. For example, a panel may include various enzymes identified as hits in a screening procedure. In certain embodiments, one or more members of a panel exist only as a computational representation. In other words, the enzyme is a virtual enzyme.

A "model" is a representation of the structure of a biomolecule or ligand. It is sometimes provided as a collection of three-dimensional positions for the atoms or moieties of the entity being represented. Models often contain computationally-produced representations of the binding sites or other aspects of the enzyme variants. Examples of models relevant to the embodiments herein are produced from homology modeling, protein threading, or ab initio protein modeling using a routine such as Rosetta (rosettacommons.org/software/) or Molecular Dynamics simulations.

A "homology model" is a three dimensional model of a protein or portion of a protein containing at least the binding site of a ligand under consideration. Homology modeling relies on the observation that protein structures tend to be conserved amongst homologous proteins. A homology model provides three dimensional positions of residues including backbone and side chains. The model is generated from a structure template of a homologous protein likely to resemble the structure of the modeled sequence. In some embodiments, a structure template is used in two steps: "align sequence to templates" and "build homology models".

The "align sequence to templates" step aligns the model sequence to one or more structure template sequences and prepares an input sequence alignment for building the homology model. The alignment identifies gaps and other regions of dissimilarity between the model sequence and the structure template sequence(s).

The "building homology models" step uses structural features of the structure template to derive spatial restraints which, in turn, are used to generate, e.g., model protein structures using conjugate gradient and simulated annealing optimization procedures. The structural features of the template may be obtained from a technique such as NMR or x-ray crystallography. Examples of such techniques can be found in the review article, "A Guide to Template Based Structure Prediction," by Qu X, Swanson R, Day R, Tsai J. Curr Protein Pept Sci. 2009 June; 10(3):270-85.

The term "active conformation" is used in reference to a conformation of a protein (e.g., an enzyme) that allows the protein to cause a substrate to undergo a chemical transformation (e.g., a catalytic reaction).

An "active pose" is one in which a ligand is likely to undergo a catalytic transformation or perform some desired role such as covalently binding with the binding site.

The term "sequence" is used herein to refer to the order and identity of any biological sequences including but not limited to a whole genome, whole chromosome, chromosome segment, collection of gene sequences for interacting genes, gene, nucleic acid sequence, protein, peptide, polypeptide, polysaccharide, etc. In some contexts, a "sequence" refers to the order and identity of amino acid residues in a protein (i.e., a protein sequence or protein character string) or to the order and identity of nucleotides in a nucleic acid (i.e., a nucleic acid sequence or nucleic acid character string). A sequence may be represented by a character string. A "nucleic acid sequence" refers to the order and identity of the nucleotides comprising a nucleic acid. A "protein sequence" refers to the order and identity of the amino acids comprising a protein or peptide.

"Codon" refers to a specific sequence of three consecutive nucleotides that is part of the genetic code and that specifies a particular amino acid in a protein or starts or stops protein synthesis.

The term "gene" is used broadly to refer to any segment of DNA or other nucleic acid associated with a biological function. Thus, genes include coding sequences and optionally, the regulatory sequences required for their expression. Genes also optionally include non-expressed nucleic acid segments that, for example, form recognition sequences for other proteins. Genes can be obtained from a variety of sources, including cloning from a source of interest or synthesizing from known or predicted sequence information, and may include sequences designed to have desired parameters.

A "moiety" is a part of a molecule that may include either whole functional groups or parts of functional groups as substructures, while functional groups are groups of atoms or bonds within molecules that are responsible for the characteristic chemical reactions of those molecules.

"Screening" refers to the process in which one or more properties of one or more bio-molecules are determined. For example, typical screening processes include those in which one or more properties of one or more members of one or more libraries are determined.

Screening can be performed computationally using computational models of biomolecules and virtual environment of the biomolecules. In some embodiments, virtual protein screening systems are provided for selected enzymes of desired activity and selectivity.

An "expression system" is a system for expressing a protein or peptide encoded by a gene or other nucleic acid.

"Directed evolution," "guided evolution," or "artificial evolution" refers to in silico, in vitro, or in vivo processes of artificially changing one or more biomolecule sequences (or a character string representing that sequence) by artificial selection, mutation, recombination, or other manipulation. In some embodiments, directed evolution occurs in a reproductive population in which (1) there are varieties of individuals, (2) some varieties having heritable genetic information, and (3) some varieties differ in fitness. Reproductive success is determined by outcome of selection for a predetermined property such as a beneficial property. The reproductive population can be, e.g., a physical population in an in vitro process or a virtual population in a computer system in an in silico process.

Directed evolution methods can be readily applied to polynucleotides to generate variant libraries that can be expressed, screened, and assayed. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237: 1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391: 288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In certain embodiments, directed evolution methods generate protein variant libraries by recombining genes encoding variants developed from a parent protein, as well as by recombining genes encoding variants in a parent protein variant library. The methods may employ oligonucleotides containing sequences or subsequences encoding at least one protein of a parental variant library. Some of the oligonucleotides of the parental variant library may be closely related, differing only in the choice of codons for alternate amino acids selected to be varied by recombination with other variants. The method may be performed for one or multiple cycles until desired results are achieved. If multiple cycles are used, each typically involves a screening step to identify those variants that have acceptable or improved performance and are candidates for use in at least one subsequent recombination cycle. In some embodiments, the screening step involves a virtual protein screening system for determining the catalytic activity and selectivity of enzymes for desired substrates.

In some embodiments, directed evolution methods generate protein variants by sited directed mutagenesis at defined residues. These defined residues are typically identified by structural analysis of binding sites, quantum chemistry analysis, sequence homology analysis, sequence activity models, etc. Some embodiments employ saturation mutagenesis, in which one tries to generate all possible (or as close to as possible) mutations at a specific site, or narrow region of a gene.

"Shuffling" and "gene shuffling" are types of directed evolution methods that recombine a collection of fragments of the parental polynucleotides through a series of chain extension cycles. In certain embodiments, one or more of the chain extension cycles is self-priming; i.e., performed without the addition of primers other than the fragments themselves. Each cycle involves annealing single stranded fragments through hybridization, subsequent elongation of annealed fragments through chain extension, and denaturing. Over the course of shuffling, a growing nucleic acid strand is typically exposed to multiple different annealing partners in a process sometimes referred to as "template switching," which involves switching one nucleic acid domain from one nucleic acid with a second domain from a second nucleic acid (i.e., the first and second nucleic acids serve as templates in the shuffling procedure).

Template switching frequently produces chimeric sequences, which result from the introduction of crossovers between fragments of different origins. The crossovers are created through template switched recombinations during the multiple cycles of annealing, extension, and denaturing. Thus, shuffling typically leads to production of variant polynucleotide sequences. In some embodiments, the variant sequences comprise, a "library" of variants (i.e., a group comprising multiple variants). In some embodiments of these libraries, the variants contain sequence segments from two or more of parent polynucleotides.

When two or more parental polynucleotides are employed, the individual parental polynucleotides are sufficiently homologous that fragments from different parents hybridize under the annealing conditions employed in the shuffling cycles. In some embodiments, the shuffling permits recombination of parent polynucleotides having relatively limited/low homology levels. Often, the individual parent polynucleotides have distinct and/or unique domains and/or other sequence characteristics of interest. When using parent polynucleotides having distinct sequence characteristics, shuffling can produce highly diverse variant polynucleotides.

Various shuffling techniques are known in the art. See e.g., U.S. Pat. Nos. 6,917,882, 7,776,598, 8,029,988, 7,024, 312, and 7,795,030, all of which are incorporated herein by reference in their entireties.

Some directed evolution techniques employ "Gene Splicing by Overlap Extension" or "gene SOEing," which is a PCR-based method of recombining DNA sequences without reliance on restriction sites and of directly generating mutated DNA fragments in vitro. In some implementations of the technique, initial PCRs generate overlapping gene segments that are used as template DNA for a second PCR to create a full-length product. Internal PCR primers generate overlapping, complementary 3' ends on intermediate segments and introduce nucleotide substitutions, insertions or deletions for gene splicing. Overlapping strands of these intermediate segments hybridize at 3' region in the second PCR and are extended to generate the full-length product. In various applications, the full length product is amplified by flanking primers that can include restriction enzyme sites for inserting the product into an expression vector for cloning purposes. See, e.g., Horton, et al., Biotechniques, 8(5): 528-35 [1990]. "Mutagenesis" is the process of introducing at least one mutation into a standard or reference sequence such as a parent nucleic acid or parent polypeptide.

Site directed mutagenesis is one example of a useful technique for introducing mutations, although any suitable method finds use. Thus, alternatively or in addition, the mutants may be provided by gene synthesis, saturating random mutagenesis, semi-synthetic combinatorial libraries of residues, recursive sequence recombination ("RSR") (See e.g., US Patent Application Publ. No. 2006/0223143, incorporated by reference herein in its entirety), gene shuffling, error-prone PCR, and/or any other suitable method.

One example of a suitable saturation mutagenesis procedure is described in US Patent Application Publ. No. 2010/0093560, which is incorporated herein by reference in its entirety.

A "fragment" is any portion of a sequence of nucleotides or amino acids. Fragments may be produced using any suitable method known in the art, including but not limited to cleaving a polypeptide or polynucleotide sequence. In some embodiments, fragments are produced by using nucleases that cleave polynucleotides. In some additional embodiments, fragments are generated using chemical and/or biological synthesis techniques. In some embodiments, fragments comprise subsequences of at least one parental sequence, generated using partial chain elongation of complementary nucleic acid(s). In some embodiments involving in silico techniques, virtual fragments are generated computationally to mimic the results of fragments generated by chemical and/or biological techniques. In some embodiments, polypeptide fragments exhibit the activity of the full-length polypeptide, while in some other embodiments, the polypeptide fragments do not have the activity exhibited by the full-length polypeptide.

"Parental polypeptide," "parental polynucleotide," "parent nucleic acid," and "parent" are generally used to refer to the wild-type polypeptide, wild-type polynucleotide, or a variant used as a starting point in a diversity generation procedure such as a directed evolution. In some embodiments, the parent itself is produced via shuffling or other diversity generation procedure(s). In some embodiments, mutants used in directed evolution are directly related to a parent polypeptide. In some embodiments, the parent polypeptide is stable when exposed to extremes of temperature, pH and/or solvent conditions and can serve as the basis for generating variants for shuffling. In some embodiments, the parental polypeptide is not stable to extremes of temperature, pH and/or solvent conditions, and the parental polypeptide is evolved to make a robust variants.

A "parent nucleic acid" encodes a parental polypeptide.

A "library" or "population" refers to a collection of at least two different molecules, character strings, and/or models, such as nucleic acid sequences (e.g., genes, oligonucleotides, etc.) or expression products (e.g., enzymes or other proteins) therefrom. A library or population generally includes a number of different molecules. For example, a library or population typically includes at least about 10 different molecules. Large libraries typically include at least about 100 different molecules, more typically at least about 1000 different molecules. For some applications, the library includes at least about 10000 or more different molecules. However, it is not intended that the present invention be limited to a specific number of different molecules. In certain embodiments, the library contains a number variant or chimeric nucleic acids or proteins produced by a directed evolution procedure.

Two nucleic acids are "recombined" when sequences from each of the two nucleic acids are combined to produce progeny nucleic acid(s). Two sequences are "directly" recombined when both of the nucleic acids are substrates for recombination.

The term "selection" refers to the process in which one or more bio-molecules are identified as having one or more properties of interest. Thus, for example, one can screen a library to determine one or more properties of one or more library members. If one or more of the library members is/are identified as possessing a property of interest, it is selected. Selection can include the isolation of a library member, but this is not necessary. Further, selection and screening can be, and often are, simultaneous. Some embodiments disclosed herein provide systems and methods for screening and selecting enzymes of desirable activity and/or selectivity.

"Next-generation sequencing" and "high-throughput sequencing" are sequencing techniques that parallelize the sequencing process, producing thousands or millions of sequences at once. Examples of suitable next-generation sequencing methods include, but are not limited to, single molecule real-time sequencing (e.g., Pacific Biosciences, Menlo Park, Calif.), ion semiconductor sequencing (e.g., Ion Torrent, South San Francisco, Calif.), pyrosequencing (e.g., 454, Branford, Conn.), sequencing by ligation (e.g., SOLiD sequencing of Life Technologies, Carlsbad, Calif.), sequencing by synthesis and reversible terminator (e.g., Illumina, San Diego, Calif.), nucleic acid imaging technologies such as transmission electron microscopy, and the like.

A "dependent variable" ("DV") represents an output or effect, or is tested to see if it is the effect. The "independent variables" ("IVs") represent the inputs or causes, or are tested to see if they are the cause. A dependent variable may be studied to see if and how much it varies as the independent variables vary.

In the simple stochastic linear model $$y_i = a + bx_i + e_i$$

where the term $y_i$ is the $i^{th}$ value of the dependent variable and $x_i$ is $i^{th}$ value of the independent variable (IV). The term $e_i$ is known as the "error" and contains the variability of the dependent variable not explained by the independent variable.

An independent variable (IV) is also known as a "predictor variable", "regressor", "controlled variable", "manipulated variable", "explanatory variable", or "input variable".

The term "coefficient" refers to a scalar value multiplied by a dependent variable or an expression containing a dependent variable.

The terms "orthogonal" and "orthogonality" refer to an independent variable that is uncorrelated with other independent variables in a model or other relationship.

The term "sequence activity model" refers to any mathematical models that describe the relationship between activities, characteristics, or properties of biological molecules on the one hand, and various biological sequences on the other hand.

The term "character string" refers to a representation of a biological molecule that preserves sequence/structural information regarding that molecule. In some embodiments, the character string contains information about sequence mutations in a library of variants. Character strings of bio-molecules and activity information for the bio-molecules may be used as a training set for a sequence activity model. Non-sequence properties of bio-molecules can be stored or otherwise associated with character strings for the bio-molecules.

A "reference sequence" is a sequence from which variation of sequence is effected. In some cases, a "reference sequence" is used to define the variations. Such sequence may be one predicted by a model to have the highest value (or one of the highest values) of the desired activity. In another case, the reference sequence may be that of a member of an original protein variant library. It certain embodiments, a reference sequence is the sequence of a parent protein or nucleic acid.

The phrase "training set" refers to a set of sequence-activity data or observations that one or more models are fitted to and built upon. For instance, for a protein sequence activity model, a training set comprises residue sequences for an initial or improved protein variant library. Typically, these data include complete or partial residue sequence information, together with an activity value for each protein in the library. In some cases, multiple types of activities (e.g., rate constant data and thermal stability data) are provided together in the training set. The activity is sometimes a beneficial property.

The term "observation" is information about protein or other biological entity that may be used in a training set for generating a model such as a sequence activity model. The term "observation" may refer to any sequenced and/or assayed biological molecules, including protein variants. In certain embodiments, each observation is an activity value and an associated sequence for a variant in a library. Generally, the more observations employed to create a sequence activity model, the better the predictive power of that sequence activity model.

The phrase "predictive power" refers to the ability of a model to correctly predict the values of a dependent variable for data under various conditions. For example, the predictive power of a sequence activity model refers to the ability of the model to predict activity from sequence information.

The phrase "cross validation" refers to a method for testing the generalizability of a model's ability to predict the value of the dependent variable. The method prepares a model using one set of data, and tests the model error using a different set of data. The first set of data is viewed as a training set, and the second set of data is a validation set.

The phrase "systematic variance" refers to different descriptors of an item or set of items being changed in different combinations.

The phrase "systematically varied data" refers to data produced, derived, or resulting from different descriptors of an item or set of items being changed in different combinations. Many different descriptors can be changed at the same time, but in different combinations. For example, activity data gathered from polypeptides in which combinations of amino acids have been changed is systematically varied data.

The phrase "systematically varied sequences" refers to a set of sequences in which each residue is seen in multiple contexts. In principle, the level of systematic variation can be quantified by the degree to which the sequences are orthogonal from one another (i.e., maximally different compared to the mean).

The term "toggling" refers to the introduction of multiple amino acid residue types into a specific position in the sequences of protein variants in the optimized library.

The terms "regression" and "regression analysis" refer to techniques used to understand which of the independent variables are related to the dependent variable, and to explore the forms of these relationships. In restricted circumstances, regression analysis can be used to infer causal relationships between the independent and dependent variables. It is a statistical technique for estimating the relationships among variables. It includes many techniques for modeling and analyzing several variables, when the focus is on the relationship between a dependent variable and one or more independent variables. More specifically, regression analysis helps one understand how the typical value of the dependent variable changes when any one of the independent variables is varied, while the other independent variables are held fixed. Regression techniques may be used to generate sequence activity models from training sets comprising multiple observations, which may contain sequence and activity information.

"Partial Least Squares" ("PLS") is a family of methods that finds a linear regression model by projecting predicted variables (e.g., activities) and the observable variables (e.g., sequences) to a new space. PLS is also known as "projection to latent structures." Both the X (independent variables) and Y (dependent variables) data are projected to new spaces. PLS is used to find the fundamental relations between two matrices (X and Y). A latent variable model is used to model the covariance structures in the X and Y spaces. A PLS model will try to find the multi-dimensional direction in the X space that explains the maximum multi-dimensional variance direction in the Y space. PLS regression is particularly useful when the matrix of predictors has more variables than observations, and when there is multi-collinearity among X values.

Latent variables (as opposed to observable variables) are variables that are not directly observed but are inferred from observed or directly measured variables. Mathematical models that aim to explain observed variables in terms of latent variables are called latent variable models.

A "descriptor" refers to something that serves to describe or identify an item. For example, characters in a character string can be descriptors of amino acids in a polypeptide being represented by the character string.

In a regression model, the dependent variable is related to independent variables by a sum of terms. Each term includes a product of an independent variable and an associated regression coefficient. In the case of a purely linear regression model, the regression coefficients are given by $\beta$ in the following form of expression:

$$y_i = \beta_1 x_{i1} + \ldots + \beta_p x_{ip} + \varepsilon_i = x_i^T \beta + \varepsilon_i$$

where $y_i$ is the dependent variable, the $x_i$ are the independent variables, $\varepsilon_i$ is the error variable, and T denotes the transpose, that is the inner product of the vectors $x_i$ and $\beta$.

The phrase "principal component regression" ("PCR") refers to a regression analysis that uses principal component analysis when estimating regression coefficients. Instead of regressing the dependent variable on the independent variables directly, the principal components of the independent variables are used. PCR typically only uses a subset of the principal components in the regression analysis.

The phrase "principal component analysis" ("PCA") refers to a mathematical procedure that uses an orthogonal transformation to convert a set of observations of possibly correlated variables into a set of values of linearly uncorrelated variables called "principal components." The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it be orthogonal to (i.e., uncorrelated with) the preceding components.

A "neural network" is a model containing an interconnected group of processing elements or "neurons" that process information using a connectionist approach to computation. Neural networks are used to model complex relationships between inputs and outputs and/or to find patterns in data. Most neural networks process data in a non-linear, distributed, parallel fashion. In most cases, neural networks are adaptive systems that change their structure during a learning phase. Functions are performed collectively and in parallel by the processing elements, rather than using a clear delineation of subtasks to which various units are assigned.

Generally, a neural network involves a network of simple processing elements that exhibit complex global behavior determined by the connections between the processing elements and element parameters. Neural networks are used with algorithms designed to alter the strength of the connections in the network to produce a desired signal flow. The strength is altered during training or learning.

A "genetic algorithm" ("GA") is a process that mimics evolutionary processes. Genetic algorithms (GAs) are used in a wide variety of fields to solve problems which are not fully characterized or too complex to allow full characterization, but for which some analytical evaluation is available. That is, GAs are used to solve problems that can be evaluated by some quantifiable measure for the relative value of a solution (or at least the relative value of one potential solution in comparison to another). In the context of the present disclosure, a genetic algorithm is a process for selecting or manipulating character strings in a computer, typically where the character string corresponds to one or more biological molecules (e.g., nucleic acids, proteins, or the like) or data used to train a model such as a sequence activity model or a support vector machine.

In one example, a genetic algorithm provides and evaluates a population of models in a first generation of the algorithm. Each model includes multiple parameters describing the relationship between at least one independent variable (IV) and a dependent variable (DV). A "fitness function" evaluates the member models of the population and ranks them based on one or more criteria such as high desired activity or low model prediction error. The member models of the population are also sometimes referred to as individuals or chromosomes in the context of genetic algorithms. In some embodiments, model fitness are evaluated using Akaike Information Criterion (AIC) or Bayesian Information Criterion (BIC), wherein individuals having the smallest AIC or BIC values are chosen as the fittest individuals. High ranking models are selected for promotion to a second generation and/or mating to produce a population of "children models" for a second generation of the algorithm. The population in the second generation is similarly evaluated by the fitness function, and high ranking members are promoted and/or mated as with the first generation. The genetic algorithm continues in this manner for subsequent generations until a "convergence criterion" is met, at which point the algorithm concludes with one or more high ranking individuals (models).

In another example, the "individuals" are variant peptide sequences and the fitness function is the predicted activity of these individuals. Each generation contains a population of individual peptide sequences, with are evaluated for fitness. The fittest in a generation are selected for promotion and/or mating to produce a next generation population. After multiple generations, the genetic algorithm may converge to a population of high-performing peptide sequences.

As in the example above, a genetic algorithm often runs through multiple iterations to search for optimal parameters in a parameter space. Each iteration of the genetic algorithm is also referred to as a "generation" of the genetic algorithm. The models in a generation of the genetic algorithm form a "population" for the generation. In the context of genetic algorithms, the terms "chromosome" and "individual" are sometimes used as aliases for a model or a set of model parameters in a population. It is so used because a model from a parent generation passes its parameters (or "genes") onto the models of a child generation, which resembles the biological process that a parent chromosome passing its genes down to a child chromosome.

The term "genetic operation" ("GO") refers to biological and/or computational genetic operations, wherein all changes in any population of any type of character strings (and thus in any physical properties of physical objects encoded by such strings) can be described as a result of random and/or predetermined application of a finite set of logical algebraic functions. Examples of GO include but are not limited to multiplication, crossover, recombination, mutation, ligation, fragmentation, etc.

The "Akaike Information Criterion" ("AIC") is a measure of the relative goodness of fit of a statistical model, and it is often used as a criterion for model selection among a finite set of models. The AIC is grounded in the concept of information entropy, in effect offering a relative measure of the information lost when a given model is used to describe reality. It can be said to describe the tradeoff between bias and variance in model construction, or loosely speaking between accuracy and complexity of the model. The AIC can be calculated as:

$$AIC = -2 \log_e L + 2k,$$

wherein L is the maximum likelihood of the function and k is the number of free parameters of the model to be estimated.

The "Bayesian Information Criterion" ("BIC") is a criterion for model selection among a finite set of models, and is closely related to AIC. The BIC can be calculated as:

$$BIC = -2 \log_e L + k \log_e(n),$$

wherein n is the number of data observations. As the number of observations increased, BIC often penalizes an extra number of free parameters more heavily than AIC.

A "likelihood function" or "likelihood" of a model is a function of the parameters of a statistical model. The likelihood of a set of parameter values given some observed outcomes equals to the probability of those observed outcomes given those parameter values, i.e., $L(\theta|x) = P(x|\theta)$.

An "ensemble model" is a model whose terms include all the terms of a group of models, wherein the ensemble model's coefficients of the terms are based on the weighted coefficients of the corresponding terms of the individual models of the group. The weighting of coefficients is based on the predictive power and/or fitness of the individual models.

"Monte Carlo simulations" are simulations that rely on a large number of random samplings to obtain numerical results that simulate a real phenomenon. For instance, drawing a large number of pseudo-random uniform variables from the interval (0,1], and assigning values less than or equal to 0.50 as heads and greater than 0.50 as tails, is a Monte Carlo simulation of the behavior of repeatedly tossing a coin.

II. General Descriptions of Workflow

A. Workflow for a Round of Directed Evolution

In certain embodiments, the overall workflow makes use of both in vitro and computational techniques for controlling a directed evolution process. The computational side of the process employs structural models and sequence activity models.

Each round of directed evolution employs a new set of structural models and a new sequence activity model. Further, in each round, biomolecule variants identified for further analysis are evaluated using three-dimensional structural models of the variants. Information from the structural models is combined with the variants' sequences and assay data (activity) to generate a large unfiltered data set. Typically, a portion of the data set is used as a training set. For the current round of directed evolution, the training set trains a sequence activity model, which then identifies biomolecule variants for the next round of directed evolution.

In certain embodiments, one or more genetic algorithms (GAs) are employed to evaluate the combined unfiltered data provided at the beginning of each round of directed evolution. The GAs identify a subset of the information contained in the unfiltered data set, which subset is used as independent variables for training a new sequence activity model. Activity is the dependent variable; the sequence activity model provides activity as a function of independent variables identified during the filtering. In various embodiments, the sequence activity model is a non-linear model. In certain embodiments, the sequence activity model is a hyperplane in an n-dimensional space, which may be generated by a support vector machine.

In an example depicted in FIG. 1A, a directed evolution workflow unfolds as follows. Initially, information is collected for multiple biomolecule variants. Each of these variants may have been identified in a previous round of directed evolution. If the project is just beginning (i.e., there are no previous rounds of directed evolution), the variants are obtained from a different source such as a panel of biomolecules known to have potentially interesting properties. Sometimes, the variants of the first round are chosen to span a relatively wide range of sequence and/or activity space.

After the variants have been identified, an evaluation system obtains various types of information for each variant. Notably, at least one activity of interest and the sequence of each variant are determined. In some embodiments, the sequence is represented as a collection of mutations from the wild-type sequence or other reference sequence. In some embodiments, the activity is stored as a numerical value having defined units. In some embodiments, the activity values are normalized. If the sequence of a given variant is not known, it may be obtained by sequencing a physical sample of the variant.

In addition to the sequence activity data, a structural model is generated for each variant biomolecule. In certain embodiments, the structural models are homology models. The structural models are evaluated computationally to obtain additional data that are combined with the sequence and activity data for each variant. In some implementations, each variant's structural model is used to identify an interaction energy of a ligand with the biomolecule's receptor site and/or one or more parameters describing the geometry of the ligand in the receptor site. Such geometry may include distances between atoms of the ligand and atoms of a residue moiety in the binding site and/or atoms of a cofactor moiety in the binding site. Certain examples are presented below.

The unfiltered data set includes sequence and activity data for each variant and typically includes a variety of additional pieces of information for each variant. As described herein, these additional pieces of information are derived from the structural models for each variant. Further, these additional data typically include (i) interaction or binding energies between the ligand under consideration and the binding site of each variant and/or (ii) structural/geometric descriptors characterizing the interaction of the ligand with the receptor. See block 103 of FIG. 1A.

It has been found that the raw unfiltered set of data is not always optimal for training a new sequence activity model. Rather, a filtered subset of the combined raw data set typically provides a more useful sequence activity model. Therefore the raw data set from block 103 is filtered as illustrated in blocks 105 and 107.

Filtering may be accomplished by any suitable technique(s). As described more fully below, one optional technique removes certain types of parameters obtained from the structural models of the variants (e.g., certain substrate atom to residue atom distances). Block 105. As an example, the unfiltered data set may contain ten available geometric characteristics of the ligand in the receptor binding site, but filtering eliminates three of these, so that a subset of only seven such parameters is used in the training set. These parameters, along with sequence, serve as independent variables in a sequence activity model trained on the training set. Alternatively or additionally, filtering may remove variants having values of one or more of the independent variables that fall outside a range or below a threshold determined to be useful for producing the sequence activity model. Block 107. In certain embodiments, the independent variables filtered in this manner are derived from the structural model.

As illustrated at a block 109, after the raw data set is properly filtered, it is used to generate the sequence activity model. As mentioned, the sequence activity model may be a non-linear model such as a hyperplane in an n-dimensional space determined by a support vector machine. After the sequence activity model is generated, it is used to help identify high-performing variants for a next round of directed evolution. See block 111. In one embodiment, the trained sequence activity model is used with a genetic algorithm (GA) to select a plurality of variant sequences likely to have beneficial properties. The selected variants are used in the next round of directed evolution. In such next round, the variants selected with the sequence activity model are treated as described above (blocks 103, optionally 105, 107, and 109). However, they are first analyzed to produce a new raw data set. See block 113. In certain embodiments, the variants are physically produced and assayed for activity. This provides some of the raw data. The variants are also structurally modeled to determine interaction energy values and ligand binding geometry values for each of the energy types and geometry types used in an earlier round of directed evolution. A docker may be employed to generate values for these data types. If necessary, one or more of the variants are sequenced to complete the raw data.

Rounds of directed evolution continue in this manner until one or more rounds show limited improvement or meet other convergence criteria. The directed evolution project is then concluded. In FIG. 1A, the convergence criteria check is illustrated by a decision block 115.

B. Model Generation Workflow

As indicated above, some implementations filter a raw data set prior to training a sequence activity model. The filtering may remove certain variable types from the raw data. Each variable type is a potential independent variable for the sequence activity model. Alternatively, or in addition, the filtering may remove certain variants having parameter values outside defined ranges. It has been found that such filtering reduces the noise produced by models trained using the data. In some implementations, the filtering is accomplished using one or more GAs. In certain embodiments, the types of data filtered from raw data are limited to interaction energy between the ligand and a biomolecule and/or geometric characteristics of the ligand in the biomolecule binding site.

Figure 1B:
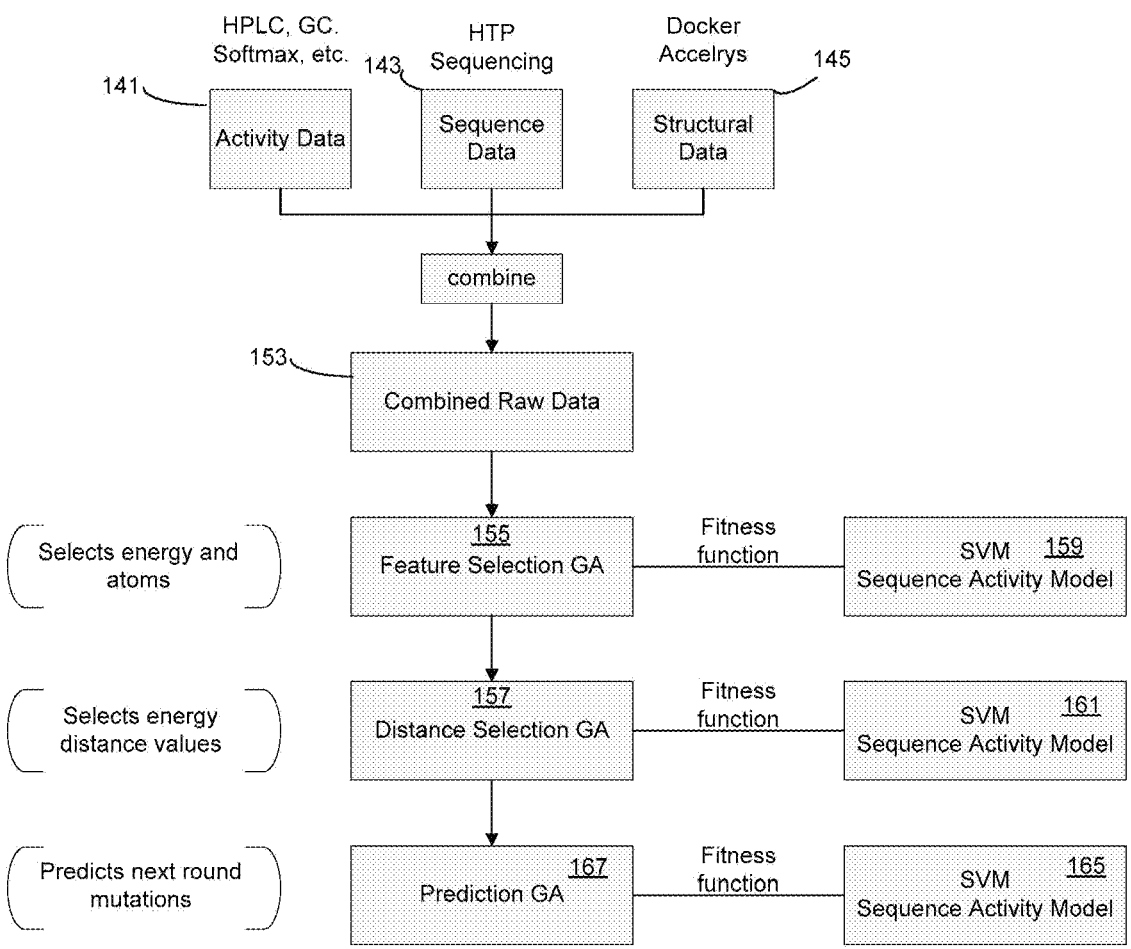
FIG. 1B is a flowchart illustrating one approach to filtering raw data according to some embodiments of the disclosure.

FIG. 1B presents one approach to filtering raw data. In the depicted embodiment, data from three sources are combined to form a raw data set 153. Each variant contributes its own data from all three sources. The combined data includes activity data for a ligand-variant interaction. The activity data, which is represented by a block 141, may be generated using standard assaying tools such as liquid chromatography, gas chromatography, etc. In addition, sequence data are provided for the individual variants that have the desired activity data (block 141). Sequence data, which are represented by block 143, may be known ahead of time or may be determined by sequencing the variants' amino acids or encoding nucleic acids. Sequencing may be performed using any one of many available sequencing technologies. Massively parallel sequencing is used in some embodiments. Finally, structural data may be generated from structural models of the variants. Such information may be obtained using not only the structural models but a docking program (docker) which evaluates ligand poses in the binding site of the structural model of a variant under consideration. The raw structural data contains data for many types of parameters including particular interaction energy types and atom-to-atom distances between ligands and cofactors and/or binding site residues. The raw structural data is represented by block 145 in FIG. 1B.

All three sources of data are combined as depicted in FIG. 1B to provide the combined raw data 153. In certain embodiments, the combined raw data are provided in the form of a computer readable file or group of files that are available for further processing by a filtering tool or computer-implemented algorithm.

In the depicted embodiment, two separate stages of filtering are shown: feature selection in stage 155 and distance selection in stage 157. In the depicted embodiment, each of these filtering operations is accomplished using its own genetic algorithm employing its own sequence activity model as an objective function. In a specific embodiment, the sequence activity models are generated using support vector machines 159 and 161, as depicted in FIG. 1B. The feature selection filter identifies particular interaction energy types and/or atom-to-atom distances for removal from the combined raw data set. In this embodiment, the concept of "distance" includes other geometric parameters such as angular, torsional, and overall positional characteristics of ligand atoms with respect to biomolecule and/or cofactor atoms. The identified data types are removed for all variants contributing to the data set. When using a genetic algorithm, the removal process may be fluid. In other words, one or more of the removed data types may be removed only temporarily, for one or more generations, during performance of the feature selection genetic algorithm. Examples of suitable techniques for accomplishing this are described below. The distance selection filter removes data for certain variants that contribute to the raw data. This filter selects certain energy and/or distance values that are outside designated numerical ranges. Any variant having energy and/or distance values outside of these ranges has its data entirely removed from the raw data set. When the filtering is implemented using a genetic algorithm, variant data removed at one point in the process may be reintroduced, if appropriate, during later execution of the genetic algorithm. For example, variant data removed during one generation of the genetic algorithm may be reintroduced in a later generation. The process will be described in more detail below.

After the filtering is concluded as described with respect to blocks 155 and 157, a sequence activity model is trained using the filtered data. In some implementations, the training is carried out using a support vector machine. The resulting sequence activity model is depicted as block 165. It is used as an objective function in a different genetic algorithm, which considers and ranks variant sequences based on predicted activity values. The genetic algorithm in question is depicted in block 167 of FIG. 1B.

In some other embodiments, feature selection stage 155 is not performed. Therefore, no feature is filtered out. In other words, all available features are used in training the sequence activity model 165 for the prediction genetic algorithm 167. Filtering only removes variants having energy or geometry values outside identified ranges. In some other embodiments, the feature selection stage 155, and distance selection stage 157, are combined into a single selection stage, which may be implemented using a genetic algorithm. In these embodiments, feature types and feature values are both varied in the training set data evaluated using a genetic algorithm.

Figure 1C:
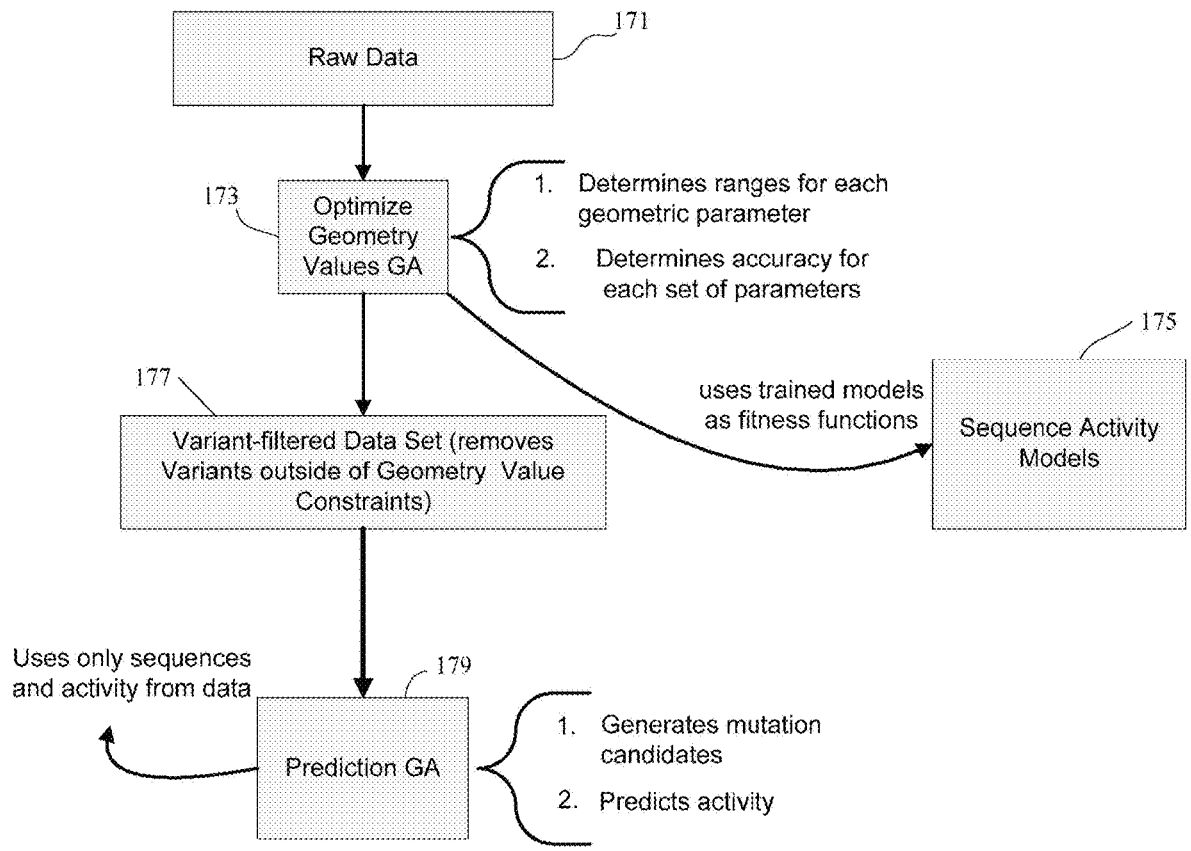
FIG. 1C is a flowchart presenting a data filtering process according to some embodiments, in which the feature selection stage is not performed or is combined with the distance selection stage.

FIG. 1C presents a process in which the feature selection stage is not performed or is combined with the distance selection stage 157. As shown, raw data 171 are filtered using a single genetic algorithm 173, which selects variants having one or more geometry parameters constrained within chosen ranges. In one example, the geometry parameters are distances between atoms of a substrate and atoms of a residue or cofactor in a binding site. For example, one parameter may be a distance between nitrogen atom on cofactor and an oxygen atom on a tyrosine residue in a binding site, another parameter maybe a distance between a carbonyl carbon on a substrate and a phosphorus atom on the cofactor, and so on. Each of these distances may be set within arbitrary thresholds (e.g., the first distance may need to be less than 5 angstroms and the second distance may need to be less than 7.5 angstroms).

The fitness function of the algorithm 173 is the predictive accuracy of sequence activity models 175 trained using different combinations of parameter constraints. In this manner, various combinations of constrained geometry parameters are evaluated for their ability to train accurate sequence activity models 175. In certain embodiments, the sequence activity models are trained using support vector machines.

Variants that are not selected by genetic algorithm 173 are removed from consideration to produce variant-filtered data set 177. In other words, the result of filtering by single genetic algorithm 173 is a subset of the raw data 171 containing only data for a subset of the variants in data 171. This subset is used to train a highly accurate sequence activity model that is in turn used in another genetic algorithm, a prediction algorithm 179. In certain embodiments, the prediction algorithm 179 identifies new variant sequences predicted to have high activity. It may do this by applying alternative amino acid (or nucleotide) sequences to the trained sequence activity model and determining which ones are likely to have high values for a beneficial property (e.g., the activity of the sequence activity model). The genetic algorithm 179 generates alternative sequences, which the trained sequence activity model evaluates for fitness. Ultimately, high performing variant sequences are identified for further investigation and/or production.

III. General Description of Genetic Algorithm Applications

Some embodiments provide methods of using genetic algorithms to generate a filtered data set for training a sequence activity model such as one optimized by a support vector machine (e.g., the first and second genetic algorithms described below). Other embodiments provide methods of using genetic algorithms to adjust the values of the coefficients of sequence activity models in order to fit the models to the filtered training data set. Yet other embodiments use genetic algorithm to explore sequence space and identify protein variants having advantageous properties (e.g., the third genetic algorithm described below).

In a genetic algorithm, an appropriate fitness function and an appropriate mating procedure are defined. The fitness function provides a criterion for determining which "individuals" (models in some embodiments) are "most fit" with regard to the observed data or have the highest predictive power (i.e., the models are likely to provide the best results). In some embodiments, a model is defined by a relation between one or more independent variables (IVs) and a dependent variable (DV), and the relationship is described by one or more parameters. The genetic algorithm provides a mechanism to search through parameter spaces to find the combinations of parameters or ranges of parameter values that generate the most successful models.

Many processes in genetic algorithms are inspired by biological genetic operations. As such, terms used in genetic algorithms are borrowed from biological terms regarding genetic operations. In these embodiments, each of the "individuals" (sometimes referred to as members, or chromosomes) of a population includes "genes" representing all the parameters being tested for a model, and the genes having chosen values in defined ranges for the parameters. For instance, a chromosome can have a gene representing the presence of Gly at position 131.

In some embodiments, genetic algorithm may be used to select appropriate IVs for the models (e.g., the first genetic algorithm described below for column filtering). One example of such an algorithm includes genes/parameters of binary value 1 and 0, each parameter associated with one IV. If a parameter converges to 0 for an IV among the fittest individuals at the end of the algorithm, that IV is dropped from the model. That term is preserved conversely.

In some embodiments, the fitness of a model is measured by the predictive power of the model. In some embodiments, the fitness is measured by hit rates based on a confusion matrix described below. In some embodiments, the fitness is measured by AIC or BIC. The models in this example may in some cases actually be the underlying data sets used to produce those models.

After each "model" in a particular generation is evaluated for its predictive power, the genetic algorithm is checked for convergence or other criteria (such as a fixed number of generations) to determine if the process should continue for a further generation. Assuming that the genetic algorithm has not yet met the criterion to stop, the models of the current generation are ranked. Those that have the highest predictive power may be preserved and used in the next generation. For example, an elitism rate of 10% may be employed. In other words, the top 10% of models (as determined using the fitting function and measured by, e.g., accuracy or AIC) are set aside to become members of the next generation. The remaining 90% of the members in the next generation are obtained by mating "parents" from the previous generation.

As indicated, the "parents" are models selected from the previous generation. Generally, the selection is weighted toward more fit members of the previous generation, although there may be a random component in their selection. For example, the parent models may be selected using a linear weighting (e.g., a model that performs 1.2 times better than another model is 20% more likely to be selected) or a geometric weighting (i.e., the predictive differences in models are raised to a power in order to obtain a probability of selection). In some embodiments, the parents are selected by simply choosing the best performing two or more models from the ranking of models in the previous generation and no other models are selected. In these embodiments, all selected models from the prior generation are mated. In other embodiments, some models from the prior generation are selected for inclusion in the next generation model without mating, and other poorer performing models from the prior generation are randomly selected as parents. These parents may be mated with each other and/or with the better performing models selected for inclusion as such in the next generation.

After a set of parent models has been selected, pairs of such models are mated to produce children models by providing some genes (parameter values) from one parent and other genes (parameter values) from the other parent. In one approach, the coefficients of the two parents are aligned and each value is considered in succession to determine whether the child should take the term from parent A or from parent B. In one implementation, the mating process begins with parent A and randomly determines whether a "crossover" event should occur at the first term encountered. If so, the term is taken from parent B. If not, the term is taken from parent A. The next term in succession is considered for crossover, etc. The terms continue to come from the parent donating the previous term under consideration until a cross over event occurs. At that point, the next term is donated from the other parent and all successive terms are donated from that parent until another crossover event occurs. To ensure that the same term is not selected at two different locations in the child model, various techniques may be employed, e.g., a partially matched crossover technique. In some embodiments, instead of using the values of the genes from either parent, the average of the values of the gene may be adopted for a child chromosome.

In some embodiments, a genetic algorithm also employs one or more mutation mechanisms to generate further diversity of the models, which helps to explore regions of a parameter space that are not covered by any existing genes in the parent generation. On the flip side, mutation mechanisms affect convergence, such that the higher the mutation rate or the larger the mutation range, the longer it will take to converge (if ever). In some embodiments, mutation is implemented by random selection of a chromosome/model, and a random selection of a parameter/gene of said chromosome, which is then randomly changed. In some embodiments, the randomly changed values of parameters/genes are drawn from a random uniform distribution with a defined range. In other embodiments, the randomly changed values of parameters/genes are drawn from a random normal distribution with a defined range.

After each parameter has been considered, a child "model" is defined for the next generation. Then another two parents can be chosen to produce another child model, and so on. Eventually, the children population in a new generation is ready for evaluation by the fitness function in manners described above.

The process continues generation-by-generation until meeting a stop criterion such as convergence of values. At that point, at least one of the top ranked models is selected from the current generation as the overall best model. Convergence can be tested by many conventional techniques. In some embodiments, it involves determining that the performance of the best model from a number of successive generations does not change appreciably. Examples of stop criteria include but are not limited to the number of generations generated so far, the activity of the top proteins from the current library, the magnitude of activity desired, and the level of improvement observed in last generation of models.

IV. Embodiments Using Genetic Algorithms for Data Filtering

In some embodiments, there are two or three stages for obtaining and using a sequence activity model from available information. Each of these steps uses a genetic algorithm. In a three-stage process, a first genetic algorithm operates on data from a raw data set to select independent variables for use in a sequence activity model. These independent variables are selected from the pool of available independent variables (sometimes called parameters). Not all available independent variables are used in the final model. In one embodiment, sequence or mutation information is always used as an independent variable, but other types of independent variable are selected by a genetic algorithm. A particular combination of independent variables that does a very good job (or, in some embodiments, the best job) of accurately predicting activity is selected. As an example, there may be five to ten available independent variables to use in addition to sequence information, but only three of these non-sequence variables are selected for use in a sequence activity model. A genetic algorithm identifies which of the many alternative combinations of independent variables does the best job of training a sequence activity model to predict activity.

Another genetic algorithm identifies suitable ranges of some or all of the non-sequence independent variables in the data set. The ranges may be defined by thresholds or cutoff values for the independent variables. This genetic algorithm is used in both two and three stage processes.

A final genetic algorithm identifies biomolecule (e.g., protein variant) sequences that are deserving of selection or further analysis. This genetic algorithm provides various sequences and tests their fitness using a sequence activity model trained using filtered data selected using the one or two preceding genetic algorithms. It is worth noting a difference between this genetic algorithm and other genetic algorithms discussed herein. This algorithm provides nucleic acid, amino acid, or other biomolecule sequences as individuals in a population. In contrast, in other genetic algorithm discussed herein, the individuals are models or sets of model parameters.

In some embodiments, the sequence activity model is a non-linear model. In other embodiments, it is a linear model.

As illustrated in FIG. 2 the data available for a sequence activity model training set includes information for each of multiple variant biomolecules used to prepare the training set. The information for each variant includes its sequence and its activity. In various examples presented herein, activity is the rate and/or stereoselectivity of an enzyme biomolecule in turning over a substrate. Other types of activity or beneficial property may be employed and some of these types are described elsewhere herein. The activity data are determined from in vitro analysis and/or a computation technique such as virtual screening described in U.S. patent application Ser. No. 14/498,864 [attorney docket no. CDXSP020], which is incorporated herein by reference in its entirety.

In certain embodiments, the sequence information may be provided as a group of mutations to a starting backbone, which backbone may be a wild-type sequence or some other sequence such as a consensus sequence. The sequence information regarding mutations may be presented in the form of the starting residue and the substitute residue at a given position. Another alternative simply identifies the ending residue at a particular position. In various embodiments, the sequence information is provided by a genetic algorithm or other computational technique and therefore is known without the need to sequence a nucleic acid or other composition. If sequencing is required, any of many types of sequencing may be employed. Some of these types are described elsewhere herein. For example, in some embodiments, high throughput techniques for sequencing nucleic acids are used.

In addition to sequence and activity data, the raw data contains various types of additional information that may be incorporated, or not, in the final training set for the sequence activity model. The additional information may be of many different types. Each type potentially serves as an independent variable for a sequence activity model. As explained herein, a genetic algorithm or other technique evaluates the usefulness of each type of information.

In various embodiments, the additional information describes characteristics of the ligand-receptor binding. Such information may be derived from measurements and/or computation. As mentioned, structural models of variants may identify values for these other types of information. In one example, the structural model is a homology model. A docker or similar tool may be used to obtain the additional information from the structural model. Examples of information generated from a docker include interaction energies and/or total energies as calculated by a docking program such as the Accelrys CDocker program. Other examples concern geometric parameters characterizing the relative position of the ligand or its active moieties or atoms with respect to a cofactor, binding site residue, and/or other feature associated with the binding site of the variant under consideration. As mentioned, some this information may concern distances, angles, and or torsional information about the relative positions of the substrate or intermediate and a cofactor or residue in the binding site. As examples, interaction energy values may be based on van der Waals force and/or electrostatics interaction. The internal energy of the ligand may also be considered.

FIG. 2A-2C illustrates an example of filtering a raw sequence activity data set according to some embodiments of the current disclosure. FIG. 2A shows a raw sequence activity data set for n variants of a family of transaminase. Each variant is associated with activity data, sequence data, energy data, and geometry data. In some embodiments, the activity data may be catalytic rate, enantiospecificity, etc., which may be assayed by various methods described elsewhere herein. Three sequence positions for each variant, P1, P2, and P3, are provided in the raw data set for inclusion in the sequence activity model. Furthermore, two energy values, the total energy and the interaction energy as determined by a virtual docking system elsewhere herein are provided for potential inclusion in the model. Finally, five geometry values are provided by a virtual docking system for potential inclusion in the model. In this example involving a ligand, each of these geometry values is the distance between a key atom of the ligand when docked into the enzyme variant versus when docked into the wild-type enzyme. Specifically, $N_1$ denotes a nitrogen atom, P being a phosphorus of a phosphate group, $C_{(O)}$ being the carbon atom of a carboxyl group, $C_{(H3)}$ being the carbon atom of a methyl group, and $O_{(H)}$ being the oxygen atom of a hydroxyl group.

According to some embodiments, the raw sequence activity data can be filtered by a genetic algorithm to exclude columns of data that are uninformative for training a sequence activity model of high predictive power. FIG. 2B shows an example of columns of data being filtered by a genetic algorithm. In this implementation, the genetic algorithm generates a population of individuals, each individual having a set of binary-valued "genes" or coefficients (e.g., 0 and 1) indicating whether the energy and geometry values should be included in the sequence activity model. The example in FIG. 2B shows the effect of an individual of a population of the GA, the individual having the following parameters: E Total=1, E Interact=1, $N_1$=1, P=1, $C_{(O)}$=0, $C_{(H3)}$=1, $O_{(H)}$=0. As a parameter takes on the value of 0, the feature associated with the parameter is effectively excluded from the model. This GA individual filters out the geometry data $C_{(O)}$ and $O_{(H)}$, thereby providing a subset of data for training a sequence activity model. In some embodiments, a sequence activity model is trained using the subset of data including three sequence IVs, two energy IVs, and three geometry IVs. Note that the binary valued coefficients or genes of the GA may be implemented separately from the sequence activity model, such that the sequence activity model does not include the coefficient values. In some embodiments, the sequence activity model is optimized using an SVM, which outputs hits and misses for predicted activity. The fitness function of the GA determined for each individual is based on the accuracy of the prediction. Multiple individuals in the population of a generation of the GA are tested in the same manner described above. Each individual has a set of parameters with values of 0 or 1, wherein the 0-valued parameters effectively filtering out a set of features, thereby yielding a data subset for training a sequence activity model. The individuals are compared and ranked based on their fitness functions. Then one or more of the "fittest" individuals are selected as parents for a next generation of population using at least one diversity mechanism, as described elsewhere herein. In some embodiments, comparison of fitness are implemented using Akaike Information Criterion (AIC) or Bayesian Information Criterion (BIC), wherein individuals having the smallest AIC or BIC values are chosen as the fittest individuals. Typically, the GA is repeated for two or more generations until a convergence criterion is met.

Note that column filtering is optional in some embodiments. According to some embodiments, the raw sequence activity data can be filtered by a genetic algorithm to exclude rows of data instead of or in addition to column filtering.

FIG. 2C shows an example of rows of data (enzyme variants) being filtered out by a genetic algorithm. In this implementation, the genetic algorithm provides a population of individuals, each individual having a set of continuous-valued "genes" or coefficients indicating an exclusion threshold value. If the energy and geometry values are above the threshold for a variant, the variant is excluded from the sequence activity model. The example in FIG. 2C shows a GA individual having the following threshold values: E Total>1.5, E Interaction>1.5, $N_1$>3.3, P>2.8, $C_{(O)}$>3.6, $C_{(H3)}$>6, and $O_{(H)}$>6. These threshold values are for illustrative purposes only and do not indicate optimal thresholds for actual implementations. In this example, this GA individual filters out variant 1 and variant 5, providing a subset of data to train the sequence activity model. Note that the threshold values of the GA may be implemented separately from the sequence activity model, such that the sequence activity model does not include the threshold values. As in column filtering, in some embodiments, the sequence activity model is optimized using an SVM, which outputs hits and misses for predicted activity. The fitness function of the individual is based on the accuracy of the prediction. Multiple individuals of the GA are tested in the same manner described in the example above. The individuals are compared and ranked based on their fitness functions. Then one or more fittest individuals are selected to generate a next generation of population using at least one diversity mechanism, as described elsewhere herein.

In some embodiments, the fittest individuals derived from the GA shown in the examples of FIG. 2 provide subsets of data and train a support vector machine, to define the parameters of a sequence activity model having high predictive power. In some embodiments, this sequence activity model can guide the design of new variants for a new round of directed evolution, as described further below. After one or more "best sequence activity models" are obtained, some embodiments use these models to guide synthesis of actual proteins, which may be further developed by directed evolution. Some embodiments provide methods for designing proteins with desired activity by modifying model-predicted sequences, as described elsewhere herein.

A. First Genetic Algorithm-Selection of Parameters

Figure 3A:
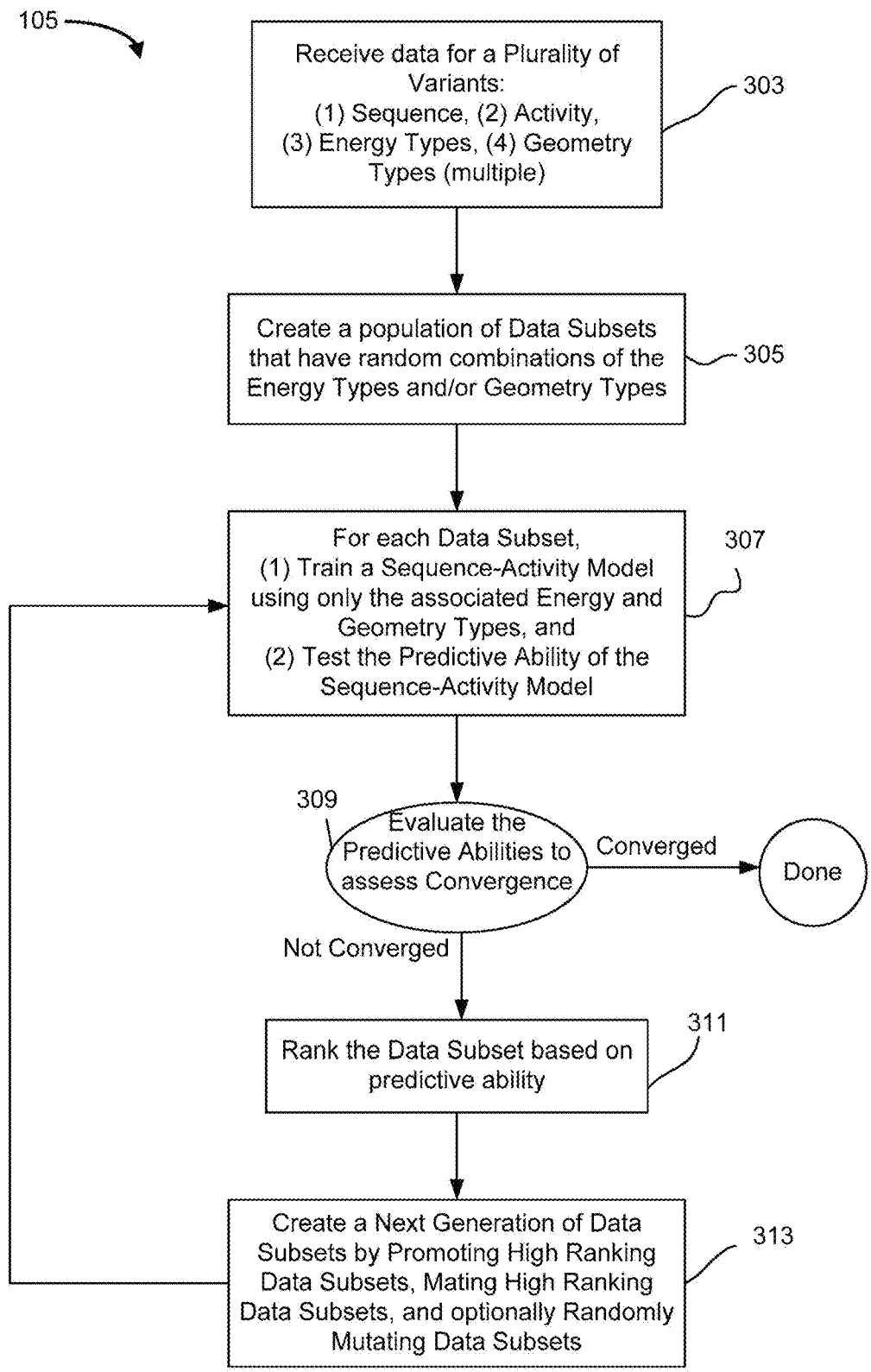
FIG. 3A is a flowchart showing a genetic algorithm for filtering raw data to remove one or more energy types and/or geometry types according to some embodiments of the disclosure.

In certain embodiments such as the embodiment depicted in FIG. 3A, a genetic algorithm selects particular parameters from the pool of available parameters, as well as the activity information for multiple variants. The embodiment shown in FIG. 3A is one way to implement step 105 of filtering raw data to remove one or more energy types and/or geometry types in the process depicted in FIG. 1A. Data for these parameters is provided in an unfiltered data set. See block 303 of FIG. 3A. All the data may be combined in one or more computer readable files for convenient access during execution of the first genetic algorithm.

To implement the first genetic algorithm, a randomly selected group of parameters from the pool of available parameters is used to provide a first generation of data subsets. See block 305. Each collection of parameters, which serve as collections of independent variables, defines a unique data subset. The different randomly selected groups of independent variables (i.e., multiple individual data subsets) are used to train the sequence activity models. In some embodiments, the same number of independent variables is used to create each data subset. In many implementations, the sequence or mutation information is used as an additional independent variable in each and every data subset. Collectively, the data subsets make up the "individuals" in a population of a generation of a genetic algorithm.

In the first generation of the genetic algorithm, sequence activity models are provided from each of the data subsets with each model associated with a different randomly selected combination of independent variables. These are then used to predict activity. See block 307. In certain embodiments, the prediction is performed on sequences that were not used to actually train the model, testing the model's predictive power by cross validation. For example, unfiltered data may be available for 100 variants, but the data for only 70 of these is used to train the sequence activity models. The remaining 30 variants, or more precisely the data for these remaining 30 variants, are used as a test set to test the effectiveness of the sequence activity models, providing cross validation of the model's predictive power.

The resulting data subsets obtained during this first generation of the first genetic algorithm are ranked based on their ability to train models that accurately predict activity. See block 311. The ranking is performed using a fitness function which may be viewed as the performance of the trained models. In other words, the process derives models from the raw data filtered in different ways to remove different combinations of variables. The models evaluate the fitness of the data subsets (i.e., individuals) that were used to train them.

The lowest ranked data subsets reflect the lowest ranked collections of independent variables and are rejected prior to moving to the second generation of the genetic algorithm. The rejected data subsets are replaced with data subsets derived by mating top-performing model types from the first generation. See block 313.

Mating of data subsets may be performed by various techniques. Basically, some of the selected independent variables from each of the two parental data subsets are used in mating, so they may be carried forward to the child data subset. In one example, two parent data subsets are represented as a sequence of 1s and 0s to indicate whether particular parameters from the pool of available independent variables are used as independent variables in the data subsets. These binary representations of the data subsets are cut at a cross-over point and the resulting segments are joined with complementary segments of the data subset from the other parent.

The fitness function, or more precisely the method of evaluating the accuracy of a particular sequence activity model, may be implemented in various ways. In one approach, the fitness function evaluates model accuracy using a confusion matrix. In such technique, each of the variants used in a test set is deemed to be either active or inactive, depending upon whether its measured activity is greater than or less than a defined threshold. Similarly, the sequence activity model is characterized as predicting a variant from the test set to be either active or inactive based upon whether it predicts a value of activity to be above or below the defined threshold value. For each member of the test set, the actual and predicted activity states of the member are compared. A sequence activity model gets credit when it correctly characterizes a test variant as either active or inactive. It loses credit when it predicts that a test variant is inactive when it is measured to be active or when it predicts a test variant to be active when it is measured to be inactive. These four alternatives make up the confusion matrix. The frequency with which a particular model correctly predicts activity or inactivity is used to rank the data subset used to train the model. Another option for characterizing the accuracy of the model relies on the error or difference between its predicted activity (or the magnitude thereof) and the actual measured activity. This distance can be summed or averaged over all the members of the test set.

At the end of the first generation genetic algorithm, a few independent variable groups (i.e., data subsets) for sequence activity models are selected. As mentioned, highly ranked data subsets are selected for mating and/or promotion to the next generation. These subsets contain selected structure (e.g., distance) and/or energy independent variables in addition to the sequence independent variable.

The second generation of data subsets is evaluated for the predictive ability of models trained using them. The process is repeated for multiple generations until the selection of independent variables converge. See convergence block 309. In certain embodiments, a convergence criterion determines whether a current generation's improvement, as compared to the prior generation, is less than a threshold level for one or more consecutive generations. In some embodiments, other ways to test for convergence include, but are not limited to testing for a maximum or minimum fitness value like 100% fitness, running for a fixed number of generations, running within a fixed time limit, or a combination of the above. In certain embodiments, about 5-100 data subsets are produced and evaluated in each generation. In certain embodiments, about 30 to 70 data subsets are produced and evaluated in each generation. It is not intended that the present invention be limited to any particular number of data subsets and/or generations.

B. Second Genetic Algorithm

Figure 3B:
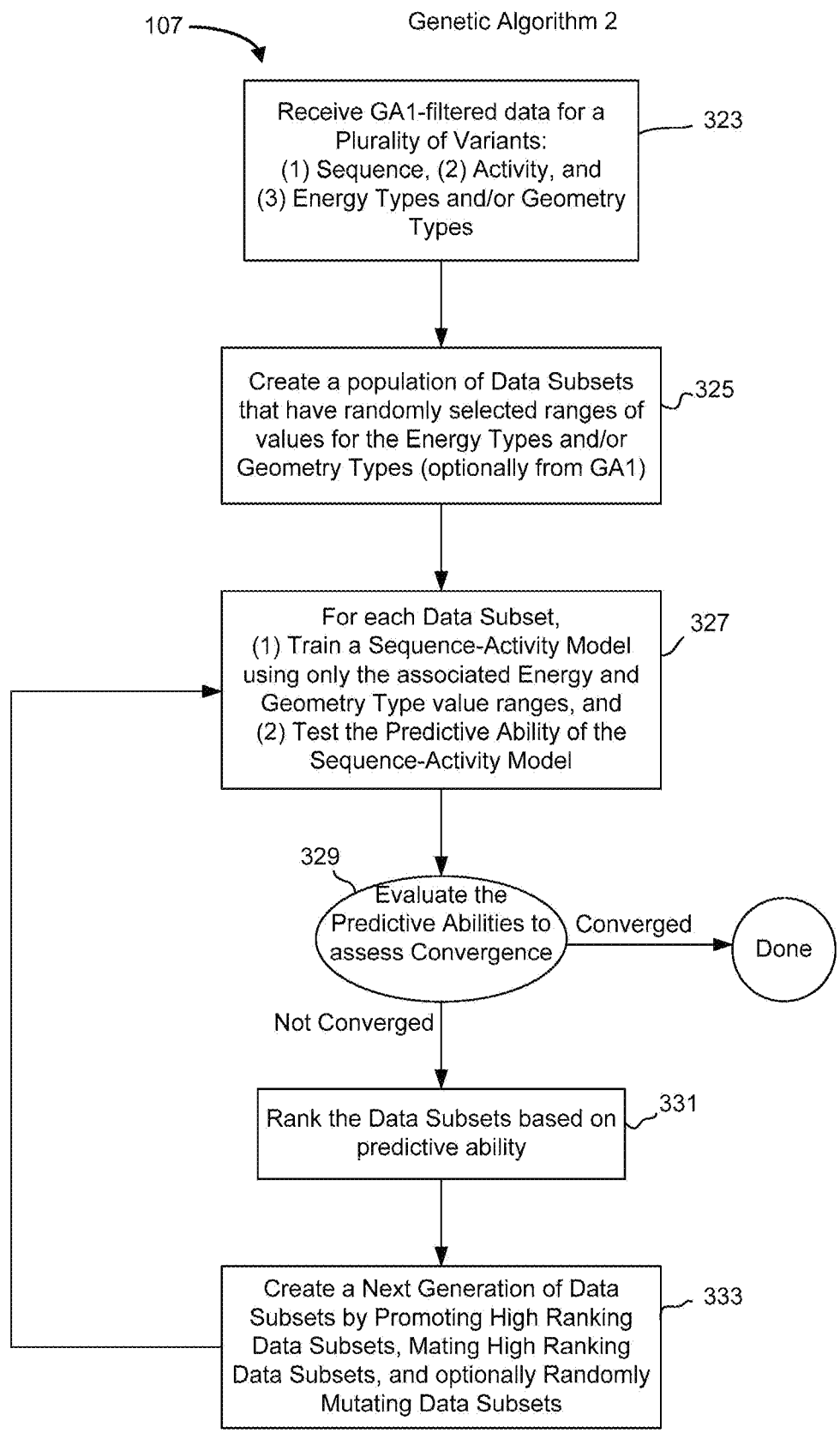
FIG. 3B is a flowchart showing a genetic algorithm for filtering raw data to remove data for variants having energy values and/or geometry values outside defined ranges according to some embodiments of the disclosure.

In a second genetic algorithm as exemplified in FIG. 3B, a process is provided to implement step 107 of FIG. 1A to filter raw data, thereby removing data for variants having energy values and/or geometry values outside defined ranges. In FIG. 3B, the independent variables identified in the first genetic algorithm are fixed. The unselected independent variables are no longer considered relevant, and the second genetic algorithm begins by receiving the data set filtered by the first genetic algorithm. See block 323. It may be assumed that the independent variables selected by the first genetic algorithm are the ones likely to have the most value in accurately predicting activity, at least using the form of sequence activity model under consideration (e.g., an n-dimensional plane generated by a support vector machine). In alternative embodiments, the first genetic algorithm is not performed and all independent variables from the raw data set are used.

It should be understood that the sequences of the variants necessarily set the values of the additional independent variables—the energy and structural constraint variables. For example, the combination of mutations present in the binding pocket will define certain geometric structural binding characteristics and the interaction energy values that serve as available independent variables. Nevertheless, the sequence information alone may be inadequate to effectively train the sequence activity model to accurately predict activity.

In the second genetic algorithm, each independent variable (other than sequence) is refined such that only variants meeting a threshold value of an independent variable are selected for use in the data subset. This refinement may be applied to multiple non-sequence independent variables. In other words, the second genetic algorithm selects a sub range within the total available range of magnitudes for one or more of the selected non-sequence independent variables. As an example of one approach, a given independent variable may have a dynamic range of about 0 to 20 Å, which represents the distance between two atoms or between two docked positions of the same atom. A more refined version of this independent variable considers only variants having values of about 12 Å or less. Another example of a range of values may be about 5 Å or less. A goal of the second genetic algorithm is to home in on the portion of the full range of variable magnitudes that are useful for predicting activity. This appears to reduce noise in the predictive ability of the trained models.

In the first generation of this second type of genetic algorithm, each of the independent variables (other than the sequence variable) is partitioned into a portion. The partitioning is performed randomly. See block 325. For example, particular values of magnitude for each of the independent variables are randomly selected. Only variants having values less than this partition point are considered. This effectively pares the independent variables used in the training set for the sequence activity model.

In the first generation, individual data subsets have randomly selected cutoff points for each non-sequence independent variable. Block 325. Each individual data subset in the first generation trains using its own unique sequence activity model. See block 327. The resulting models are used to predict activity for each member of a test set. Block 327. Each individual data subset is ranked for its ability to train an accurate model by using, e.g., a confusion matrix as described above. See block 331. This is the fitness function. Alternative fitness functions are possible. These include functions that utilize difference values between the predicted and actual value. Fitness can also be based on the types of independent variables used in the models and/or the fraction of the full range of independent variable values used.

In certain embodiments, a data subset contains data for a subset of the variants in the raw data set. The data for a fraction of these variants is used to train a sequence activity model. The data for the remaining variants is used to test the resulting sequence activity model. In other words, each data subset is divided into a training set and a test set. The division may be conducted by random selection. In some embodiments, the training set contains between about 20 and 90% (or between about 50 and 80%) of the variants in the subset. It is not intended that the present invention be limited to any particular number of variants in the subsets and/or training sets.

The high scoring data subsets in the first generation are selected for use in the second generation and/or as parents for mating to produce offspring for the second generation. See block 333. Mating can take place using any suitable technique(s). In one embodiment, a cost-weighting scheme, such as a weighted sum of differences is applied using the cutoff (i.e., threshold) values for each of two mating parents for a given independent variable. In a cost-weighting scheme, the mating selection is biased toward individuals (i.e., data subsets) having relatively higher fitness. The most fit individuals mate more than the less fit individuals. Other mating selection schemes include proportional roulette wheel selection, rank-based roulette wheel selection, and tournament selection.

The actual mating process can take many forms. One example is continuous parameter mating. In this approach, the cutoff value for a given parameter in a child data subset is a value that is between the cutoff values for the same parameter in the two parent data subsets. For example, one parent may have a cutoff value of 0.1 angstroms for a first parameter (distance X), while the other parent may have a cutoff value of 0.6 angstroms for distance X. The child's cutoff value for distance X will be between 0.1 and 0.6 angstroms. Various functions can be defined to determine the child's intermediate cutoff value for distance X. In a continuous parameter mating scheme, a "beta" value is randomly chosen and applied to determine the fractional distance between the parents' two cutoff values. In the above example, if beta is chosen to be 0.7 and two children are produced, the children's cutoff values may be calculated as follows:

child 1's distance=0.1−(0.7)*0.1+(0.7)*0.6=0.45 child 2's distance=0.6+(0.7)*0.1−(0.7)*0.6=0.25 child 1=$a$+beta*($b$−$a$)

child 2=$b$+beta*($a$−$b$)

In a second generation, the individuals (defined data subsets) selected and/or produced by mating in the first round are evaluated by applying the fitness function to each of them. In other words, the process of blocks 327, 331, and 333 is applied to the second generation. As with the first generation, the data subsets may be ranked based on their ability to train models that accurately predict activity in a test set of variants. The high ranking subsets may be passed through to the next generation and/or mated as described above.

Further generations, continue as with the second generation until convergence is reached. As depicted in FIG. 3B, each generation is subjected to a convergence check. See block 329. In certain embodiments, a convergence criterion determines whether the current generation's improvement, as compared to the prior generation, is less than a threshold level for one or more consecutive generations. Other ways to test for convergence include testing for a maximum/minimum fitness value such as 100% fitness, running for a fixed number of generations, running within a fixed time limit, or a combination of the above.

In certain embodiments, about 5-100 data subsets are produced and evaluated for each generation. In certain embodiments, about 30 to 70 data subsets are produced and evaluated for each generation. In a particular example, there are about 45 individual data subsets in each generation of the second genetic algorithm. However, it is not intended that the present invention be limited to any particular number of data subsets characterized and/or used for each or any generation.

In some aspects, this data set filtering process may be characterized as follows. Initially, a system uses an unfiltered data set to create a population of data subsets. Each of these subsets is an "individual" in a population of a generation of a genetic algorithm. Each data subset is identified using parameter values thresholds (cutoffs) for geometric parameters characterizing the binding of a ligand to a binding site of a biomolecule. When the system applies the parameter value thresholds it effectively removes certain variants from the unfiltered data set. In other words, each data subset contains data for only some of the variants included in the unfiltered data set.

For each data subset (i.e., individual), the system divides the constituent variants into those that belong to a training set and those that belong to a test set. Variants belonging to the training set are used to train a sequence activity model. Training may be accomplished using a technique such as a support vector machine or partial least squares. The resulting trained sequence activity model is applied to the test set variants. The model predicts activity for each test set variant and the system thereby assesses the accuracy of the sequence activity model and hence its associated data subset. Each data subset (i.e., individual) in the population of the generation of a genetic algorithm is evaluated for accuracy in the same manner.

For a given generation of a genetic algorithm, each of the data subsets and associated sequence activity models are ranked based on their ability to accurately predict activity for the variants in the associated test set. Within the generation, the process selects the top-ranked subsets for promotion to the next generation. Additionally, the process mates some of the top ranked subsets to produce child subsets, which are also provided to the next generation. The next generation data subsets (i.e., individuals) are treated as described above. Multiple generations are treated and evaluated until convergence is reached.

C. Third Genetic Algorithm

Figure 3C:
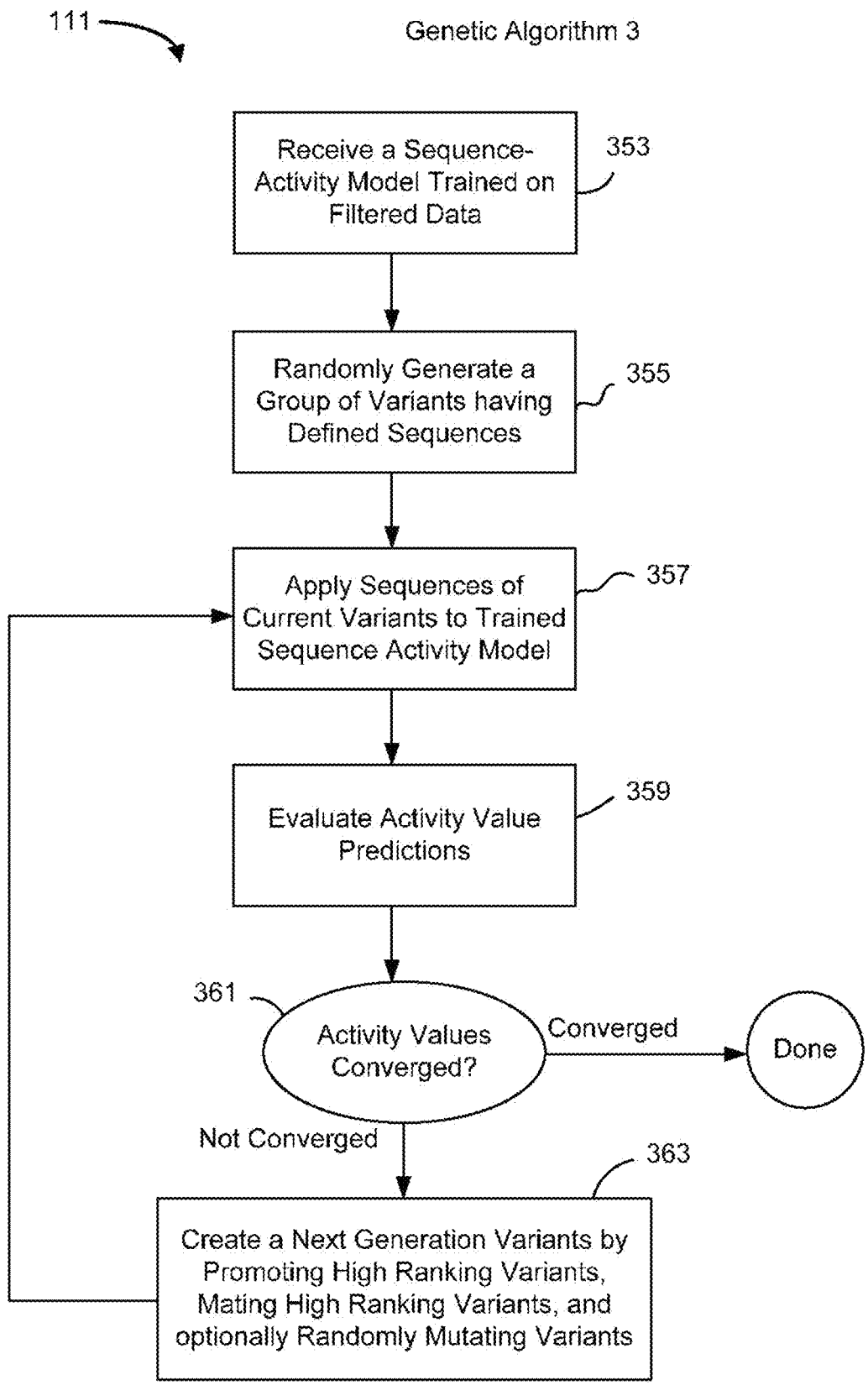
FIG. 3C is a flowchart showing a genetic algorithm for identifying new biomolecule variants using a sequence activity model of high predictive power according to some embodiments of the disclosure.

In the described work flow, a data subset selected by filtering the raw sequence, activity, and structure data trains a high accuracy sequence activity model. A support vector machine may be used to perform the training. The resulting sequence activity model identifies new variant biomolecules. In some embodiments, these new variant biomolecules are used in at least one round of directed evolution. In certain embodiments, a final genetic algorithm is employed to identify the new biomolecule variants described in block 111 of FIG. 1A. An example of a suitable genetic algorithm is depicted in FIG. 3C. As shown there, the process begins with the sequence activity model selected after concluding the second genetic algorithm. Block 353.

As pointed out above, there is a difference between this genetic algorithm and other genetic algorithms discussed herein. This algorithm provides nucleic acid, amino acid, or other biomolecule sequences as individuals in a population. In contrast, in other genetic algorithm discussed herein, the individuals are models or sets of model parameters. In a first generation of this GA, the genetic algorithm provides a random population of individuals, each representing a distinct protein (or other biomolecule) sequence. Block 355. The individual proteins differ from one another by mutations at given positions. In some implementations, the mutations are generated randomly, at least in the first generation. The mutations may be generated with respect to a single protein backbone such as the backbone of a wild-type protein or a reference backbone identified during a round of directed evolution.

The individuals in the first generation are ranked or selected using a fitness function that is the sequence activity model trained on the data subset obtained at the conclusion of the second genetic algorithm (i.e., the model passed forward in block 353). See blocks 357 and 359. Identifying sequence information for each individual biomolecule is input to the sequence activity model. This information may be a list of mutations, optionally identifying both the starting and ending residues for each of the positions where mutations reside. The model acts on this input by assigning a predicted activity to each individual. Block 357. The individual biomolecules having the top ranked activity values (as predicted by the model) are selected for mating and/or for transfer to the next generation. Blocks 359 and 363. The mated individuals provide new combinations of mutations, with each new combination being a member of the next generation. In certain embodiments, mating is accomplished by a crossover operation. An example of a crossover operation in this genetic algorithm may be understood as follows. Parent 1 has mutations in positions 12 and 25, and parent 2 has mutations in positions 15 and 30. The first offspring may have mutations in position 12 from parent 1 and in position 30 from parent 2, and the second offspring will have mutations in positions 25 from parent 1 and position 12 from parent 2.

In some cases, some of the offspring produced by mating (e.g., 20% of them) are further mutated using any suitable method, including but not limited to point mutations. Such mutations may be performed randomly.

Further generations of populations of distinct biomolecules are derived as described for the second generation. Creation of new generations repeats until the activity predicted by the model does not significantly improve for a defined number of generations. At this point, the population of biomolecules is deemed to have converged to a final list of ranked individuals that are identified by a set of mutations and a predicted activity. A convergence condition is shown at block 361 in FIG. 3C.

In certain embodiments, the individual biomolecules from the final list are synthesized and screened in vitro. Additionally, the individual biomolecules may be analyzed to provide geometric constraints or other structural data and/or interaction energy through use of docking software or other tools. The resulting sequence, activity, and structural/energy data are then combined to serve as the input to the workflow for a next round of directed evolution. In other words, the proteins screened after the genetic algorithm provide data that may serve as a new training set for a second round of analysis. Thus, the data filtering genetic algorithm is performed again but with an entirely new training set. In some embodiments, the data set and the sequence activity model from one round of directed evolution are not preserved in the next round. That is, the next round starts fresh, looking for a new set of independent variables using the new unfiltered data set.

In some embodiments, the sequence activity model employed in the third genetic algorithm is trained using energy and/or structural (geometric) parameters as well as sequence information. In certain implementations, however, the final genetic algorithm only inputs sequence information, not energy and/or structural information, to the model. In other words, while the model was developed using sequence and energy and/or structural independent variables, the model does not receive the energy and/or structural independent variables when evaluating new sequences in the third genetic algorithm.

In certain embodiments, about 10 to 10,000 biomolecules are evaluated in each generation. In certain embodiments, about 100 to 1000 biomolecules are evaluated in each generation. In a particular example, there are about 500 individual biomolecules in each generation of the third genetic algorithm. It is not intended that the present invention be limited to any particular number of biomolecules that are evaluated.

At some point, the above-described process is completed and one or more variants of the current generation is selected for further investigation, synthesis, development, production, etc. In one example, a selected biomolecule variant is used to seed one or more rounds of in vitro directed evolution. As an example, a round of in vitro directed evolution may include (i) preparing a plurality of oligonucleotides containing or encoding at least a portion of the selected protein variant, and (ii) performing a round of in vitro directed evolution using the plurality of oligonucleotides. The oligonucleotides may be prepared by gene synthesis, fragmentation of a nucleic acid encoding some or all of the selected protein variant, etc. In certain embodiments, the round of in vitro directed evolution includes fragmenting and recombining the plurality of oligonucleotides. In certain embodiments, the round of in vitro directed evolution includes performing saturation mutagenesis on the plurality of oligonucleotides.

V. Sequence Activity Models

The methods and systems disclosed herein provide a sequence activity model of high predictive power. In some embodiments, the sequence activity model is a non-linear model. In other embodiments, it is a linear model. Examples of linear and non-linear sequence activity models are described in U.S. Pat. No. 7,747,391, U.S. Patent Application Publication No. 2005/0084907, U.S. Provisional Patent Application No. 61/759,276, and U.S. Provisional Patent Application No. 61/799,377, each of which is incorporated herein by reference in its entirety. In various embodiments described herein, the sequence activity model is implemented as an n-dimensional hyperplane, which may be generated by a support vector machine. In the following description, when a sequence activity model is exemplified as an n-dimensional hyperplane generated support vector machine, it is intended that this form or the model could be substituted by other types of linear and non-linear models such as least squares models, partial least squares models, multiple linear regression, principal component regression, partial least squares regression, support vector machine, neural network, Bayesian linear regression, or bootstrap, and ensemble versions of these.

As indicated above, in some embodiments, a sequence activity model used with the embodiments herein relates protein sequence information to protein activity. The protein sequence information used by the model may take many forms. In some embodiments, it is a complete sequence of the amino acid residues in a protein. However, in some embodiments, the complete amino acid sequence is unnecessary. For example, in some embodiments, it is sufficient to provide only those residues that are to be varied in a particular research effort. In some embodiments involving later research stages, many residues are fixed and only limited regions of sequence space remain to be explored. In some of such situations, it is convenient to provide sequence activity models that require, as inputs, only the identification of those residues in the regions of the protein where the exploration continues. In some additional embodiments, the models do not require that the exact identities of residues at the residue positions of interest be known. In some such embodiments, one or more physical or chemical properties that characterize the amino acid at a particular residue position is/are identified. In some embodiments, geometrical parameters describing structural information, e.g., the distances between moieties, are included in the model. Although the structural information may be implemented in a structural model, it can also be implemented as part of a sequence activity model. Alternatively, the structural information may be used to filter out data to select a subset of sequence activity data to train a sequence activity model.

Furthermore, in some models, combinations of such properties are employed. Indeed, it is not intended that the present invention be limited to any particular approach, as the models find use in various configurations of sequence information, activity information structural information, and/or other physical properties (e.g., hydrophobicity, etc.).

In some embodiments described above, amino acid sequences provide information for independent variables for sequence activity models. In other embodiments, nucleic acid sequences, as opposed to amino acid sequences, provide information for independent variables. In the latter embodiments, IVs representing the presence or absence of nucleotides of particular types at particular positions of nucleotide sequences are used as the input for the model. Proteins derived from the nucleotide sequences provide activity data as the output of the model. One skilled in the art recognizes that different nucleotide sequences may be translated into the same amino acid sequence due to codon degeneracy, wherein two or more different codons (i.e., trios of nucleotides) encode the same amino acid. Therefore, different nucleotide sequences can potentially relate to the same protein and protein activity. However, a sequence activity model taking nucleotide sequence information as an input and protein activity as an output does not need to concern such degeneracy. Practically, the lack of a one-to-one correspondence between an input and an output may introduce noise into the model in some embodiments, but such noise does not negate the utility of the model. In some embodiments, such noise may even improve the predictive power of the model, because, e.g., the model is less likely to over fit the data. In some embodiments, the models generally treat activity as a dependent variable and sequence/residue values as independent variables. Activity data may be obtained using any suitable means known in the art, including, but not limited to assays and/or screens appropriately designed to measure magnitudes of the activity/activities of interest. Such techniques are well known to those in the art and are not essential to the current invention. Indeed, the principles for designing appropriate assays or screens are widely understood and known in the art. Techniques for obtaining protein sequences are also well known and are not key to the current invention. As mentioned, next-generation sequencing technologies may be used. In some embodiments, the activity of interest may be protein stability (e.g., thermal stability). However, many important embodiments consider other activities such as catalytic activity, resistance to pathogens and/or toxins, therapeutic activity, toxicity, and the like. Indeed, it is not intended that the present invention be limited to any particular assay/screening method(s) and/ or sequencing method(s), as any suitable method known in the art finds use in the present invention.

In various embodiments, the form of the sequence activity model can vary widely, so long as it provides a vehicle for correctly approximating the relative activity of proteins based on sequence information, as desired. Examples of the mathematical/logical form of models include, but are not limited to additive, multiplicative, linear/non-interaction, and non-linear/interaction mathematical expressions of various orders, neural networks, classification and regression trees/graphs, clustering approaches, recursive partitioning, support vector machines, and the like.

Various techniques for generating models are available and find use in the present invention. In some embodiments, the techniques involve optimization of models or minimization of model errors. Specific examples include, but are not limited to partial least squares, ensemble regression, random forest, and various other regression techniques, as well as neural network techniques, recursive partitioning, support vector machine techniques, CART (classification and regression trees), and/or the like. Generally, the technique should produce a model that can distinguish residues that have a significant impact on activity from those that do not. In some embodiments, the models also rank individual residues or residue positions based on their impact on activity. It is not intended that the present invention be limited to any specific technique for generating models, as any suitable method known in the art finds use in the present invention.

In some embodiments involving additive models, the models are generated by a regression technique that identifies covariation of independent and dependent variables in a training set. Various regression techniques are known and widely used. Examples include, but are not limited to multiple linear regression (MLR), principal component regression (PCR), and partial least squares regression (PLS). In some embodiments, models are generated using techniques that involve multiple constituents, including but not limited to ensemble regression and random forest. These and any other suitable methods find use in the present invention. It is not intended that the present invention be limited to any particular technique.

MLR is the most basic of these techniques. It is used to simply solve a set of coefficient equations for members of a training set. Each equation relates to the activity of a training set member (i.e., dependent variables) with the presence or absence of a particular residue at a particular position (i.e., independent variables). Depending upon the number of residue options in the training set, the number of these equations can be quite large.

Like MLR, PLS and PCR generate models from equations relating sequence activity to residue values. However, these techniques do so in a different manner. They first perform a coordinate transformation to reduce the number of independent variables. They then perform the regression on the transformed variables. In MLR, there is a potentially very large number of independent variables: two or more for each residue position that varies within the training set. Given that proteins and peptides of interest are often quite large and the training set may provide many different sequences, the number of independent variables can quickly become very large. By reducing the number of variables to focus on those that provide the most variation in the data set, PLS and PCR generally require fewer samples and simplify the steps involved in generating models.

PCR is similar to PLS regression in that the actual regression is done on a relatively small number of latent variables obtained by coordinate transformation of the raw independent variables (i.e., residue values). The difference between PLS and PCR is that the latent variables in PCR are constructed by maximizing covariation between the independent variables (i.e., residue values). In PLS regression, the latent variables are constructed in such a way as to maximize the covariation between the independent variables and the dependent variables (i.e., activity values). Partial Least Squares regression is described in Hand, D. J., et al. (2001) Principles of Data Mining (Adaptive Computation and Machine Learning), Boston, Mass., MIT Press, and in Geladi, et al. (1986) "Partial Least-Squares Regression: a Tutorial," Analytica Chimica Acta, 198:1-17. Both of these references are incorporated herein by reference for all purposes.

In PCR and PLS, the direct result of the regression analysis is an expression for activity that is a function of the weighted latent variables. This expression can be transformed to an expression for activity as a function of the original independent variables by performing a coordinate transformation that converts the latent variables back to the original independent variables.

In essence, both PCR and PLS first reduce the dimensionality of the information contained in the training set and then perform a regression analysis on a transformed data set, which has been transformed to produce new independent variables, but preserves the original dependent variable values. The transformed versions of the data sets may result in only a relatively few expressions for performing the regression analysis. In protocols in which no dimension reduction has been performed, each separate residue for which there can be a variation must be considered. This can be a very large set of coefficients (e.g., $2^N$ coefficients for two-way interactions, where N is the number of residue positions that may vary in the training set). In a typical principal component analysis, only 3, 4, 5, or 6 principal components are employed. However, it is not intended that the present invention be limited to any particular number of principal components.

The ability of machine learning techniques to fit the training data is often referred to as the "model fit" and in regression techniques such as MLR, PCR and PLS, the model fit is typically measured by the sum squared difference between measured and predicted values. For a given training set, the optimal model fit will be achieved using MLR, with PCR and PLS often having a worse model fit (higher sum squared error between measurements and predictions). However, the chief advantage of using latent variable regression techniques such as PCR and PLS lies in the predictive ability of such models. Obtaining a model fit with very small sum squared error in no way guarantees the model will be able to accurately predicted new samples not seen in the training set—in fact, it is often the opposite case, particularly when there are many variables and only a few observations (i.e., samples). Thus, latent variable regression techniques (e.g., PCR, PLS), while often having worse model fits on the training data are usually more robust and are able to predict new samples outside the training set more accurately.

Support vector machines (SVMs) can also be used to generate models used in the present invention. As explained above, SVMs take training sets of sequences that have been classified into two or more groups based on activity as inputs. Support vector machines operate by weighting different members of a training set differently depending upon how close they are to a hyperplane interface separating "active" and "inactive" members of the training set. This technique requires that the scientist first decide which training set members to place in the "active" group and which training set members to place in the "inactive" group. In some embodiments, this is accomplished by choosing an appropriate numerical value for the activity level that serves as the boundary between "active" and "inactive" members of the training set. From this classification, the support vector machine generates a vector, W, that can provide coefficient values for the individual independent variables defining the sequences of the active and inactive group members in the training set. These coefficients can be used to "rank" individual residues as described elsewhere herein. The technique is used to identify a hyperplane that maximizes the distance between the closest training set members on opposite sides of that plane.

VI. Protein Docking

In some embodiments, a virtual protein docking or screening system is configured to perform various operations associated with computationally identifying biomolecule variants that are likely to have a desirable activity such as efficiently and selectively catalyzing a reaction at a defined temperature. The virtual protein docking system may take as inputs representations of at least one ligand intended to interact with the variants. The system may take as other inputs representations of the biomolecule variants, or at least the binding sites of these variants. The representations may contain three-dimensional positions of atoms and/or moieties of the ligands and/or variants. Homology models are examples of the representations of the biomolecule variants. In some embodiments, a virtual protein screening system may apply docking information and activity constraints to assess the functioning of the variants.

In certain embodiments, a virtual protein docking and screening system determines one or more energy values and one or more geometry values with reference to the relations between moieties on two different molecules. In some embodiments, the energy values may include an interaction energy between a substrate and an enzyme with the substrate being in one or more poses docked with the enzyme. In some embodiments, the energy values may include a total docking energy including an interaction energy and an internal energy of the participants of binding interaction. In some embodiments, the geometry values may include distance, angle, or torsion values between moieties of two molecules. In some embodiments, the geometry values include distance between corresponding moieties on a native and a desired substrate, both docked to the same enzyme. In other embodiments, the geometry values include distance between a substrate and an enzyme docked with each other.

When considering catalytic turnover of a substrate as the activity, the virtual protein screening system may be configured to identify poses known to be associated with a particular reaction. In some embodiments, this involves considering a reaction intermediate or transition state rather than the substrate itself. In addition to turnover, poses may be evaluated for other types of activity such as stereoselective synthesis of enantiomers, binding to a receptor of a target biomolecule identified as important for drug discovery, etc. In some cases, the activity is irreversible or reversible covalent binding such as targeted covalent inhibition (TCI).

In certain embodiments, a protocol to calculate binding energies is executed to evaluate the energetics of each active pose of a variant. In some implementations, the protocol may consider van der Waals force, electrostatic interaction, and solvation energy. Solvation is typically not considered in calculations performed by dockers. Various solvation models are available for calculating binding energies. These include, but are not limited to distance dependent dielectrics, Generalized Born with pairwise summation (GenBorn), Generalized Born with Implicit Membrane (GBIM), Generalized Born with Molecular Volume integration (GBMV), Generalized Born with a simple switching (GB SW), and the Poisson-Boltzmann equation with non-polar surface area (PBSA). Protocols for calculating binding energies are different or separate from docker programs. They generally produce results that are more accurate than docking scores, due in part to the inclusion of solvation effects in their calculations. In various implementations, binding energies are calculated only for poses that are deemed to be active.

A. Structural Models of Biomolecules and their Binding Sites

In certain embodiments, a computer system provides three-dimensional models for protein variants (or other biomolecules). The three-dimensional models are computational representations of some or all of the protein variants' full length sequences. Typically, at a minimum, the computation representations cover at least the protein variants' binding sites.

As described herein, the three-dimensional models may be homology models prepared using an appropriately designed computer system. The three-dimensional models employ a structural template in which the protein variants vary from one another in their amino acid sequences. Generally, a structural template is a structure previously solved by X-ray crystallography or NMR for a sequence that is homologous to the model sequence. The quality of the homology model is dependent on the sequence identity and resolution of the structure template. In certain embodiments, the three-dimensional models may be stored in a database for use as needed for current or future projects.

Three-dimensional models of the protein variants may be produced by techniques other than homology modeling. One example is protein threading, which also requires a structure template. Another example is ab initio- or de novo-protein modeling which does not require a structure template and is based on underlying physical principles. Examples of ab initio techniques include molecular dynamics simulations and simulations using the Rosetta software suite.

In some embodiments, the protein variants vary from one another in their binding sites. In some cases, the binding sites differ from one another by at least one mutation in the amino acid sequence of the binding site. The mutation may be made in a wild-type protein sequence or some other reference protein sequence. In some cases, two or more of the protein variants share the same amino acid sequence for the binding site but differ in the amino acid sequence for another region of the protein. In some cases, two protein variants differ from one another by at least about 2 amino acids, or at least about 3 amino acids, or at least about 4 amino acids. However, it is not intended that the present invention be limited to any specific number of amino acid differences between protein variants.

In certain embodiments, the plurality of variants includes members of library produced by one or more rounds of directed evolution. Diversity generation techniques used in directed evolution include gene shuffling, site-directed mutagenesis, and the like. Examples of directed evolution techniques are described in U.S. Pat. No. 7,024,312, U.S. Patent Application Publication No. 2012/0040871, U.S. Pat. No. 7,981,614, WO2013/003290, PCT Application No. PCT/US2013/030526, each of which is incorporated herein by reference in its entirety.

B. Dock a Ligand to Protein Variants

As explained herein, docking may be employed to identify interaction energy and/or geometric parameters for use in training sequence activity models. Typically, docking is conducted by an appropriately programmed computer system that uses a computational representation of a ligand and computational representations of the binding sites of the generated plurality of variants.

As an example, a docker may be configured to perform some or all of the following operations:

1. Generate a set of ligand conformations using high-temperature molecular dynamics with random seeds. The docker may generate such conformations without consideration of the ligand's environment. Hence, the docker may identify favorable conformations by considering only internal strain or other considerations specific to the ligand alone. The number of conformations to be generated can be set arbitrarily. In one embodiment, at least about 10 conformations are generated. In another embodiment, at least about 20 conformations are generated, or at least about 50 conformations, or at least about 100 conformations. However, it is not intended that the present invention be limited to a specific number of conformations.

2. Generate random orientations of the conformations by translating the center of the ligand to a specified location within the receptor active site, and performing a series of random rotations. The number of orientations to refine can be set arbitrarily. In one embodiment, at least about 10 orientations are generated. In another embodiment, at least about 20 orientations are generated, or at least about 50 orientations, or at least about 100 orientations. However, it is not intended that the present invention be limited to any specific number of orientations. In certain embodiments, the docker calculates a "softened" energy to generate further combinations of orientation and conformation. The docker calculates softened energy using physically unrealistic assumptions about the permissibility of certain orientations in a binding site. For example, the docker may assume that ligand atoms and binding site atoms can occupy essentially the same space, which is impossible based on Pauli repulsion and steric considerations. This softened assumption can be implemented by, for example, employing a relaxed form of the Lennard-Jones potential when exploring conformation space. By using a softened energy calculation, the docker allows a more complete exploration of conformations than available using physically realistic energy considerations. If the softened energy of a conformation in a particular orientation is less than a specified threshold, the conformation-orientation is kept. These low energy conformations are retained as "poses". In certain implementations, this process continues until either a desired number of low-energy poses is found, or a maximum number of bad poses is found.

3. Subject each retained pose from step 2 to simulated annealing molecular dynamics to refine the pose. The temperature is increased to a high value then cooled to the target temperature. The docker may do this to provide a more physically realistic orientation and/or conformation than is provided by the softened energy calculation.

4. Perform a final minimization of the ligand in the rigid receptor using non-softened potential. This provides a more accurate energy value for the retained poses. However, the calculation may provide only partial information about the poses' energies.

5. For each final pose, calculate the total energy (receptor-ligand interaction energy plus ligand internal strain) and the interaction energy alone. The calculation may be performed using CHARMm. The poses are sorted by CHARMm energy and the top scoring (most negative, thus favorable to binding) poses are retained. In some embodiments, this step (and/or step 4) removes poses that are energetically unfavorable.

The following reference provides an example of a docker's functioning: Wu et al., *Detailed Analysis of Grid-Based Molecular Docking: A Case Study of CDOCKER—A CHARMm-Based MD Docking Algorithm*, J. Computational Chem., Vol. 24, No. 13, pp 1549-62 (2003), which is incorporated herein by reference in its entirety.

A docker such as the one described here may provide such information as the identity of variants for which docking with the desired substrate is unlikely, sets of poses (one set for each variant) that can be considered for activity, and interaction energies for the poses in the sets.

C. Determine Geometric Parameters of the Docked Ligand

For a protein variant that successfully docks with the ligand, geometric binding parameters may identify one or more active poses. An active pose is one meeting one more constraints for the ligand to bind under defined conditions (rather than arbitrary binding conditions). If the ligand is a substrate and the protein is an enzyme, active binding may be binding that allows the substrate to undergo a catalyzed chemical transformation, particularly a stereo-specific transformation. In some implementations, geometrical binding characteristics define relative positions of one or more atoms in the ligand and one or more atoms in the protein and/or cofactor associated with the protein.

In some cases, geometric parameters are identified from one or more conformations of a native substrate and/or subsequent intermediate when it undergoes a catalyzed chemical transformation by a wild-type enzyme. In certain embodiments, the geometric parameters include (i) a distance between a particular moiety on the substrate and/or subsequent intermediate and a particular residue or residue moiety in the catalytic site, (ii) a distance between a particular moiety on the substrate and/or subsequent intermediate and a particular cofactor in the catalytic site, and/or (iii) a distance between a particular moiety on the substrate and/or subsequent intermediate and a particular moiety on an ideally positioned native substrate and/or subsequent intermediate in the catalytic site. Alternatives to distance include angles between bonds or inter-compound atomic alignments, torsional positions around a common axis, etc. Examples of these geometric parameters are described in U.S. patent application Ser. No. 14/498,864, which is incorporated herein by reference in its entirety.

A plurality of poses of the computational representation of the substrate and/or subsequent intermediate may be generated with respect to a computational representation of the protein variant under consideration. The plurality of poses may be generated by various techniques. General examples of such techniques include, but are not limited to systematic or stochastic torsional searches about rotatable bonds, molecular dynamics simulations, and genetic algorithms designed to locate low energy conformations. In one example, the poses are generated using high temperature molecular dynamics, followed by random rotation, refinement by grid-based simulated annealing, and/or a final grid-based or force field minimization to generate a conformation and/or orientation of the substrate and/or subsequent intermediate in the computational representation catalytic site. Some of these operations are optional, e.g., refinement by grid-based simulated annealing, and grid-based or force field minimization.

In certain embodiments, the number of poses considered is at least about 10, or at least about 20, or at least about 50, or at least about 100, or at least about 200, or at least about 500. However, it is not intended that the present invention be limited to a specific number of poses considered.

VII. Generating Proteins with Desired Activity by Modifying Model-Predicted Sequences One of the goals of the invention is to generate an optimized protein variant library through directed evolution. Some embodiments of the invention provide methods to guide directed evolution of protein variants using the generated sequence-activity models. The various sequence-activities models prepared and refined according to the methods described above are suitable to guide directed evolution of proteins or biological molecules. As part of the process, the methods may identify sequences that are to be used for generating new protein variants for a next round of directed evolution as indicated by block 111 of FIG. 1A. Such sequences include variations on the defined residues identified above, or are precursors used to subsequently introduce such variations. The sequences may be modified by performing mutagenesis and/or a recombination-based diversity generation mechanism to generate the new library of protein variants. In some embodiments, the new variants can be assayed for activity of interest. See block 113 of FIG. 1A. In some applications, structural models may be generated for the new variants, which structural models can provide energy values and geometry values for the variants. See block 113 of FIG. 1A. In some embodiments, these data may then be used in developing a new sequence-activity model in a new round of directed evolution. See block 115 of FIG. 1A.

In some embodiments, preparation of oligonucleotides or nucleic acid sequences is achieved by synthesizing the oligonucleotides or nucleic acid sequences using a nucleic acid synthesizer. Some embodiments of the invention include performing a round of directed evolution using the prepared oligonucleotides or protein sequence as building blocks for directed evolution. Various embodiments of the invention can apply recombination and/or mutagenesis to these building blocks to generate diversity.

In some embodiments, the process identifies one or more sequences having advantageous properties. Then variants are generated from the identified sequences as a training set for a sequence activity model in a new round of directed evolution. See blocks 355 and 357 of FIG. 3C.

To generate variants, as one specific example, some embodiments apply recombination techniques to oligonucleotides. In these embodiments, the methods involve selecting one or more mutations for a round of directed evolution by evaluating the coefficients of the terms of the sequence-activity model. Mutations are selected from combinations of defined amino acids or nucleotides of specific residue types at specific positions, based on their contributions to the activity of proteins as predicted by the models. In some embodiments, selection of mutations involves identifying one or more coefficients that are determined to be larger than others of the coefficients. Each of the coefficients relates to a residue's contribution to protein activity, and the residue is defined to be of a specific type at a specific location. Selection of mutations involves selecting the residues associated with the one or more coefficients so identified. In some embodiments, after selecting mutations according to the sequence-activity models, the methods involve preparing a plurality of oligonucleotides containing or encoding at least one mutation, and performing a round of directed evolution. In some embodiments, the directed evolution techniques involve combining and/or recombining the oligonucleotides.

Other embodiments apply recombination techniques to protein sequences. In some embodiments, the methods involve identifying a new protein or a new nucleic acid sequence, and preparing and assaying the new protein or a protein encoded by the new nucleic acid sequence. In some embodiments, the methods further involve using the new protein or protein encoded by the new nucleic acid sequence as a starting point for further directed evolution. In some embodiments, the directed evolution process involves fragmenting and recombining the protein sequence that is predicted by the model to have a desired level of activity.

In some embodiments, the methods identify and/or prepare a new protein or a new nucleic acid sequence based on individual mutations that are predicted to be important by the model. These methods involve: selecting one or more mutations by evaluating the coefficients of the terms of the sequence-activity model to identify one or more of the defined amino acids or nucleotides at the defined positions that contribute to the activity; identifying a new protein or a new nucleic acid sequence comprising the one or more mutations selected above, and preparing and assaying the new protein or a protein encoded by the new nucleic acid sequence.

In other embodiments, the methods identify and/or prepare a new protein or a new nucleic acid sequence based on the predicted activity of a whole sequence instead of individual mutations. In some of these embodiments, the methods involve applying multiple protein sequences or multiple amino acid sequences to the sequence-activity model and determining activity values predicted by the sequence-activity model for each of the multiple protein sequences or nucleic acid sequences. The methods further involve selecting a new protein sequence or a new nucleic acid sequence from among the multiple protein sequences or multiple amino acid sequences applied above by evaluating the activity values predicted by the sequence-activity model for the multiple sequences. The methods also involve preparing and assaying the protein having the new protein sequence or a protein encoded by the new nucleic acid sequence.

In some embodiments, rather than simply synthesizing the single best-predicted protein, a combinatorial library of proteins is generated based on a sensitivity analysis of the best changes in the residue choices at each location in the protein. In this embodiment, the more sensitive a given residue choice is for the predicted protein, the greater the predicted fitness change will be. In some embodiments these sensitivities are from highest to lowest and the sensitivity scores are used to create combinatorial protein libraries in subsequent rounds (i.e., by incorporating those residues based on sensitivity). In some embodiments, in which a linear/non-interaction model is used, the sensitivity is identified by simply considering the size of the coefficient associated with a given residue term in the model. However, this is not possible for non-linear/interaction models. Instead, in embodiments utilizing non-linear/interaction models, the residue sensitivity is determined by using the model to calculate changes in activity when a single residue is varied in the "best" predicted sequence.

Some embodiments of the invention include selecting one or more positions in the protein sequence or nucleic acid sequence and conducting saturation mutagenesis at the one or more positions so identified. In some embodiments, the positions are selected by evaluating the coefficients of the terms of the sequence-activity model to identify one or more of the defined amino acids or nucleotides at the defined positions that contribute to the activity. Accordingly, in some embodiments, a round of directed evolution includes performing saturation mutagenesis on a protein sequence at positions selected using the sequence-activity models. In some embodiments involving models comprising one or more interaction terms, each interaction term relates to two or more residues. The methods involve applying mutagenesis simultaneously at the two or more interacting residues.

In some embodiments, residues are taken into consideration in the order in which they are ranked. In some embodiments, for each residue under consideration, the process determines whether to "toggle" that residue. The term "toggling" refers to including or excluding a specific amino acid residue at a specific position in the sequences of protein variants in the optimized library. For example, serine may appear in position 166 in one protein variant, whereas phenylalanine may appear in position 166 in another protein variant in the same library. Amino acid residues that do not vary between protein variant sequences in the training set typically remain fixed in the optimized library. However, this is not always the case, as there can be variation in the optimized libraries.

In some embodiments, an optimized protein variant library is designed such that all of the identified "high" ranking regression coefficient residues are fixed, and the remaining lower ranking regression coefficient residues are toggled. The rationale for this embodiment is that the local space surrounding the 'best' predicted protein should be searched. It is noted that the starting point "backbone" in which the toggles are introduced may be the best protein predicted by a model and/or an already validated 'best' protein from a screened library. Indeed, it is not intended that the starting point backbone be limited to any particular protein.

In an alternative embodiment, at least one or more, but not all of the identified high-ranking regression coefficient residues are fixed in the optimized library, and the others toggled. This approach is recommended in some embodiments, if there is a desire to not drastically change the context of the other amino acid residues by incorporating too many changes at one time. Again, the starting point for toggling may be the best set of residues as predicted by the model, a best validated protein from an existing library, or an "average" clone that models well. In the latter case, it may be desirable to toggle the residues predicted to be of higher importance, as a larger space should be explored in the search for activity hills previously omitted from the sampling. This type of library is typically more relevant in early rounds of library production, as it generates a more refined picture for subsequent rounds. It is also not intended that the starting point backbone be limited to any particular protein.

Some alternatives of the above embodiments involve different procedures for using residue importance (i.e., rankings) in determining which residues to toggle. In one such alternative embodiment, higher ranked residue positions are more aggressively favored for toggling. The information needed in this approach includes the sequence of a best protein from the training set, a PLS or PCR predicted best sequence, and a ranking of residues from the PLS or PCR model. In some embodiments, the "best" protein is a wet-lab validated "best" clone in the dataset (i.e., the clone with the highest measured function that still models well in that it falls relatively close to the predicted value in cross validation). The method compares each residue from this protein with the corresponding residue from a "best predicted" sequence having the highest value of the desired activity. If the residue with the highest load or regression coefficient is not present in the 'best' clone, the method introduces that position as a toggle position for the subsequent library. If the residue is present in the best clone, the method does not treat the position as a toggle position, and it will move to the next position in succession. The process is repeated for various residues, moving through successively lower load values, until a library of sufficient size is generated.

In some additional embodiments, a wet-lab validated 'best' (or one of the best) protein in the current optimized library (i.e., a protein with the highest, or one of the highest, measured function that still models well, i.e., falls relatively close to the predicted value in cross validation) serves as a backbone in which various changes are incorporated. In another approach, a wet-lab validated 'best' (or one of the best) protein in the current library that may not model well serves as a backbone where various changes are incorporated. In some other approaches, a sequence predicted by the sequence-activity model to have the highest value (or one of the highest values) of the desired activity serves as the backbone. In these approaches, the dataset for the "next generation" library (and possibly a corresponding model) is obtained by changing residues in at least one of the best proteins. In one embodiment, these changes comprise a systematic variation of the residues in the backbone. In some cases, the changes comprise various mutagenesis, recombination and/or subsequence selection techniques. Each of these may be performed in vitro, in vivo, and/or in silico. Indeed, it is not intended that the present invention be limited to any particular format, as any suitable format finds use.

In some embodiments, optimized protein variant libraries are generated using the recombination methods described herein, or alternatively, by gene synthesis methods, followed by in vivo or in vitro expression. In some embodiments, after the optimized protein variant libraries are screened for desired activity, they are sequenced. As indicated above, the activity and sequence information from the optimized protein variant library can be employed to generate another sequence-activity model from which a further optimized library can be designed, using the methods described herein. In one embodiment, all of the proteins from this new library are used as part of the dataset.

VIII. Sequencing Polynucleotides and Polypeptides

In some embodiments, polynucleotide and polypeptide sequence information is used to generate sequence-activity models or computational representations of active sites of protein variants. In some embodiments, polynucleotide and polypeptide sequence information is used in directed evolution processes to obtain protein variants of desired properties.

In various embodiments, the sequences of protein variants are ascertained from physical biomolecules by protein sequencing methods, some of which methods are further described below. Protein sequencing involves determining the amino acid sequence of a protein. Some protein sequencing techniques also determine conformation the protein adopts, and the extent to which it is complexed with any non-peptide molecules. Mass spectrometry and the Edman degradation reaction may be used to directly determine the sequence of amino acids of a protein.

The Edman degradation reaction allows the ordered amino acid composition of a protein to be discovered. In some embodiments, automated Edman sequencers can be used to determine the sequence of protein variants. Automated Edman sequencers are able to sequence peptides of increasingly longer sequences, e.g., up to approximately 50 amino acids long. In some embodiments, a protein sequencing process implementing Edman degradation involves one or more of the following:

- Break disulfide bridges in the protein with a reducing agent, e.g., 2-mercaptoethanol. A protecting group such as iodoacetic acid may be used to prevent bonds from re-forming.
- Separate and purify individual chains of the protein complex if there are more than one.
- Determine the amino acid composition of each chain
- Determine the terminal amino acids of each chain
- Break each chain into fragments, e.g., fragments under 50 amino acids long.
- Separate and purify the fragments
- Determine the sequence of each fragment using the Edman degradation reaction
- Repeat the above steps applying a different pattern of cleavage to provide additional read(s) of amino acid sequences Construct the sequence of the overall protein from amino acid sequence reads.

In various implementations, peptides longer than about 50-70 amino acids are to be broken up into small fragments to facilitate sequencing by Edman reactions. Digestion of longer sequences can be performed by endopeptidases such as trypsin or pepsin, or by chemical reagents such as cyanogen bromide. Different enzymes give different cleavage patterns, and the overlap between fragments can be used to construct an overall sequence.

During the Edman degradation reaction, the peptide to be sequenced is adsorbed onto a solid surface of a substrate. In some embodiments, one suitable substrate is glass fiber coated with polybrene, a cationic polymer. The Edman reagent, phenylisothiocyanate (PITC), is added to the adsorbed peptide, together with a mildly basic buffer solution of trimethylamine. This reaction solution reacts with the amine group of the N-terminal amino acid. The terminal amino acid can then be selectively detached by the addition of anhydrous acid. The derivative then isomerises to give a substituted phenylthiohydantoin, which can be washed off and identified by chromatography. Then the cycle can be repeated.

In some embodiments, mass spectrometry can be used to determine an amino acid sequence by determining the mass-to-charge ratios of fragments of the amino acid sequence. The mass spectrum including peaks corresponding to multiply charged fragments can be determined, where the distance between the peaks corresponding to different isotope is inversely proportional to the charge on the fragment. The mass spectrum is analyzed, e.g., by comparison against a database of previously sequenced proteins to determine the sequences of the fragments. This process is then repeated with a different digestion enzyme, and the overlaps in the sequences are used to construct a complete amino acid sequence.

Peptides are often easier to prepare and analyze for mass spectrometry than whole proteins. In some embodiments, electrospray ionization is used for delivering the peptides to the spectrometer. The protein is digested by an endoprotease, and the resulting solution is passed through a high-pressure liquid chromatography column. At the end of this column, the solution is sprayed into the mass spectrometer, the solution being charged with a positive potential. The charge on solution droplets causes them to fragment into single ions. The peptides are then fragmented and the mass-to-charge ratios of the fragments measured.

It is also possible to indirectly determine an amino acid sequence from the DNA or mRNA sequence encoding the protein. Nucleic acid sequencing methods, e.g., various next generation sequencing methods, may be used to determine DNA or RNA sequences. In some implementations, a protein sequence is newly isolated without knowledge of the nucleotides encoding the protein. In such implementations, one may first determine a short polypeptide sequence using one of the direct protein sequencing methods. A complementary marker for the protein's RNA can be determined from this short sequence. This can then be used to isolate the mRNA coding for the protein, which can then be replicated in a polymerase chain reaction to yield a significant amount of DNA, which can then be sequenced using DNA sequencing methods. The amino acid sequence of the protein can then be deduced from the DNA sequence. In the deduction, it is necessary to take into account the amino acids removed after the mRNA has been translated.

In various embodiments, the sequence information of polynucleotides is used to generate sequence-activity models or computational representation of protein activity sites. The nucleic acid sequence information can be ascertained from physical biomolecules by nucleic acid sequencing methods, some of which methods are further described below.

In one or more embodiments, sequence data can be obtained using bulk sequencing methods including, for example, Sanger sequencing or Maxam-Gilbert sequencing, which are considered the first generation sequencing methods. Sanger sequencing, which involves using labeled dideoxy chain terminators, is well known in the art; see, e.g., Sanger et al., Proceedings of the National Academy of Sciences of the United States of America 74, 5463-5467 (1997). Maxam-Gilbert sequencing, which involves performing multiple partial chemical degradation reactions on fractions of the nucleic acid sample followed by detection and analysis of the fragments to infer the sequence, is also well known in the art; see, e.g., Maxam et al., Proceedings of the National Academy of Sciences of the United States of America 74, 560-564 (1977). Another bulk sequencing method is sequencing by hybridization, in which the sequence of a sample is deduced based on its hybridization properties to a plurality of sequences, e.g., on a microarray or gene chip; see, e.g., Drmanac, et al., Nature Biotechnology 16, 54-58 (1998).

In one or more embodiments, sequence data is obtained using next-generation sequencing methods. Next-generation sequencing is also referred to as high-throughput sequencing. The techniques parallelize the sequencing process, producing thousands or millions of sequences at once. Examples of suitable next-generation sequencing methods include, but are not limited to, single molecule real-time sequencing (e.g., Pacific Biosciences of Menlo Park, Calif.), Ion semiconductor sequencing (e.g., Ion Torrent of South San Francisco, Calif.), pyrosequencing (e.g., 454 of Branford, Conn.), sequencing by ligation (e.g., SOLiD sequencing owned by Life Technologies of Carlsbad, Calif.), sequencing by synthesis and reversible terminator (e.g., Illumina of San Diego, Calif.), nucleic acid imaging technologies such as transmission electron microscopy, and the like.

In general, next-generation sequencing methods typically use an in vitro cloning step to amplify individual DNA molecules. Emulsion PCR (emPCR) isolates individual DNA molecules along with primer-coated beads in aqueous droplets within an oil phase. PCR produces copies of the DNA molecule, which bind to primers on the bead, followed by immobilization for later sequencing. emPCR is used in the methods by Marguilis et al. (commercialized by 454 Life Sciences, Branford, Conn.), Shendure and Porreca et al. (also known as "polony sequencing") and SOLiD sequencing, (Applied Biosystems Inc., Foster City, Calif.). See M. Margulies, et al. (2005) "Genome sequencing in microfabricated high-density picolitre reactors" Nature 437: 376-380; J. Shendure, et al. (2005) "Accurate Multiplex Polony Sequencing of an Evolved Bacterial Genome" Science 309 (5741): 1728-1732. In vitro clonal amplification can also be carried out by "bridge PCR," where fragments are amplified upon primers attached to a solid surface. Braslaysky et al. developed a single-molecule method (commercialized by Helicos Biosciences Corp., Cambridge, Mass.) that omits this amplification step, directly fixing DNA molecules to a surface. I. Braslaysky, et al. (2003) "Sequence information can be obtained from single DNA molecules" Proceedings of the National Academy of Sciences of the United States of America 100: 3960-3964.

DNA molecules that are physically bound to a surface can be sequenced in parallel. In "sequencing by synthesis," a complementary strand is built based on the sequence of a template strand using a DNA polymerase. like dye-termination electrophoretic sequencing, Reversible terminator methods (commercialized by Illumina, Inc., San Diego, Calif. and Helicos Biosciences Corp., Cambridge, Mass.) use reversible versions of dye-terminators, adding one nucleotide at a time, and detect fluorescence at each position in real time, by repeated removal of the blocking group to allow polymerization of another nucleotide. "Pyrosequencing" also uses DNA polymerization, adding one nucleotide at a time and detecting and quantifying the number of nucleotides added to a given location through the light emitted by the release of attached pyrophosphates (commercialized by 454 Life Sciences, Branford, Conn.). See M. Ronaghi, et al. (1996). "Real-time DNA sequencing using detection of pyrophosphate release" Analytical Biochemistry 242: 84-89.

Specific examples of next-generation sequencing methods are described in further details below. One or more implementations of the current invention may use one or more of the following sequencing methods without deviating from the principles of the invention.

Single molecule real time sequencing (also known as SMRT) is a parallelized single molecule DNA sequencing by synthesis technology developed by Pacific Biosciences. Single molecule real time sequencing utilizes the zero-mode waveguide (ZMW). A single DNA polymerase enzyme is affixed at the bottom of a ZMW with a single molecule of DNA as a template. The ZMW is a structure that creates an illuminated observation volume that is small enough to observe only a single nucleotide of DNA (also known as a base) being incorporated by DNA polymerase. Each of the four DNA bases is attached to one of four different fluorescent dyes. When a nucleotide is incorporated by the DNA polymerase, the fluorescent tag is cleaved off and diffuses out of the observation area of the ZMW where its fluorescence is no longer observable. A detector detects the fluorescent signal of the nucleotide incorporation, and the base call is made according to the corresponding fluorescence of the dye.

Another single molecule sequencing technology applicable is the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

Ion Semiconductor Sequencing is a method of DNA sequencing based on the detection of hydrogen ions that are released during the polymerization of DNA. This is a method of "sequencing by synthesis," during which a complementary strand is built based on the sequence of a template strand. A microwell containing a template DNA strand to be sequenced is flooded with a single species of deoxyribonucleotide triphosphate (dNTP). If the introduced dNTP is complementary to the leading template nucleotide, it is incorporated into the growing complementary strand. This causes the release of a hydrogen ion that triggers an ISFET ion sensor, which indicates that a reaction has occurred. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. Ion semiconductor sequencing may also be referred to as ion torrent sequencing, pH-mediated sequencing, silicon sequencing, or semiconductor sequencing.

In pyrosequencing, the pyrophosphate ion released by the polymerization reaction is reacted with adenosine 5' phosphosulfate by ATP sulfurylase to produce ATP; the ATP then drives the conversion of luciferin to oxyluciferin plus light by luciferase. As the fluorescence is transient, no separate step to eliminate fluorescence is necessary in this method. One type of deoxyribonucleotide triphosphate (dNTP) is added at a time, and sequence information is discerned according to which dNTP generates significant signal at a reaction site. The commercially available Roche GS FLX instrument acquires sequence using this method. This technique and applications thereof are discussed in detail, for example, in Ronaghi et al., Analytical Biochemistry 242, 84-89 (1996) and Margulies et al., Nature 437, 376-380 (2005) (corrigendum at Nature 441, 120 (2006)). A commercially available pyrosequencing technology is 454 sequencing (Roche) (e.g. as described in Margulies, M. et al. Nature 437:376-380 [2005]).

In ligation sequencing, a ligase enzyme is used to join a partially double-stranded oligonucleotide with an overhang to the nucleic acid being sequenced, which has an overhang; in order for ligation to occur, the overhangs must be complementary. The bases in the overhang of the partially double-stranded oligonucleotide can be identified according to a fluorophore conjugated to the partially double-stranded oligonucleotide and/or to a secondary oligonucleotide that hybridizes to another part of the partially double-stranded oligonucleotide. After acquisition of fluorescence data, the ligated complex is cleaved upstream of the ligation site, such as by a type Hs restriction enzyme, for example, Bbvl, which cuts at a site fixed distance from its recognition site (which was included in the partially double stranded oligonucleotide). This cleavage reaction exposes a new overhang just upstream of the previous overhang, and the process is repeated. This technique and applications thereof are discussed in detail, for example, in Brenner et al., Nature Biotechnology 18, 630-634 (2000), In some embodiments, ligation sequencing is adapted to the methods of the invention by obtaining a rolling circle amplification product of a circular add molecule, and using the rolling circle amplification product as the template for ligation sequencing.

A commercially available example of ligation sequencing technology is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In reversible terminator sequencing, a fluorescent dye-labeled nucleotide analog that is a reversible chain terminator due to the presence of a blocking group is incorporated in a single-base extension reaction. The identity of the base is determined according to the fluorophore; in other words, each base is paired with a different fluorophore. After fluorescence/sequence data is acquired, the fluorophore and the blocking group are chemically removed, and the cycle is repeated to acquire the next base of sequence information. The Illumina GA instrument operates by this method. This technique and applications thereof are discussed in detail, for example, in Ruparel et al., Proceedings of the National Academy of Sciences of the United States of America 102, 5932-5937 (2005), and Harris et al., Science 320, 106-1109 (2008).

A commercially available example of reversible terminator sequencing method is Illumina's sequencing-by-synthesis and reversible terminator-based sequencing (e.g. as described in Bentley et al., Nature 6:53-59 [2009]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing 1,000 copies of the same template. The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp e.g. 36 bp, are aligned against a repeat-masked reference genome and unique mapping of the short sequence reads to the reference genome are identified using specially developed data analysis pipeline software. Non-repeat-masked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length e.g. 36 bp, are mapped to a known reference genome are counted.

In nanopore sequencing, a single stranded nucleic acid molecule is threaded through a pore, e.g., using an electrophoretic driving force, and sequence is deduced by analyzing data obtained as the single stranded nucleic acid molecule passes through the pore. The data can be ion current data, wherein each base alters the current, e.g., by partially blocking the current passing through the pore to a different, distinguishable degree.

In another illustrative, but non-limiting, embodiment, the methods described herein comprises obtaining sequence information using transmission electron microscopy (TEM). The method comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445.

In another illustrative, but non-limiting, embodiment, the methods described herein comprises obtaining sequence information using third-generation sequencing. In third-generation sequencing, a slide with an aluminum coating with many small (~50 nm) holes is used as a zero mode waveguide (see, e.g., Levene et al., Science 299, 682-686 (2003)). The aluminum surface is protected from attachment of DNA polymerase by polyphosphonate chemistry, e.g., polyvinylphosphonate chemistry (see, e.g., Korlach et at, Proceedings of the National Academy of Sciences of the United States of America 105, 1176-1181 (2008)). This results in preferential attachment of the DNA polymerase molecules to the exposed silica in the holes of the aluminum coating. This setup allows evanescent wave phenomena to be used to reduce fluorescence background, allowing the use of higher concentrations of fluorescently labeled dNTPs. The fluorophore is attached to the terminal phosphate of the dNTPs, such that fluorescence is released upon incorporation of the dNTP, but the fluorophore does not remain attached to the newly incorporated nucleotide, meaning that the complex is immediately ready for another round of incorporation. By this method, incorporation of dNTPs into an individual primer-template complexes present in the holes of the aluminum coating can be detected. See, e.g., Eid et al., Science 323, 133-138 (2009).

IX. Assaying Gene and Protein Variants

In some embodiments, polynucleotides generated in connection with methods of the present invention are optionally cloned into cells to express protein variants for activity screening (or used in in vitro transcription reactions to make products which are screened). Furthermore, the nucleic acids encoding protein variants can be enriched, sequenced, expressed, amplified in vitro or treated in any other common recombinant method.

General texts that describe molecular biological techniques useful herein, including cloning, mutagenesis, library construction, screening assays, cell culture and the like include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (2nd Ed.), Vol. 1-3, Cold Spring Harbor Laboratory, Cold Spring Harbor, N.Y., 1989 (Sambrook) and Current Protocols in Molecular Biology, F. M. Ausubel et al., eds., Current Protocols, a joint venture between Greene Publishing Associates, Inc. and John Wiley & Sons, Inc., New York (supplemented through 2000) (Ausubel)). Methods of transducing cells, including plant and animal cells, with nucleic acids are generally available, as are methods of expressing proteins encoded by such nucleic acids. In addition to Berger, Ausubel and Sambrook, useful general references for culture of animal cells include Freshney (Culture of Animal Cells, a Manual of Basic Technique, third edition Wiley-Liss, New York (1994)) and the references cited therein, Humason (Animal Tissue Techniques, fourth edition W.H. Freeman and Company (1979)) and Ricciardelli, et al., In Vitro Cell Dev. Biol. 25:1016-1024 (1989). References for plant cell cloning, culture and regeneration include Payne et al. (1992) Plant Cell and Tissue Culture in Liquid Systems John Wiley & Sons, Inc. New York, N.Y. (Payne); and Gamborg and Phillips (eds) (1995) Plant Cell, Tissue and Organ Culture; Fundamental Methods Springer Lab Manual, Springer-Verlag (Berlin Heidelberg New York) (Gamborg). A variety of Cell culture media are described in Atlas and Parks (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc. (St Louis, Mo.) (Sigma-LSRCCC) and, e.g., the Plant Culture Catalogue and supplement (1997) also from Sigma-Aldrich, Inc (St Louis, Mo.) (Sigma-PCCS).

Examples of techniques sufficient to direct persons of skill through in vitro amplification methods, useful e.g., for amplifying oligonucleotide recombined nucleic acids including polymerase chain reactions (PCR), ligase chain reactions (LCR), Qβ-replicase amplifications and other RNA polymerase mediated techniques (e.g., NASBA). These techniques are found in Berger, Sambrook, and Ausubel, supra, as well as in Mullis et al., (1987) U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990) C&EN 36-47; The Journal Of NIH Research (1991) 3, 81-94; Kwoh et al. (1989) Proc. Natl. Acad. Sci. USA 86, 1173; Guatelli et al. (1990) Proc. Natl. Acad. Sci. USA 87, 1874; Lomell et al. (1989) J. Clin. Chem 35, 1826; Landegren et al., (1988) Science 241, 1077-1080; Van Brunt (1990) Biotechnology 8, 291-294; Wu and Wallace, (1989) Gene 4, 560; Barringer et al. (1990) Gene 89, 117, and Sooknanan and Malek (1995) Biotechnology 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

In one preferred method, reassembled sequences are checked for incorporation of family-based recombination oligonucleotides. This can be done by cloning and sequencing the nucleic acids, and/or by restriction digestion, e.g., as essentially taught in Sambrook, Berger and Ausubel, supra. In addition, sequences can be PCR amplified and sequenced directly. Thus, in addition to, e.g., Sambrook, Berger, Ausubel and Innis (supra), additional PCR sequencing methodologies are also particularly useful. For example, direct sequencing of PCR generated amplicons by selectively incorporating boronated nuclease resistant nucleotides into the amplicons during PCR and digestion of the amplicons with a nuclease to produce sized template fragments has been performed (Porter et al. (1997) Nucleic Acids Research 25(8):1611-1617). In the methods, four PCR reactions on a template are performed, in each of which one of the nucleotide triphosphates in the PCR reaction mixture is partially substituted with a 2'deoxynucleoside 5'-[P-borano]-triphosphate. The boronated nucleotide is stochastically incorporated into PCR products at varying positions along the PCR amplicon in a nested set of PCR fragments of the template. An exonuclease that is blocked by incorporated boronated nucleotides is used to cleave the PCR amplicons. The cleaved amplicons are then separated by size using polyacrylamide gel electrophoresis, providing the sequence of the amplicon. An advantage of this method is that it uses fewer biochemical manipulations than performing standard Sanger-style sequencing of PCR amplicons.

Synthetic genes are amenable to conventional cloning and expression approaches; thus, properties of the genes and proteins they encode can readily be examined after their expression in a host cell. Synthetic genes can also be used to generate polypeptide products by in vitro (cell-free) transcription and translation. Polynucleotides and polypeptides can thus be examined for their ability to bind a variety of predetermined ligands, small molecules and ions, or polymeric and heteropolymeric substances, including other proteins and polypeptide epitopes, as well as microbial cell walls, viral particles, surfaces and membranes.

For example, many physical methods can be used for detecting polynucleotides encoding phenotypes associated with catalysis of chemical reactions by either polynucleotides directly, or by encoded polypeptides. Solely for the purpose of illustration, and depending on the specifics of particular pre-determined chemical reactions of interest, these methods may include a multitude of techniques known in the art which account for a physical difference between substrate(s) and product(s), or for changes in the reaction media associated with chemical reaction (e.g. changes in electromagnetic emissions, adsorption, dissipation, and fluorescence, whether UV, visible or infrared (heat)). These methods also can be selected from any combination of the following: mass-spectrometry; nuclear magnetic resonance; isotopically labeled materials, partitioning and spectral methods accounting for isotope distribution or labeled product formation; spectral and chemical methods to detect accompanying changes in ion or elemental compositions of reaction product(s) (including changes in pH, inorganic and organic ions and the like). Other methods of physical assays, suitable for use in the methods herein, can be based on the use of biosensors specific for reaction product(s), including those comprising antibodies with reporter properties, or those based on in vivo affinity recognition coupled with expression and activity of a reporter gene. Enzyme-coupled assays for reaction product detection and cell life-death-growth selections in vivo can also be used where appropriate. Regardless of the specific nature of the physical assays, they all are used to select a desired activity, or combination of desired activities, provided or encoded by a biomolecule of interest.

The specific assay used for the selection will depend on the application. Many assays for proteins, receptors, ligands, enzymes, substrates and the like are known. Formats include binding to immobilized components, cell or organismal viability, production of reporter compositions, and the like.

High throughput assays are particularly suitable for screening libraries employed in the present invention. In high throughput assays, it is possible to screen up to several thousand different variants in a single day. For example, each well of a microtiter plate can be used to run a separate assay, or, if concentration or incubation time effects are to be observed, every 5-10 wells can test a single variant (e.g., at different concentrations). Thus, a single standard microtiter plate can assay about 100 (e.g., 96) reactions. If 1536 well plates are used, then a single plate can easily assay from about 100 to about 1500 different reactions. It is possible to assay several different plates per day; assay screens for up to about 6,000-20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Mountain View, Calif.) which can provide very high throughput microfluidic assay methods.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols for various high throughput screening assays. Thus, for example, Zymark Corp. provides technical bulletins describing screening systems for detecting the modulation of gene transcription, ligand binding, and the like.

A variety of commercially available peripheral equipment and software is available for digitizing, storing and analyzing a digitized video or digitized optical or other assay images, e.g., using PC (Intel x86 or pentium chip-compatible MAC OS, WINDOWS™ family, or UNIX based (e.g., SUN™ work station) computers.

Systems for analysis typically include a digital computer specifically programmed to perform specialized algorithms using software for directing one or more steps of one or more of the methods herein, and, optionally, also include, e.g., a next generation sequencing platform control software, high-throughput liquid control software, image analysis software, data interpretation software, a robotic liquid control armature for transferring solutions from a source to a destination operably linked to the digital computer, an input device (e.g., a computer keyboard) for entering data to the digital computer to control operations or high throughput liquid transfer by the robotic liquid control armature and, optionally, an image scanner for digitizing label signals from labeled assay components. The image scanner can interface with image analysis software to provide a measurement of probe label intensity. Typically, the probe label intensity measurement is interpreted by the data interpretation software to show whether the labeled probe hybridizes to the DNA on the solid support.

In some embodiments, cells, viral plaques, spores or the like, comprising in vitro oligonucleotide-mediated recombination products or physical embodiments of in silico recombined nucleic acids, can be separated on solid media to produce individual colonies (or plaques). Using an automated colony picker (e.g., the Q-bot, Genetix, U.K.), colonies or plaques are identified, picked, and up to 10,000 different mutants inoculated into 96 well microtiter dishes containing two 3 mm glass balls/well. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each parameter can be controlled and optimized.

The uniform process of automated colony picking such as the Q-bot decreases human handling error and increases the rate of establishing cultures (roughly 10,000/4 hours). These cultures are optionally shaken in a temperature and humidity controlled incubator. Optional glass balls in the microtiter plates act to promote uniform aeration of cells and the dispersal of cellular (e.g., mycelial) fragments similar to the blades of a fermentor. Clones from cultures of interest can be isolated by limiting dilution. As also described supra, plaques or cells constituting libraries can also be screened directly for the production of proteins, either by detecting hybridization, protein activity, protein binding to antibodies, or the like. To increase the chances of identifying a pool of sufficient size, a prescreen that increases the number of mutants processed by 10-fold can be used. The goal of the primary screen is to quickly identify mutants having equal or better product titers than the parent strain(s) and to move only these mutants forward to liquid cell culture for subsequent analysis.

One approach to screening diverse libraries is to use a massively parallel solid-phase procedure to screen cells expressing polynucleotide variants, e.g., polynucleotides that encode enzyme variants. Massively parallel solid-phase screening apparatus using absorption, fluorescence, or FRET are available. See, e.g., U.S. Pat. No. 5,914,245 to Bylina, et al. (1999); see also, http://wwwl.lkairos-scientific.com/; Youvan et al. (1999) "Fluorescence Imaging Micro-Spectrophotometer (FIMS)" Biotechnology et alia, <wwwl.let-al.com>1:1-16; Yang et al. (1998) "High Resolution Imaging Microscope (HIRIM)" Biotechnology et alia, <wwwl.let-al.com>4:1-20; and Youvan et al. (1999) "Calibration of Fluorescence Resonance Energy Transfer in Microscopy Using Genetically Engineered GFP Derivatives on Nickel Chelating Beads" posted at wwwl.lkairos-scientific.com. Following screening by these techniques, molecules of interest are typically isolated, and optionally sequenced using methods that are known in the art. The sequence information is then used as set forth herein to design a new protein variant library.

Similarly, a number of well-known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual synthetic operations performed by a scientist. Any of the above devices are suitable for use with the present invention, e.g., for high-throughput screening of molecules encoded by nucleic acids evolved as described herein. The nature and implementation of modifications to these devices (if any) so that they can operate as discussed herein will be apparent to persons skilled in the relevant art.

X. Digital Apparatus and Systems

As should be apparent, embodiments described herein employ processes acting under control of instructions and/or data stored in or transferred through one or more computer systems. Embodiments disclosed herein also relate to apparatus for performing these operations. In some embodiments, the apparatus is specially designed and/or constructed for the required purposes, or it may be a general-purpose computer selectively activated or reconfigured by a computer program and/or data structure stored in the computer. The processes provided by the present disclosure are not inherently related to any particular computer or other specific apparatus. In particular, various general-purpose machines find use with programs written in accordance with the teachings herein. However, in some embodiments, a specialized apparatus is constructed to perform the required method operations. One embodiment of a particular structure for a variety of these machines is described below.

In addition, certain embodiments of the present disclosure relate to computer readable media or computer program products that include program instructions and/or data (including data structures) for performing various computer-implemented operations. Examples of computer-readable media include, but are not limited to, magnetic media such as hard disks; optical media such as CD-ROM devices and holographic devices; magneto-optical media; and semiconductor memory devices such as flash memory. Hardware devices such as read-only memory devices (ROM) and random access memory devices (RAM) may be configured to store program instructions. Hardware devices such as application-specific integrated circuits (ASICs) and programmable logic devices (PLDs) may be configured to store program instructions and execute. It is not intended that the present disclosure be limited to any particular computer-readable media or any other computer program products that include instructions and/or data for performing computer-implemented operations.

Examples of program instructions include, but are not limited to low-level codes such as those produced by a compiler, and files containing higher level code that may be executed by the computer using an interpreter. Further, the program instructions include, but are not limited to machine code, source code and any other code that directly or indirectly controls operation of a computing machine in accordance with the present disclosure. The code may specify input, output, calculations, conditionals, branches, iterative loops, etc.

Figure 4:
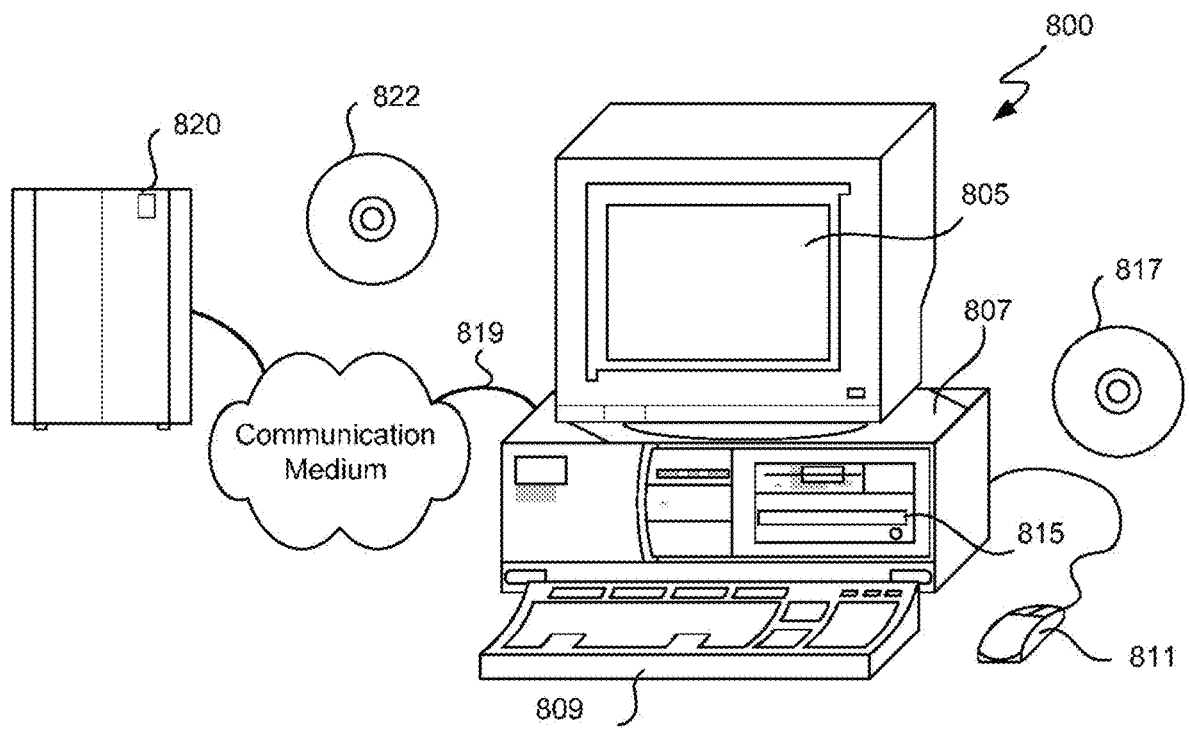
FIG. 4 shows an exemplary digital device that can be implemented according to some embodiments.

In one illustrative example, code embodying methods disclosed herein are embodied in a fixed media or transmissible program component containing logic instructions and/or data that when loaded into an appropriately configured computing device causes the device to perform a simulated genetic operation (GO) on one or more character string(s). FIG. 4 shows an example digital device 800 that is a logical apparatus that can read instructions from media 817, network port 819, user input keyboard 809, user input 811, or other inputting means. Apparatus 800 can thereafter use those instructions to direct statistical operations in data space, e.g., to construct one or more data set(s) (e.g., to determine a plurality of representative members of the data space). One type of logical apparatus that can embody disclosed embodiments is a computer system as in computer system 800 comprising CPU 807, optional user input devices keyboard 809, and GUI pointing device 811, as well as peripheral components such as disk drives 815 and monitor 805 (which displays GO modified character strings and provides for simplified selection of subsets of such character strings by a user. Fixed media 817 is optionally used to program the overall system and can include, e.g., a disk-type optical or magnetic media or other electronic memory storage element. Communication port 819 can be used to program the system and can represent any type of communication connection.

Certain embodiments can also be embodied within the circuitry of an application specific integrated circuit (ASIC) or programmable logic device (PLD). In such a case, the embodiments are implemented in a computer readable descriptor language that can be used to create an ASIC or PLD. Some embodiments of the present disclosure are implemented within the circuitry or logic processors of a variety of other digital apparatus, such as PDAs, laptop computer systems, displays, image editing equipment, etc.

In some embodiments, the present disclosure relates to a computer program product comprising one or more computer-readable storage media having stored thereon computer-executable instructions that, when executed by one or more processors of a computer system, cause the computer system to implement a method for virtual screening of protein variants and/or in silico directed evolution of proteins having desired activity. Such a method may be any method described herein such as those encompassed by the Figures and pseudocode. In some embodiments, for example, the method receives sequence data for a plurality of enzymes, creates three-dimensional homology models of biological molecules, docks the homology models of enzymes with one or more computational representations of substrates, and derives structural data regarding geometrical parameters with reference to the enzymes and substrates. In some embodiments, the method can further develop sequence activity models by filtering data with reference to the modeled structural data. The variant libraries can be used in re-iterative directed evolution, which can result in enzymes of desired beneficial properties.

In some embodiments, the docking of the homology models of enzymes with one or more computational representations of substrates is conducted by a docking program on a computer system that uses a computational representation of a ligand and computational representations of the binding sites of a plurality of variants in manners described herein. In various embodiments, the docking program evaluates the binding energy between a pose of the substrate and the enzyme. For a protein variant that successfully docks with the ligand, the system determines geometrical values with regard to the participating ligand and protein.

In various embodiments, the computer system constructs a sequence activity model by training a support vector machine. In various embodiments, the computer system uses genetic algorithms to filter out uninformative data, thereby providing a subset of data for training the support vector machine.

XI. Embodiments in Websites and Cloud Computing

The Internet includes computers, information appliances, and computer networks that are interconnected through communication links. The interconnected computers exchange information using various services, such as electronic mail, ftp, the World Wide Web ("WWW") and other services, including secure services. The WWW service can be understood as allowing a server computer system (e.g., a Web server or a Web site) to send web pages of information to a remote client information appliance or computer system. The remote client computer system can then display the web pages. Generally, each resource (e.g., computer or web page) of the WWW is uniquely identifiable by a Uniform Resource Locator ("URL"). To view or interact with a specific web page, a client computer system specifies a URL for that web page in a request. The request is forwarded to a server that supports that web page. When the server receives the request, it sends that web page to the client information system. When the client computer system receives that web page, it can display the web page using a browser or can interact with the web page or interface as otherwise provided. A browser is a logic module that effects the requesting of web pages and displaying or interacting with web pages.

Currently, displayable web pages are typically defined using a Hyper Text Markup Language ("HTML"). HTML provides a standard set of tags that define how a web page is to be displayed. An HTML document contains various tags that control the displaying of text, graphics, controls, and other features. The HTML document may contain URLs of other Web pages available on that server computer system or other server computer systems. URLs can also indicate other types of interfaces, including such things as CGI scripts or executable interfaces, that information appliances use to communicate with remote information appliances or servers without necessarily displaying information to a user.

The Internet is especially conducive to providing information services to one or more remote customers. Services can include items (e.g., music or stock quotes) that are delivered electronically to a purchaser over the Internet. Services can also include handling orders for items (e.g., groceries, books, or chemical or biologic compounds, etc.) that may be delivered through conventional distribution channels (e.g., a common carrier). Services may also include handling orders for items, such as airline or theater reservations, that a purchaser accesses at a later time. A server computer system may provide an electronic version of an interface that lists items or services that are available. A user or a potential purchaser may access the interface using a browser and select various items of interest. When the user has completed selecting the items desired, the server computer system may then prompt the user for information needed to complete the service. This transaction-specific order information may include the purchaser's name or other identification, an identification for payment (such as a corporate purchase order number or account number), or additional information needed to complete the service, such as flight information.

Among services of particular interest that can be provided over the internet and over other networks are biological data and biological databases. Such services include a variety of services provided by the National Center for Biotechnology Information (NCBI) of the National Institutes of Health (NIH). NCBI is charged with creating automated systems for storing and analyzing knowledge about molecular biology, biochemistry, and genetics; facilitating the use of such databases and software by the research and medical community; coordinating efforts to gather biotechnology information both nationally and internationally; and performing research into advanced methods of computer-based information processing for analyzing the structure and function of biologically important molecules.

NCBI holds responsibility for the GenBank® DNA sequence database. The database has been constructed from sequences submitted by individual laboratories and by data exchange with the international nucleotide sequence databases, the European Molecular Biology Laboratory (EMBL) and the DNA Database of Japan (DDBJ), and includes patent sequence data submitted to the U.S. Patent and Trademark Office. In addition to GenBank®, NCBI supports and distributes a variety of databases for the medical and scientific communities. These include the Online Mendelian Inheritance in Man (OMIM), the Molecular Modeling Database (MMDB) of 3D protein structures, the Unique Human Gene Sequence Collection (UniGene), a Gene Map of the Human Genome, the Taxonomy Browser, and the Cancer Genome Anatomy Project (CGAP), in collaboration with the National Cancer Institute. Entrez is NCBI's search and retrieval system that provides users with integrated access to sequence, mapping, taxonomy, and structural data. Entrez also provides graphical views of sequences and chromosome maps. A feature of Entrez is the ability to retrieve related sequences, structures, and references. BLAST, as described herein, is a program for sequence similarity searching developed at NCBI for identifying genes and genetic features that can execute sequence searches against the entire DNA database. Additional software tools provided by NCBI include: Open Reading Frame Finder (ORF Finder), Electronic PCR, and the sequence submission tools, Sequin and BankIt. NCBI's various databases and software tools are available from the WWW or by FTP or by e-mail servers. Further information is available at www1.lncbi.nlm.nih.gov.

Some biological data available over the internet is data that is generally viewed with a special browser "plug-in" or other executable code. One example of such a system is CHIME, a browser plug-in that allows an interactive virtual 3-dimensional display of molecular structures, including biological molecular structures. Further information regarding CHIME is available at www1.lmdlchime.com/chime/.

A variety of companies and institutions provide online systems for ordering biological compounds. Examples of such systems can be found at www1.lgenosys.com/oligo_custinfo.cfm or www1.lgenomictechnologies.com/Qbrowser2_FP.html. Typically, these systems accept some descriptor of a desired biological compound (such as an oligonucleotide, DNA strand, RNA strand, amino acid sequence, etc.) and then the requested compound is manufactured and is shipped to the customer in a liquid solution or other appropriate form.

As the methods provides herein may be implemented on a website as further described below, the computational results or physical results involving polypeptides or polynucleotides produced by some embodiments of the disclosure may be provided through the internet in ways similar to the biological information and compounds described above.

To further illustrate, the methods of this invention can be implemented in a localized or distributed computing environment. In a distributed environment, the methods may be implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an Intranet or an Internet.

In one internet embodiment, a client system typically executes a Web browser and is coupled to a server computer executing a Web server. The Web browser is typically a program such as IBM's Web Explorer, Microsoft's Internet explorer, NetScape, Opera, or Mosaic. The Web server is typically, but not necessarily, a program such as IBM's HTTP Daemon or other www daemon (e.g., LINUX-based forms of the program). The client computer is bi-directionally coupled with the server computer over a line or via a wireless system. In turn, the server computer is bi-directionally coupled with a website (server hosting the website) providing access to software implementing the methods of this invention.

As mentioned, a user of a client connected to the Intranet or Internet may cause the client to request resources that are part of the web site(s) hosting the application(s) providing an implementation of the methods of this invention. Server program(s) then process the request to return the specified resources (assuming they are currently available). The standard naming convention (i.e., Uniform Resource Locator ("URL")) encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

The software implementing the method(s) of this invention can run locally on the server hosting the website in a true client-server architecture. Thus, the client computer posts requests to the host server which runs the requested process(es) locally and then downloads the results back to the client. Alternatively, the methods of this invention can be implemented in a "multi-tier" format in which a component of the method(s) are performed locally by the client. This can be implemented by software downloaded from the server on request by the client (e.g. a Java application) or it can be implemented by software "permanently" installed on the client.

In one embodiment the application(s) implementing the methods of this invention are divided into frames. In this paradigm, it is helpful to view an application not so much as a collection of features or functionality but, instead, as a collection of discrete frames or views. A typical application, for instance, generally includes a set of menu items, each of with invokes a particular frame—that is, a form which manifest certain functionality of the application. With this perspective, an application is viewed not as a monolithic body of code but as a collection of applets, or bundles of functionality. In this manner from within a browser, a user would select a Web page link which would, in turn, invoke a particular frame of the application (i.e., a sub-application). Thus, for example, one or more frames may provide functionality for inputting and/or encoding biological molecule(s) into one or more data spaces, while another frame provides tools for refining a model of the data space.

In certain embodiments, the methods of this invention are implemented as one or more frames providing, e.g., the following functionalit(ies): function(s) to encode two or more biological molecules into character strings to provide a collection of two or more different initial character strings wherein each of said biological molecules comprises a selected set of subunits; functions to select at least two substrings from the character strings; functions to concatenate the substrings to form one or more product strings about the same length as one or more of the initial character strings; functions to add (place) the product strings to a collection of strings; functions to create and manipulate computational representation/models of enzymes and substrates, functions to dock a computational representation of a substrate (e.g., a ligand) with the computational representation of an enzyme (e.g., a protein); functions to apply molecular dynamics to molecular models; functions to calculate various constraints between molecules that affect chemical reactions involving the molecules (e.g., distance or angle between a substrate moiety and an enzyme active site); and functions to implement any feature set forth herein.

One or more of these functionalities may also be implemented exclusively on a server or on a client computer. These functions, e.g., functions for creating or manipulating computational models of biological molecules, can provide one or more windows wherein the user can insert or manipulate representation(s) of biological molecules. In addition, the functions also, optionally, provides access to private and/or public databases accessible through a local network and/or the intranet whereby one or more sequences contained in the databases can be input into the methods of this invention. Thus, for example, in one embodiment, the user can, optionally, have the ability to request a search of GenBank® and input one or more of the sequences returned by such a search into an encoding and/or a diversity generating function.

Methods of implementing Intranet and/or Intranet embodiments of computational and/or data access processes are well known to those of skill in the art and are documented in great detail (see, e.g., Cluer et al. (1992) "A General Framework for the Optimization of Object-Oriented Queries," Proc SIGMOD International Conference on Management of Data, San Diego, Calif., Jun. 2-5, 1992, SIGMOD Record, vol. 21, Issue 2, June, 1992; Stonebraker, M., Editor; ACM Press, pp. 383-392; ISO-ANSI, Working Draft, "Information Technology-Database Language SQL," Jim Melton, Editor, International Organization for Standardization and American National Standards Institute, July 1992; Microsoft Corporation, "ODBC 2.0 Programmer's Reference and SDK Guide. The Microsoft Open Database Standard for Microsoft Windows.™ and Windows NT™, Microsoft Open Database Connectivity™ Software Development Kit," 1992, 1993, 1994 Microsoft Press, pp. 3-30 and 41-56; ISO Working Draft, "Database Language SQL-Part 2:Foundation (SQL/Foundation)," CD9075-2:199.chi.SQL, Sep. 11, 1997, and the like). Additional relevant details regarding web-based applications are found in WO 00/42559, entitled "METHODS OF POPULATING DATA STRUCTURES FOR USE IN EVOLUTIONARY SIMULATIONS," by Selifonov and Stemmer.

In some embodiments, the methods for exploring, screening, and/or developing polynucleotide or polypeptide sequences can be implemented as a multi-user system on a computer system with a plurality of processing units and memories distributed over a computer network, wherein the network may include intranet on LAN and/or the Internet. In some embodiments, the distributed computing architecture involves a "cloud," which is a collection of computer systems available over a computer network for computation and data storage. The computing environment involving a cloud is referred to as a cloud computing environment. In some embodiments, one or more users can access the computers of the cloud distributed over an intranet and/or the Internet. In some embodiments, a user may remotely access, through a web client, server computers that implement the methods for screening and/or developing protein variants described above.

In some embodiments involving a cloud computing environment, virtual machines (VMs) are provisioned on the server computers, and the results of the virtual machines can be sent back to the user. A virtual machine (VM) is a software-based emulation of a computer. Virtual machines may be based on specifications of a hypothetical computer or emulate the computer architecture and functions of a real world computer. The structure and functions of VMs are well known in the art. Typically, a VM is installed on a host platform that includes system hardware, and the VM itself includes virtual system hardware and guest software.

The host system hardware for a VM includes one or more Central Processing Units (CPUs), memory, one or more hard disks and various other devices. The VM's virtual system hardware includes one or more virtual CPUs, virtual memory, one or more virtual hard disks and one or more virtual devices. The VM's guest software includes guest system software and guest applications. In some implementations, guest system software includes a guest operating system with drivers for virtual devices. In some implementations, the VM's guest applications include at least one instance of a virtual protein screening system as described above.

In some embodiments, the number of provisioned VMs can be scaled to the computational load of the problem to be solved. In some embodiments, a user can request a virtual machine from a cloud, the VM including a virtual screening system. In some embodiments, the cloud computing environment can provision a VM based on the user request. In some embodiments a VM may exist in a previously stored VM image, which can be stored in an image repository. The cloud computing environment can search and transfer the image to a server or a user system. The cloud computing environment can then boot the image on the server or user system.

While the foregoing has been described in some detail for purposes of clarity and understanding, it will be clear to one skilled in the art from a reading of this disclosure that various changes in form and detail can be made without departing from the true scope of the disclosure. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method, implemented using a computer system comprising one or more processors and system memory, of conducting directed evolution, the method comprising:
   (a) receiving, by the computer system, an unfiltered data set having information from physical measurements of molecules, wherein the unfiltered data set comprises the following information for each of a plurality of variant biomolecules: (i) the variant biomolecule's activity on a ligand in a binding site of the variant biomolecule, (ii) a sequence of the variant biomolecule, wherein the sequence is a nucleic acid sequence or a protein sequence, and (iii) one or more geometric parameters characterizing the geometry of the variant biomolecule regarding the ligand in the binding site of the variant biomolecule;
   (b) filtering, by the one or more processors, the unfiltered data set to generate a filtered data subset, comprising:
      obtaining a plurality of selected data subsets from the unfiltered data set, each selected data subset is obtained by removing from the unfiltered data set at least one of the geometric parameters of the plurality of variant biomolecules and/or removing certain variant biomolecules having geometric parameter values outside defined ranges,
      training a plurality of sequence activity models using the plurality of selected data subsets, wherein the sequence of the variant biomolecule and one or more of the geometric parameters are independent variables of the sequence activity models and the variant biomolecule's activity on the ligand is a dependent variable of the sequence activity models,
      testing the plurality of sequence activity models' predictive abilities to predict variant biomolecules' activities on the ligand, and
      identifying, as the filtered data subset, a selected data subset that is used to train a sequence activity model having a higher predictive ability than a sequence activity model trained with the unfiltered data set
   (c) applying, by the one or more processors, a sequence activity model trained using the filtered data subset to a plurality of new variant biomolecules, and identifying, using the one or more processors, one or more new variant biomolecules that are predicted by the sequence activity model trained using the filtered data subset as having a desired level of the activity, wherein each variant biomolecule of the plurality of new variant biomolecules is different from the plurality of variant biomolecules; and
   (d) synthesizing or expressing the one or more new variant biomolecules identified in (c); and
   (e) assaying the one or more new variant biomolecules' activities on the ligand, wherein the one or more new variant biomolecules' activities on the ligand are improved over the plurality of variant biomolecules.

2. The method of claim 1, wherein the filtering the unfiltered data set is performed with a genetic algorithm that varies thresholds for removing information associated with the geometric parameters for one or more of the variant biomolecules.

3. The method of claim 1, wherein applying the sequence activity model trained using the filtered data subset comprises recombining or mutating one or more known variant biomolecules to obtain potential new variant biomolecules, the one or more known variant biomolecules are predicted by the sequence activity model to have activities meeting a criterion.

4. The method of claim 3, further comprising evaluating the potential new variant biomolecules using the sequence activity model trained using the filtered data subset as a fitness function to identify the one or more new variant biomolecules.

5. The method of claim 1, further comprising
   producing a structural model for each of the new variant biomolecules; and
   using the structural models to generate geometric parameters characterizing the geometry of the ligand in the binding sites of the new variant biomolecules.

6. The method of claim 1, further comprising receiving structural models of variant biomolecules and determining the one or more geometric parameters using the structural models.

7. The method of claim 6, wherein the structural models are homology models, and optionally wherein the homology models are prepared using physical structural measurement details of biomolecules.

8. The method of claim 7, wherein the physical structural measurement details of biomolecules comprise three-dimensional positions of atoms obtained by NMR or x-ray crystallography.

9. The method of claim 6, further comprising using a docker to determine the one or more geometric parameters.

10. The method of claim 1, wherein the information for each of the plurality of variant biomolecules further comprises (iv) an interaction energy characterizing the interaction of the ligand in the binding site.

11. The method of claim 10, further comprising using a docker to determine the interaction energy.

12. The method of claim 1, wherein the sequence activity model trained using the filtered data subset is obtained by a support vector machine, a multiple linear regression, a principal component regression, a partial least square regression, or a neural network.

13. The method of claim 1, wherein the plurality of variant biomolecules comprises a plurality of enzymes.

14. The method of claim 13, wherein the activity of the variant biomolecule on a ligand is the activity of an enzyme on a substrate.

15. The method of claim 1, further comprising assaying the new variant biomolecules for activity.

16. The method of claim 1, wherein the filtering the unfiltered data set comprises removing from the unfiltered data set certain variant biomolecules having geometric parameter values outside defined ranges.

17. The method of claim 1, wherein the filtering the unfiltered data set is performed with a genetic algorithm.

18. The method of claim 1, wherein each of the one or more new variant biomolecules has a sequence that differs from the sequences of the variant biomolecules providing information for the data set of (a).

19. A computer program product comprising one or more computer- readable non-transitory storage media having stored thereon computer-executable instructions that, when executed by one or more processors of a computer system, cause the computer system to:
   (a) receive an unfiltered data set having information from physical measurements of molecules, wherein the unfiltered data set comprises the following information for each of a plurality of variant biomolecules: (i) the variant biomolecule's activity on a ligand in a binding site of the variant biomolecule, (ii) a sequence of the variant biomolecule, wherein the sequence is a nucleic acid sequence or a protein sequence, and (iii) one or more geometric parameters characterizing the geometry of the variant biomolecule regarding the ligand in the binding site of the variant biomolecule;
   (b) filter the unfiltered data set to generate a filtered data subset, comprising:
      obtaining a plurality of selected data subsets from the unfiltered data set, each selected data subset is obtained by removing from the unfiltered data set at least one of the geometric parameters of the plurality of variant biomolecules and/or removing certain variant biomolecules having geometric parameter values outside defined ranges,
      training a plurality of sequence activity models using the plurality of selected data subsets, wherein the sequence of the variant biomolecule and one or more of the geometric parameters are independent variables of the sequence activity models and the variant biomolecule's activity on the ligand is a dependent variable of the sequence activity models,
      testing the plurality of sequence activity models' predictive abilities to predict variant biomolecules' activities on the ligand, and
      identifying, as the filtered data subset, a selected data subset that is used to train a sequence activity model having a higher predictive ability than a sequence activity model trained with the unfiltered data set;
   (c) apply a sequence activity model trained using the filtered data subset to a plurality of new variant biomolecules, and identify one or more new biomolecule variants that are predicted by the sequence activity model trained using the filtered data subset as having a desired level of the activity on the ligand, wherein each variant biomolecule of the plurality of new variant biomolecules is different from the plurality of variant biomolecules; and
   (d) control an automated synthesis apparatus to synthesize or an expression system to express the one or more new variant biomolecules identified in (c), wherein the one or more new variant biomolecules' activities on the ligand are improved over the plurality of variant biomolecules as measured by an assay.

20. A computer system, comprising: one or more processors; system memory; and one or more computer-readable storage media having stored thereon computer-executable instructions that, when executed by the one or more processors, cause the computer system to:
   (a) receive an unfiltered data set having information from physical measurements of molecules, wherein the unfiltered data set comprises the following information for each of a plurality of variant biomolecules: (i) the variant biomolecule's activity on a ligand in a binding site of the variant biomolecule, (ii) a sequence of the variant biomolecule, wherein the sequence is a nucleic acid sequence or a protein sequence, and (iii) one or more geometric parameters characterizing the geometry of the variant biomolecule regarding the ligand in the binding site of the variant biomolecule;
   (b) filter the unfiltered data set to generate a filtered data subset, comprising:
      obtaining a plurality of selected data subsets from the unfiltered data set, each selected data subset is obtained by removing from the unfiltered data set at least one of the geometric parameters of the plurality of variant biomolecules and/or removing certain variant biomolecules having geometric parameter values outside defined ranges ,
      training a plurality of sequence activity models using the plurality of selected data subsets, wherein the sequence of the variant biomolecule and one or more of the geometric parameters are independent variables of the sequence activity models and the variant biomolecule's activity on the ligand is a dependent variable of the sequence activity models,
      testing the plurality of sequence activity models' predictive abilities to predict variant biomolecules' activities on the ligand, and identifying, as the filtered data subset, a selected data subset that is used to train a sequence activity model having a higher predictive ability than a sequence activity model trained with the unfiltered data set;
   (c) apply a sequence activity model trained using the filtered data subset to a plurality of new variant biomolecules, and identify one or more new biomolecule variants that are predicted by the sequence activity model trained using the filtered data subset as having a desired level of the activity on the ligand, wherein each variant biomolecule of the plurality of new variant biomolecules is different from the plurality of variant biomolecules; and (d) control an automated synthesis apparatus to synthesize or an expression system to express the one or more new biomolecule variants identified in (c), wherein the one or more new variant biomolecules' activities on the ligand are improved over the plurality of variant biomolecules as measured by an assay.

* * * * *